(12) United States Patent
He et al.

(10) Patent No.: US 8,698,117 B2
(45) Date of Patent: *Apr. 15, 2014

(54) INDENO-FUSED RING COMPOUNDS

(75) Inventors: Meng He, Murrysville, PA (US); Anil Kumar, Murrysville, PA (US); Darrin R. Dabideen, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/222,457

(22) Filed: Aug. 31, 2011

(65) Prior Publication Data

US 2012/0126185 A1  May 24, 2012

Related U.S. Application Data

(63) Continuation-in-part of application No. 12/928,687, filed on Dec. 16, 2010, which is a continuation-in-part of application No. 12/329,092, filed on Dec. 5, 2008, now Pat. No. 8,211,338, which is a continuation-in-part of application No. 10/846,629, filed on May 17, 2004, now Pat. No. 7,342,112.

(60) Provisional application No. 60/484,100, filed on Jul. 1, 2003.

(51) Int. Cl.
| | |
|---|---|
| C07D 311/00 | (2006.01) |
| C07D 311/92 | (2006.01) |
| C07D 311/94 | (2006.01) |
| C09K 9/02 | (2006.01) |
| G02B 5/23 | (2006.01) |
| G03C 1/73 | (2006.01) |

(52) U.S. Cl.
USPC ........... 250/586; 544/150; 544/378; 546/196; 549/382; 560/139; 564/161

(58) Field of Classification Search
None
See application file for complete search history.

(56) References Cited

U.S. PATENT DOCUMENTS

| | | | |
|---|---|---|---|
| 2,319,826 A | 5/1943 | Pellett | |
| 2,334,446 A | 11/1943 | Serrell | |
| 2,475,921 A | 7/1949 | Smith | |
| 2,481,830 A | 9/1949 | Dreyer | |
| 2,544,659 A | 3/1951 | Dreyer | |
| 3,276,316 A | 10/1966 | Makas | |
| 3,361,706 A | 1/1968 | Meriwether et al. | |
| 3,562,172 A | 2/1971 | Ono et al. | |
| 3,567,605 A | 3/1971 | Becker | |
| 3,578,602 A | 5/1971 | Ono et al. | |
| 3,653,863 A | 4/1972 | Araujo et al. | |
| 4,039,254 A | 8/1977 | Harsch | |
| 4,043,637 A | 8/1977 | Hovey | |
| 4,049,338 A | 9/1977 | Slocum | |
| 4,166,043 A | 8/1979 | Uhlmann et al. | |
| 4,190,330 A | 2/1980 | Berreman | |
| 4,215,010 A | 7/1980 | Hovey et al. | |
| 4,279,474 A | 7/1981 | Belgorod | |
| 4,342,668 A | 8/1982 | Hovey et al. | |
| 4,367,170 A | 1/1983 | Uhlmann et al. | |
| 4,549,894 A | 10/1985 | Araujo et al. | |

(Continued)

FOREIGN PATENT DOCUMENTS

| | | |
|---|---|---|
| EP | 0313941 A1 | 5/1989 |
| EP | 0315224 A1 | 5/1989 |

(Continued)

OTHER PUBLICATIONS

Kvasnikov, E.D. et al., "Birefringence in Polyvinylcinnamate Films Induced by Polarized Light," Doklady Akademii nauk SSSR, 1977, pp. 633-636, vol. 237, No. 3.

(Continued)

*Primary Examiner* — Kamal Saeed
(74) *Attorney, Agent, or Firm* — Deborah M. Attman

(57) ABSTRACT

The present invention relates to compounds represented by the following Formulas (I) and (II),

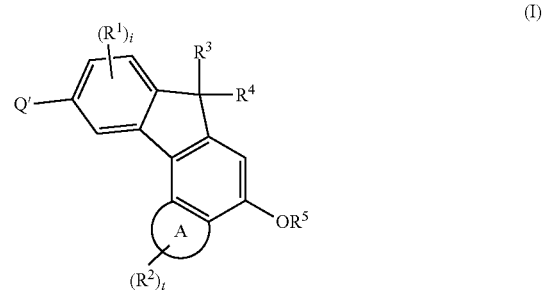

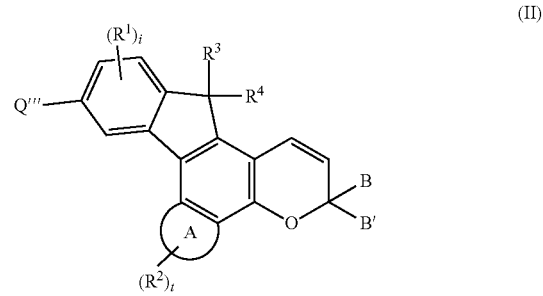

Ring-A of Formulas I and II can be, for example, an aryl group, and Q' and Q''' can each be independently selected from groups, such as, halogen, —OH, —CN, amine groups, amide groups, carboxylic acid ester groups, carboxylic acid groups, alkenyl groups, alkynyl groups, carbonate groups, sulfide groups, and sulfonic acid ester groups. The present invention also relates to photochromic compositions and photochromic articles that include one or more photochromic compounds, such as represented by Formula II.

6 Claims, 1 Drawing Sheet

(56) References Cited

U.S. PATENT DOCUMENTS

| | | |
|---|---|---|
| 4,556,605 A | 12/1985 | Mogami et al. |
| 4,637,698 A | 1/1987 | Kwak et al. |
| 4,637,896 A | 1/1987 | Shannon |
| 4,648,925 A | 3/1987 | Goepfert et al. |
| 4,683,153 A | 7/1987 | Goepfert et al. |
| 4,685,783 A | 8/1987 | Heller et al. |
| 4,720,356 A | 1/1988 | Chu |
| 4,728,173 A | 3/1988 | Toth |
| 4,756,605 A | 7/1988 | Okada et al. |
| 4,756,973 A | 7/1988 | Sakagami et al. |
| 4,785,097 A | 11/1988 | Kwak |
| 4,810,433 A | 3/1989 | Takayanagi et al. |
| 4,816,584 A | 3/1989 | Kwak et al. |
| 4,818,096 A | 4/1989 | Heller et al. |
| 4,826,977 A | 5/1989 | Heller et al. |
| 4,838,673 A | 6/1989 | Richards et al. |
| 4,863,763 A | 9/1989 | Takeda et al. |
| 4,865,668 A | 9/1989 | Goepfert et al. |
| 4,873,026 A | 10/1989 | Behre et al. |
| 4,873,029 A | 10/1989 | Blum |
| 4,880,667 A | 11/1989 | Welch |
| 4,929,693 A | 5/1990 | Akashi et al. |
| 4,931,219 A | 6/1990 | Kwiatkowski et al. |
| 4,931,220 A | 6/1990 | Haynes et al. |
| 4,931,221 A | 6/1990 | Heller |
| 4,959,471 A | 9/1990 | Melzig |
| 4,962,013 A | 10/1990 | Tateoka et al. |
| 4,974,941 A | 12/1990 | Gibbons et al. |
| 4,977,028 A | 12/1990 | Goepfert et al. |
| 4,983,479 A | 1/1991 | Broer et al. |
| 5,066,818 A | 11/1991 | Gemert et al. |
| 5,067,795 A | 11/1991 | Senatore |
| 5,073,294 A | 12/1991 | Shannon et al. |
| 5,130,058 A | 7/1992 | Tanaka et al. |
| 5,130,353 A | 7/1992 | Fischer et al. |
| 5,139,707 A | 8/1992 | Guglielmetti et al. |
| 5,155,607 A | 10/1992 | Inoue et al. |
| 5,166,345 A | 11/1992 | Akashi et al. |
| 5,180,470 A | 1/1993 | Smith et al. |
| 5,180,524 A | 1/1993 | Casilli et al. |
| 5,185,390 A | 2/1993 | Fischer et al. |
| 5,186,867 A | 2/1993 | Castaldi et al. |
| 5,189,448 A | 2/1993 | Yaguchi |
| 5,194,973 A | 3/1993 | Isogai et al. |
| 5,200,116 A | 4/1993 | Heller |
| 5,202,053 A | 4/1993 | Shannon |
| 5,204,850 A | 4/1993 | Obata |
| 5,238,931 A | 8/1993 | Yoshikawa et al. |
| 5,238,981 A | 8/1993 | Knowles |
| 5,247,377 A | 9/1993 | Omeis et al. |
| 5,274,132 A | 12/1993 | VanGemert |
| 5,289,547 A | 2/1994 | Ligas et al. |
| 5,359,085 A | 10/1994 | Iwamoto et al. |
| 5,359,443 A | 10/1994 | Toyooka et al. |
| 5,384,077 A | 1/1995 | Knowles |
| 5,389,287 A | 2/1995 | Nishiyama et al. |
| 5,389,698 A | 2/1995 | Chigrinov et al. |
| 5,395,566 A | 3/1995 | Kobayakawa et al. |
| 5,405,958 A | 4/1995 | VanGemert |
| 5,464,669 A | 11/1995 | Kang et al. |
| 5,466,398 A | 11/1995 | Van Gemert et al. |
| 5,543,267 A | 8/1996 | Stumpe et al. |
| 5,543,533 A | 8/1996 | Allegrini et al. |
| 5,602,661 A | 2/1997 | Schadt et al. |
| 5,608,567 A | 3/1997 | Grupp |
| 5,641,846 A | 6/1997 | Bieringer et al. |
| 5,644,416 A | 7/1997 | Morikawa et al. |
| 5,645,767 A | 7/1997 | Van Gemert |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,744,070 A | 4/1998 | Kumar |
| 5,746,949 A | 5/1998 | Shen et al. |
| 5,808,100 A | 9/1998 | Momoda et al. |
| 5,831,090 A | 11/1998 | Paltchkov et al. |
| 5,846,452 A | 12/1998 | Gibbons et al. |
| 5,869,658 A | 2/1999 | Lin et al. |
| 5,903,330 A | 5/1999 | Funfschilling et al. |
| 5,943,104 A | 8/1999 | Moddel et al. |
| 5,952,515 A | 9/1999 | Melzig et al. |
| 5,955,520 A | 9/1999 | Heller et al. |
| 5,961,892 A | 10/1999 | Gemert et al. |
| 5,962,617 A | 10/1999 | Slagel |
| 6,004,486 A | 12/1999 | Chan |
| 6,022,497 A | 2/2000 | Kumar |
| 6,025,026 A | 2/2000 | Smith et al. |
| 6,036,890 A | 3/2000 | Melzig et al. |
| 6,049,428 A | 4/2000 | Khan et al. |
| 6,060,001 A | 5/2000 | Welch et al. |
| 6,068,797 A | 5/2000 | Hunt |
| 6,080,338 A | 6/2000 | Kumar |
| 6,106,744 A | 8/2000 | Van Gemert et al. |
| 6,113,814 A | 9/2000 | Gemert et al. |
| 6,136,968 A | 10/2000 | Chamontin et al. |
| 6,141,135 A | 10/2000 | Nagoh et al. |
| 6,146,554 A | 11/2000 | Melzig et al. |
| 6,150,430 A | 11/2000 | Walters et al. |
| 6,153,126 A | 11/2000 | Kumar |
| 6,160,597 A | 12/2000 | Schadt et al. |
| 6,187,444 B1 | 2/2001 | Bowles, III et al. |
| 6,208,393 B1 | 3/2001 | Bawolek et al. |
| 6,239,778 B1 | 5/2001 | Palffy-Muhoray et al. |
| 6,245,399 B1 | 6/2001 | Sahouani et al. |
| 6,256,152 B1 | 7/2001 | Coldrey et al. |
| 6,268,055 B1 | 7/2001 | Walters et al. |
| 6,281,366 B1 | 8/2001 | Frigoli et al. |
| 6,284,418 B1 | 9/2001 | Trantolo |
| 6,294,112 B1 | 9/2001 | Clarke et al. |
| 6,296,785 B1 | 10/2001 | Nelson et al. |
| 6,303,673 B1 | 10/2001 | Clarke et al. |
| 6,312,811 B1 | 11/2001 | Frigoli et al. |
| 6,334,681 B1 | 1/2002 | Perrott et al. |
| 6,337,409 B1 | 1/2002 | Hughes et al. |
| 6,338,808 B1 | 1/2002 | Kawata et al. |
| 6,340,766 B1 | 1/2002 | Lin |
| 6,348,604 B1 | 2/2002 | Nelson et al. |
| 6,353,102 B1 | 3/2002 | Kumar |
| 6,369,869 B2 | 4/2002 | Schadt et al. |
| 6,432,544 B1 | 8/2002 | Stewart et al. |
| 6,433,043 B1 | 8/2002 | Misura et al. |
| 6,436,525 B1 | 8/2002 | Welch et al. |
| 6,474,695 B1 | 11/2002 | Schneider et al. |
| 6,506,488 B1 | 1/2003 | Stewart et al. |
| 6,531,076 B2 | 3/2003 | Crano et al. |
| 6,555,028 B2 | 4/2003 | Walters et al. |
| 6,555,029 B1 | 4/2003 | Ruscio et al. |
| 6,579,422 B1 | 6/2003 | Kakinuma |
| 6,597,422 B1 | 7/2003 | Funfschilling et al. |
| 6,602,603 B2 | 8/2003 | Welch et al. |
| 6,613,433 B2 | 9/2003 | Yamamoto et al. |
| 6,630,597 B1 | 10/2003 | Lin et al. |
| 6,641,874 B2 | 11/2003 | Kuntz et al. |
| 6,660,727 B1 | 12/2003 | Mann et al. |
| 6,683,709 B2 | 1/2004 | Mann et al. |
| 6,690,495 B1 | 2/2004 | Kosa et al. |
| 6,705,569 B1 | 3/2004 | Sanders et al. |
| 6,717,644 B2 | 4/2004 | Schadt et al. |
| 6,723,859 B2 | 4/2004 | Kawabata et al. |
| 6,736,998 B2 | 5/2004 | Petrovskaia et al. |
| 6,761,452 B2 | 7/2004 | Moravec et al. |
| 6,797,383 B2 | 9/2004 | Nishizawa et al. |
| 6,806,930 B2 | 10/2004 | Moia |
| 6,844,686 B1 | 1/2005 | Schneck et al. |
| 6,874,888 B1 | 4/2005 | Dudai |
| 6,891,038 B2 | 5/2005 | Krongauz et al. |
| 6,986,946 B2 | 1/2006 | Nishizawa et al. |
| 7,008,568 B2 | 3/2006 | Qin |
| 7,097,303 B2 | 8/2006 | Kumar et al. |
| 7,118,806 B2 | 10/2006 | Nishizawa et al. |
| 7,166,357 B2 | 1/2007 | Kumar et al. |
| 7,247,262 B2 | 7/2007 | Evans et al. |
| 7,256,921 B2 | 8/2007 | Kumar et al. |
| 7,262,295 B2 | 8/2007 | Walters et al. |

(56) References Cited

U.S. PATENT DOCUMENTS

| | | | |
|---|---|---|---|
| 7,320,826 B2 | 1/2008 | Kumar et al. |
| 7,342,112 B2 | 3/2008 | Kumar et al. |
| 7,357,503 B2 | 4/2008 | Mosse et al. |
| 7,416,682 B2 | 8/2008 | Frigoli et al. |
| 7,465,415 B2 | 12/2008 | Wang et al. |
| 7,521,004 B2 | 4/2009 | Momoda et al. |
| 7,557,208 B2 | 7/2009 | Walters et al. |
| 2002/0039627 A1 | 4/2002 | Ichihashi et al. |
| 2002/0090516 A1 | 7/2002 | Loshak et al. |
| 2002/0167639 A1 | 11/2002 | Coates et al. |
| 2002/0180916 A1 | 12/2002 | Schadt et al. |
| 2003/0008958 A1 | 1/2003 | Momoda et al. |
| 2003/0045612 A1 | 3/2003 | Misura et al. |
| 2003/0189684 A1 | 10/2003 | Kuntz et al. |
| 2004/0046927 A1 | 3/2004 | Montgomery |
| 2004/0090570 A1 | 5/2004 | Kosa et al. |
| 2004/0125337 A1 | 7/2004 | Boulineau et al. |
| 2004/0158028 A1 | 8/2004 | Buhler |
| 2004/0185255 A1 | 9/2004 | Walters et al. |
| 2004/0185268 A1 | 9/2004 | Kumar et al. |
| 2004/0186241 A1 | 9/2004 | Gemert |
| 2004/0191520 A1 | 9/2004 | Kumar et al. |
| 2004/0223221 A1 | 11/2004 | Sugimura et al. |
| 2004/0228817 A1 | 11/2004 | Simon et al. |
| 2004/0228818 A1 | 11/2004 | Simon et al. |
| 2005/0003107 A1 | 1/2005 | Kumar et al. |
| 2005/0004361 A1 | 1/2005 | Kumar et al. |
| 2005/0012998 A1 | 1/2005 | Kumar et al. |
| 2005/0146680 A1 | 7/2005 | Muisener et al. |
| 2005/0151926 A1 | 7/2005 | Kumar et al. |
| 2005/0202267 A1 | 9/2005 | Ha et al. |
| 2005/0276767 A1 | 12/2005 | Blin et al. |
| 2006/0022176 A1 | 2/2006 | Wang et al. |
| 2007/0041073 A1 | 2/2007 | Kumar et al. |
| 2007/0188698 A1 | 8/2007 | Mosse et al. |
| 2007/0275234 A1 | 11/2007 | Lim et al. |
| 2009/0309076 A1 | 12/2009 | He et al. |
| 2011/0129678 A1 | 6/2011 | He et al. |
| 2011/0140056 A1 | 6/2011 | He et al. |
| 2011/0143141 A1 | 6/2011 | He et al. |

FOREIGN PATENT DOCUMENTS

| | | | |
|---|---|---|---|
| EP | 0321563 A1 | 6/1989 |
| EP | 0331233 A2 | 9/1989 |
| EP | 0336193 A2 | 10/1989 |
| EP | 0397263 A1 | 11/1990 |
| EP | 0442166 A1 | 8/1991 |
| EP | 0446717 A2 | 9/1991 |
| EP | 0488164 A2 | 6/1992 |
| EP | 0543678 A1 | 5/1993 |
| EP | 0619358 A1 | 10/1994 |
| EP | 0686685 A2 | 12/1995 |
| EP | 0770116 A1 | 5/1997 |
| EP | 0772069 A1 | 5/1997 |
| EP | 0965628 A1 | 12/1999 |
| EP | 1044979 A2 | 10/2000 |
| EP | 1162482 A2 | 12/2001 |
| EP | 1184379 A1 | 3/2002 |
| EP | 1203967 A1 | 5/2002 |
| EP | 1394595 A1 | 3/2004 |
| EP | 1674460 A1 | 6/2006 |
| GB | 583842 | 1/1947 |
| GB | 2169417 A | 7/1986 |
| GB | 2189417 A | 10/1987 |
| JP | 59135428 A | 8/1984 |
| JP | 63175094 A | 7/1988 |
| JP | 63234084 A | 9/1988 |
| JP | 63250381 A | 10/1988 |
| JP | 63250382 A | 10/1988 |
| JP | 63275587 A | 11/1988 |
| JP | 64030744 U | 2/1989 |
| JP | 64090286 | 4/1989 |
| JP | 1170904 A | 7/1989 |
| JP | 01258681 | 10/1989 |
| JP | 280490 A | 3/1990 |
| JP | 2101080 A | 4/1990 |
| JP | 2194084 A | 7/1990 |
| JP | 2243694 A | 9/1990 |
| JP | 03200118 | 2/1991 |
| JP | 03200218 A | 2/1991 |
| JP | 366692 A | 3/1991 |
| JP | 3137634 A | 6/1991 |
| JP | 3221563 A | 9/1991 |
| JP | 3227988 A | 10/1991 |
| JP | 4117387 A | 4/1992 |
| JP | 4358117 A | 12/1992 |
| JP | 6214195 A | 8/1994 |
| JP | 6295687 A | 10/1994 |
| JP | 6306354 A | 11/1994 |
| JP | 741758 A | 2/1995 |
| JP | 762337 A | 3/1995 |
| JP | 7165762 A | 6/1995 |
| JP | 8027155 A | 1/1996 |
| JP | 8027461 A | 1/1996 |
| JP | 8157467 A | 6/1996 |
| JP | 8176139 A | 7/1996 |
| JP | 8209119 A | 8/1996 |
| JP | 8295690 A | 11/1996 |
| JP | 973149 A | 3/1997 |
| JP | 9124645 A | 5/1997 |
| JP | 2001114775 A | 4/2001 |
| JP | 2005112772 A | 4/2005 |
| JP | 2005187420 A | 7/2005 |
| WO | 8905464 A1 | 6/1989 |
| WO | 8911674 A1 | 11/1989 |
| WO | 9201959 A1 | 2/1992 |
| WO | 9310112 A1 | 5/1993 |
| WO | 9317071 A1 | 9/1993 |
| WO | 9601884 A1 | 1/1996 |
| WO | 9705213 A1 | 2/1997 |
| WO | 9706455 A1 | 2/1997 |
| WO | 9710241 A1 | 3/1997 |
| WO | 9722894 A1 | 6/1997 |
| WO | 9819207 A1 | 5/1998 |
| WO | 9920630 A1 | 4/1999 |
| WO | 9943666 A1 | 9/1999 |
| WO | 0015630 A1 | 3/2000 |
| WO | 0019252 A1 | 4/2000 |
| WO | 0035902 A1 | 6/2000 |
| WO | 0077559 A1 | 12/2000 |
| WO | 0102449 A2 | 1/2001 |
| WO | 0119813 A1 | 3/2001 |
| WO | 0155960 A1 | 8/2001 |
| WO | 0170719 A2 | 9/2001 |
| WO | 0177112 A2 | 10/2001 |
| WO | 0229489 A2 | 4/2002 |
| WO | 02058921 A1 | 8/2002 |
| WO | 03019270 A1 | 3/2003 |
| WO | 03032066 A1 | 4/2003 |
| WO | 2004003107 A1 | 1/2004 |
| WO | 2004011964 A1 | 2/2004 |
| WO | 2004041961 A1 | 5/2004 |
| WO | 2005084826 A1 | 9/2005 |
| WO | 2005085912 A1 | 9/2005 |

OTHER PUBLICATIONS

Kozenkov, V.M. et al., "Photoanisotropic Effects in Pole (Vinyl-Cinnamate) Derivatives and Their Applications," Mol. Cryst. Liq. Cryst., 2004, pp. 251-267, vol. 409.

Hikmet, R.A.M. et al., "Gel Layer for Inducing Adjustable Pretilt Angles in Liquid Crystal Systems," J. App. Phys. Aug. 1991, pp. 1265-1266, vol. 70, No. 3.

Schadt, Martin et al., " Surface-Induced Parallel Alignment of Liquid Crystals by Linearly Polymerized Photopolymers," Jpn. J. Appl. Phys., Jul. 1992, pp. 2155-2164, vol. 31, No. 7.

Schadt, Martin, "Optics and Applications of Photo-Aligned Liquid Crystalline Surfaces," Nonlinear Optics, 2000, pp. 1-12, vol. 25.

Schadt, Martin, "Liquid Crystal Displays and Novel Optical Thin Films Enabled by Photo-Alignment," Mol. Cryst. Liq. Cryst., 2001, pp. 151-169, vol. 364.

(56) References Cited

OTHER PUBLICATIONS

Dyadyusha, A.G. et al., "Light-Induced Planar Orientation of a Nematic Liquid Crystal on an Anisotropic Surface without Microrelief," Ukr. Fiz. Zhurn, (Ukraine), pp. 1059-1062, vol. 35.
Castellane, Joseph A., "Surface Anchoring of Liquid Crystal Molecules on Various Substrates," Mol. Cryst. Liq. Cryst., 1983, pp. 33-41, vol. 94.
Huang, D.D. et al., "Effect of Aligning Layer Thickness on Photo-Aligned Ferroelectric Liquid Crystal Displays," Proceedings of the 6th Chinese Optoelectronics Symposium, Hong Kong China, IEEE (New York), 2003, pp. 231-234.
Chigrinov, V.G. et al., "New Results on Liquid Crystal Alignment by Photopolymerization," Proceedings of the SPIE—The Internationali Society for Optical Engineering, SPIE, 1995, pp. 130-140, vol. 2409.
"Cholesteric Filters and Films" Rolic Ltd. available at http://www.rolic.com/050application/05223content.htm, 2003, 2 pages.
"Dichroic Linear Polarisers," Rolic Ltd. available at http://www.rolic.com/050applicaiton/05313content.htm, 2003, 1 page.
Bachels, Thomas et al., "Novel Photo-Aligned LC-Polymer Wide View Film for TN Displays," Eurodisplay, 2002, pp. 183-186.
Castellano, Joseph A., "Surface Anchoring of Liquid Crystal Molecules on Various Substrates," Mol. Cryst. Liq. Cryst., 1983, pp. 33-41, vol. 94.
Moia, Franco et al., "Optical LLP/LCP devices: A New Generation of Optical Security Elements," Proceedings of SPIE: Optical Security and Counterfeit Deterrence Techniques III, Jan. 27-28, 2000, pp. 196-203, vol. 3973, San Jose, California.
Moia, Franco, "New Coloured Optical Security Elements Using Rolic's LLP/LCP Technology: Devices for 1st to 3rd Level Inspection," Proceedings of SPIE: Optical Security and Counterfeit Deterrence Techniques IV, Jan. 23-25, 2002, pp. 194-202, vol. 4677, San Jose, California.
Sieberle, Hubert et al., Invited paper: Photo-Aligned Anisotropic Optical Thin Films, SID 03 Digest, Society of Information Displays, 2003, pp. 1162-1165.
Atassi, Yomen et al., "Reversible Photoinduced Modifications of Polymers Doped with Photochromes: Anisotropy, Photo-assisted Poling and Surface Gratings," Mol. Cryst. Lig. Cryst., 1998, pp. 11-22, vol. 315.
"Friedel-Crafts and Related Reactions," George A. Olah, Interscience Publishers, 1964, p. 1, vol. 3, Chapter XXXI (Aromatic Ketone Synthesis).
Ishihara, Yuji et al., "Regioselective Friedel-Crafts Acylation of 1,2,3,4-Tetrahydroquinoline and Related Nitrogen Heterocycles: Effects of NH Protective Groups and Ring Size," J. Chem. Soc. Perkin Trans., 1992, pp. 3401-3406, vol. 1.
Wang, Xiao-Jun et al., "Addition of Grignard Reagents to Aryl Acid Chlorides: An Efficient Synthesis of Aryl Ketones," Organic Letters, 2005, pp. 5593-5595, vol. 7, No. 25.
Hattori Tetsutaro et al., "Practical Synthesis of 4'-Methylbiphenyl-2-carboxylic Acid," Synthesis, Jan. 1995, pp. 41-43.
Hattori, Tetsutaro et al., "Facile Construction of the 1-Phenylnaphthyl Skeleton via an Ester-mediated Nucleophilic Aromatic Substitution Reaction. Applications to the Synthesis of Phenylnaphthalide Lignans," J. Chem. Soc. Perkin Trans., 1995, pp. 235-241, vol. 1.
Furrow, Michael E. et al., Practical Procedures for the Preparation of N-tert-Butyldimethylsilylhydrazones and Their Use in Modified Wolff-Kishner Reductions and in the Synthesis of Vinyl Halides and gem-Dihalides, J. Am. Chem. Soc., 2004, pp. 5436-5445, vol. 126, No. 17.
Ishiyama, Tatsuo, "Palladium (0)-Catalyzed Cross-Coupling Reaction of Alkoxydiboron with Haloarenes: A Direct Procedure for Arylboronic Esters," J. Org. Chem., 1995, pp. 7508-7510, vol. 60, No. 23.
"Polymerization" in Hawley's Condensed Chemical Dictionary Thirteenth Edition, 1997, pp. 901-902, published by John Wiley & Sons, Inc., revised by Richard J. Lewis, Sr.

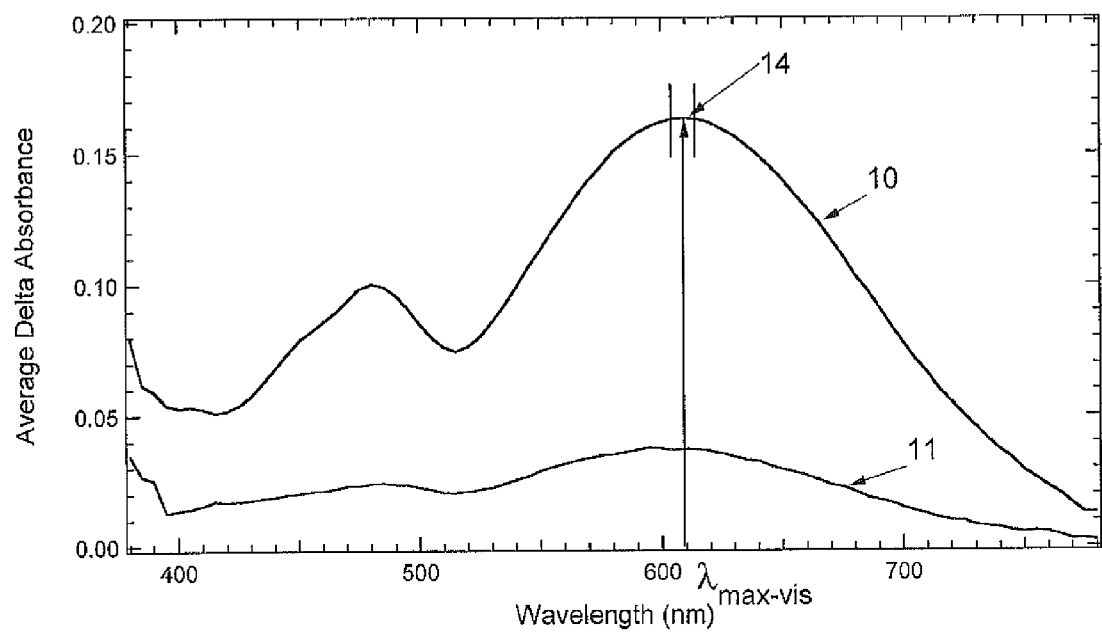

INDENO-FUSED RING COMPOUNDS

CROSS REFERENCE TO RELATED APPLICATIONS

This application is a continuation-in-part of U.S. patent application Ser. No. 12/928,687, filed Dec. 16, 2010, which is a continuation-in-part of U.S. patent application Ser. No. 12/329,092, filed Dec. 5, 2008, which is a continuation-in-part of U.S. patent application Ser. No. 10/846,629, filed May 17, 2004 (now U.S. Pat. No. 7,342,112), which is entitled to and claims the benefit of U.S. Provisional Application Ser. No. 60/484,100, filed Jul. 1, 2003, all of which documents are hereby incorporated herein by reference in their entireties.

FIELD OF THE INVENTION

The present invention relates to indeno-fused ring compounds, including indeno-fused ring pyran compounds, which can be photochromic compounds, and compositions and articles that include the photochromic compounds of the present invention.

BACKGROUND OF THE INVENTION

Photochromic compounds typically have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

Dichroic compounds are compounds that are capable of absorbing one of two orthogonal plane polarized components of transmitted radiation more strongly than the other. Thus, dichroic compounds are capable of linearly polarizing transmitted radiation. As used herein, "linearly polarize" means to confine the vibrations of the electric vector of light waves to one direction or plane. However, although dichroic materials are capable of preferentially absorbing one of two orthogonal plane polarized components of transmitted radiation, if the molecules of the dichroic compound are not suitably positioned or arranged, no net linear polarization of transmitted radiation will be achieved. That is, due to the random positioning of the molecules of the dichroic compound, selective absorption by the individual molecules will cancel each other such that no net or overall linear polarizing effect is achieved. Thus, it is generally necessary to suitably position or arrange the molecules of the dichroic compound within another material in order to form a conventional linear polarizing element, such as a linearly polarizing filter or lens for sunglasses.

In contrast to the dichroic compounds, it is generally not necessary to position or arrange the molecules of conventional photochromic compounds to form a conventional photochromic element. Thus, for example, conventional photochromic elements, such as lenses for photochromic eyewear, can be formed, for example, by spin coating a solution containing a conventional photochromic compound and a "host" material onto the surface of the lens, and suitably curing the resultant coating or layer without arranging the photochromic compound in any particular orientation. Further, even if the molecules of the conventional photochromic compound were suitably positioned or arranged as discussed above with respect to the dichroic compounds, because conventional photochromic compounds do not strongly demonstrate dichroism, elements made therefrom are generally not strongly linearly polarizing.

It would be desirable to develop new photochromic compounds that can exhibit useful photochromic and/or dichroic properties in at least one state, and that can be used in a variety of applications to impart photochromic and/or dichroic properties.

SUMMARY OF THE INVENTION

In accordance with the present invention, there is provided a compound, such as an indeno-fused ring compound, represented by the following Formula I,

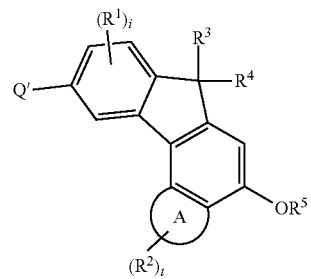

I

Ring-A of Formula I, and other related formulas disclosed further herein, is selected from, aside from the $(R')_m$— group, unsubstituted aryl, substituted aryl, unsubstituted fused ring aryl, substituted fused ring aryl, unsubstituted heteroaryl, and substituted heteroaryl. With some embodiments, Ring-A is selected from aryl, fused ring aryl, and heteroaryl.

The Q' group of Formula-I, and other related formulas disclosed further herein, is selected from halogen, —OH, —$N_3$, —$NR^aR^a$, —$N(R^a)C(O)Q''$, —CN, —$C(O)OR^a$, —$C(O)R^a$, —C≡C—$R^a$, —$C(R^a)$=$C(R^a)(R^a)$, —OC(O)$R^a$, —OC(O)O$R^a$, —S$R^a$, —OS($O_2$)$R^b$, —C(O)N$R^aR^a$ and a lengthening agent L (as described further herein). Each $R^a$ is independently selected from hydrogen, hydrocarbyl and substituted hydrocarbyl each optionally and independently interrupted with at least one of —O—, —S—, —C(O)—, —C(O)O—, —S(O)—, —S($O_2$)—, —N=N—, —N($R_{11}$')— where $R_{11}$' is selected from hydrogen, hydrocarbyl or substituted hydrocarbyl, —Si(O$R_{14}$)$_u$($R_{14}$)$_v$—, where u and v are each independently selected from 0 to 2, provided that the sum of u and v is 2, and each $R_{14}$ is independently selected from hydrogen, hydrocarbyl and substituted hydrocarbyl, and combinations of two or more thereof. Alternatively, two $R^a$ groups can come together with —N and optionally an additional hetero atom selected from N and O to form a heterocycloalkyl. The $R^b$ group is selected from perhalohydrocarbyl, and Q" is selected from halo, —$OR^a$, —$NR^aR^a$, —C(O)$OR^a$, —$SR^a$, and hydrocarbyl or substituted hydrocarbyl, wherein the substituents are selected from —OH, —$NR^aR^a$, —C(O)$OR^a$, —$SR^a$.

Subscript i of Formula I is selected from 0 to 3. Subscript t of Formula I is selected from 0 to a total number of positions to which $R^2$ can be bonded to Ring-A, such as from 0 to 10, or 0 to 7, or 0 to 5, or 0 to 4, or 0 to 3. Ring positions to which an $R^1$ group is not bonded, can instead have hydrogen groups bonded thereto. Similarly, Ring-A positions to which an $R^2$ group is not bonded, can instead have hydrogen groups bonded thereto. With further reference to Formula I, $R^1$ for each i, and $R^2$ for each t, are each independently selected from, hydrocarbyl and substituted hydrocarbyl each optionally and independently interrupted with at least one of —O—, —S—, —C(O)—, —C(O)O—, —S(O)—, —S(O$_2$)—, —N=N—, —N($R_{11}$')— where $R_{11}$' is selected from hydrogen, hydrocarbyl or substituted hydrocarbyl, —Si(O$R_{14}$)$_u$($R_{14}$)$_v$—, where u and v are each independently selected from 0 to 2 (e.g., 0, 1 or 2), provided that the sum of u and v is 2, and each $R_{14}$ is independently selected from hydrogen, hydrocarbyl and substituted hydrocarbyl, and combinations of two or more thereof; halogen; cyano; and —N($R_{11}$')$R_{12}$', wherein $R_{11}$' and $R_{12}$' are each independently selected from hydrogen, hydrocarbyl or substituted hydrocarbyl, or $R_{11}$' and $R_{12}$' together form a ring structure optionally including at least one heteroatom.

The $R^3$ and $R^4$ groups of Formula I are each independently selected from, hydrogen; hydrocarbyl and substituted hydrocarbyl each optionally and independently interrupted with at least one of —O—, —S—, —C(O)—, —C(O)O—, —S(O)—, —S(O$_2$)—, —N=N—, —N($R_{11}$')— where $R_{11}$' is selected from hydrogen, hydrocarbyl or substituted hydrocarbyl, —Si(O$R_{14}$)$_u$($R_{14}$)$_v$—, where u and v are each independently selected from 0 to 2 (e.g., 0, 1 or 2), provided that the sum of u and v is 2, and each $R_{14}$ is independently selected from hydrogen, hydrocarbyl and substituted hydrocarbyl, and combinations of two or more thereof. Alternatively, $R^3$ and $R^4$ can together form a ring structure optionally including at least one heteroatom.

The $R^5$ group of Formula I is selected from hydrogen, —C(O)—$R^{13}$ or —S(O$_2$)$R^{13}$ wherein $R^{13}$ is optionally substituted hydrocarbyl, or optionally substituted halohydrocarbyl.

In accordance with the present invention, there is further provided a compound, such as an indeno-fused ring pyran compound, represented by the following Formula II,

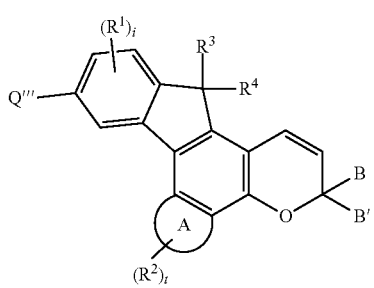

II

The various groups and subscripts of Formula II, such as $R^1$, $R^2$, $R^3$, and $R^4$, subscripts i and t, and Ring-A, are each as described previously and further herein with regard to the compound represented by Formula I. The Q''' group of Formula II, is selected from halogen, —OH, —N$_3$, —N$R^aR^a$, —N($R^a$)C(O)Q''', —CN, —C(O)O$R^a$, —C(O)$R^a$, —C≡C—$R^a$, —C($R^a$)=C($R^a$)($R^a$), —OC(O)$R^a$, —OC(O)O$R^a$, —S$R^a$, —OS(O$_2$)$R^b$ and —C(O)N$R^aR^a$. Each $R^a$ group is independently selected from hydrogen, hydrocarbyl and substituted hydrocarbyl each optionally and independently interrupted with at least one of —O—, —S—, —C(O)—, —C(O)O—, —S(O)—, —S(O$_2$)—, —N=N—, —N($R_{11}$')— where $R_{11}$' is selected from hydrogen, hydrocarbyl or substituted hydrocarbyl, —Si(O$R_{14}$)$_u$($R_{14}$)$_v$—, where u and v are each independently selected from 0 to 2, provided that the sum of u and v is 2, and each $R_{14}$ is independently selected from hydrogen, hydrocarbyl and substituted hydrocarbyl, and combinations of two or more thereof, or two $R^a$ groups come together with —N and optionally an additional hetero atom selected from N and O to form a heterocycloalkyl. The $R^b$ group is selected from perhalohydrocarbyl, and Q" is selected from halo, —$OR^a$, —$NR^aR^a$, —C(O)$OR^a$, —$SR^a$, and hydrocarbyl or substituted hydrocarbyl, wherein the substituents are selected from —OH, —$NR^aR^a$, —C(O)$OR^a$, —$SR^a$.

The B and B' groups of Formula II are each independently selected from hydrogen, unsubstituted aryl, substituted aryl, unsubstituted heteroaryl, substituted heteroaryl, polyalkoxy, and polyalkoxy having a polymerizable group, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

In accordance with the present invention there is further provided photochromic compositions and articles that include one or more of the compounds of the present invention, such as compounds represented by Formula II.

BRIEF DESCRIPTION OF THE DRAWINGS

FIG. 1 is a graphical representation of two average difference absorption spectrum obtained for a photochromic compound according to various non-limiting embodiments disclosed herein using the CELL METHOD.

DETAILED DESCRIPTION OF THE INVENTION

As used herein and in the claims, the term "actinic radiation" means electromagnetic radiation that is capable of transforming a photochromic material from one form or state to another.

As used herein and in the claims, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation, and which includes at least one photochromic compound.

As used herein and in the claims, the term "halo" and similar terms, such as halo group, halogen, and halogen group means F, Cl, Br and/or I, such as fluoro, chloro, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein and in the claims, the articles "a," "an," and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be under stood as modified in all instances by the term "about."

As used herein and in the claims, the term "precursor" and related terms, such as "precursors" with regard to the various groups, for example, $R^1$, $R^2$, $R^3$, $R^4$, $R^5$, Q', Q''', B, B', and L, of the compounds and intermediates described herein, for example, the indeno-fused ring compounds represented by Formula I, the indeno-fused ring pyran compounds represented by Formula II, means a group that can be converted in one or more steps to the final or desired group. For purposes of non-limiting illustration: a precursor of a hydroxyl group (—OH) includes, but is not limited to, a carboxylic acid ester group (—OC(O)R where R is hydrogen or an optionally substituted hydrocarbyl); and a precursor of a carboxylic acid ester group (—OC(O)R) includes, but is not limited to, a hydroxyl group (—OH), which can be reacted, for example, with a carboxylic acid halide, such as acetic acid chloride (or acetyl chloride).

Various groups of the compounds and intermediates described previously and further herein, such as but not limited to the $R^1$, $R^2$, $R^3$, $R^4$, $R^5$, Q', Q''', B, B', and lengthening agent L groups of the compounds represented by Formulas I and II, and related formulas, can in each case be independently selected from hydrocarbyl and substituted hydrocarbyl.

As used herein and in the claims the term "hydrocarbyl" and similar terms, such as "hydrocarbyl substituent" and "hydrocarbyl group" means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl. Representative aryl groups include but are not limited to phenyl and naphthyl. Representative heteroaryl groups include but are not limited to furanyl, pyranyl and pyridinyl. Representative aralkyl groups include but are not limited to benzyl, and phenethyl.

The term "substituted hydrocarbyl" as used herein and in the claims means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl), and amine groups, such as —N($R_{11}$')($R_{12}$') where $R_{11}$' and $R_{12}$' are each independently selected from hydrogen, hydrocarbyl and substituted hydrocarbyl, or $R_{11}$' and $R_{12}$' together form a cyclic ring optionally including at least one heteroatom (e.g., —O—, —Si— and/or —S—).

The term "substituted hydrocarbyl" is inclusive of halohydrocarbyl (or halo substituted hydrocarbyl) substituents. The term "halohydrocarbyl" as used herein and in the claims, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom being replaced by a halogen atom (e.g., a fluoromethyl group) to full halogenation (perhalogenation) in which all replaceable hydrogen atoms on the hydrocarbyl group have been replaced by a halogen atom (e.g., trifluoromethyl or perfluoromethyl). Correspondingly, the term "perhalohydrocarbyl group" as used herein and in the claims means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which various groups and substituents, such as $R^1$, $R^2$, $R^3$, $R^4$, $R^5$, Q', Q''' and L, can each be selected, can in each case be independently and optionally interrupted with at least one of —O—, —S—, —C(O)—, —C(O)O—, —S(O)—, —S($O_2$)—, —N=N—, —N($R_{11}$')—, and —Si($OR_{14}$)$_u$($R_{14}$)$_v$—. As used herein and in the claims, by interrupted with at least one of —O—, —S—, —C(O)—, —C(O)O—, —S(O)—, —S($O_2$)—, —N=N—, —N($R_{11}$')—, and —Si($OR_{14}$)$_u$($R_{14}$)$_v$—, means that at least one carbon of, but less than all of the carbons of, the hydrocarbyl group or substituted hydrocarbyl group, is in each case independently replaced with one of the recited divalent linking groups. The hydrocarbyl and substituted hydrocarbyl groups can be interrupted with two or more of the above recited linking groups, which can be adjacent to each other or separated by one or more carbons.

As used herein and in the claims, unless otherwise indicated, left-to-right representations of linking groups, such as divalent linking groups, are inclusive of other appropriate orientations, such as, right-to-left orientations. For purposes of non-limiting illustration, the left-to-right representation of the divalent linking group —C(O)O—, is inclusive of the right-to-left representation thereof, —O(O)C—.

As used herein and in the claims, recitations of "linear or branched" or "linear, branched or cyclic" groups, such as linear or branched alkyl, or linear, branched or cyclic alkyl, are herein understood to include: a methylene group or a methyl group; groups that are linear, such as linear $C_2$-$C_{25}$ alkyl groups; groups that are appropriately branched, such as branched $C_3$-$C_{25}$ alkyl groups; and groups that are appropriately cyclic, such as $C_3$-$C_{25}$ cycloalkyl (or cyclic $C_3$-$C_{25}$ alkyl) groups.

With some embodiments of the present invention there is provided a thermally reversible, photochromic compound having a Q' or Q''' group at the position described previously and further herein, and optionally one or more Lengthening groups L, as further described hereinafter. Other non-limiting embodiments provide a photochromic compound adapted to have at least a first state and a second state, in which the thermally reversible, photochromic compound has an average absorption ratio greater than 2.3 in at least one state as determined according to the CELL METHOD, which is described in detail below. Further, according to various non-limiting embodiments, the thermally reversible, photochromic compound has an average absorption ratio greater than 2.3 in an activated state as determined according to the CELL METHOD. As used herein, the term "photochromic compound" (PC) refers to one or more photochromic compounds, including, but not limited to the photochromic compounds of the present invention, such as represented by Formula II. As used herein with respect to photochromic compounds, the term "activated state" refers to the photochromic compound when exposed to sufficient actinic radiation to cause the at least a portion of the photochromic compound to switch states. Further, as used herein the term "compound" means a substance formed by the union of two or more elements, components, ingredients, or parts and includes, without limitation, molecules and macromolecules (for example polymers or oligomers) formed by the union of two or more elements, components, ingredients, or parts.

In general, the CELL METHOD of measuring average absorption ratio of a photochromic compound involves obtaining an absorption spectrum for the photochromic compound, in an activated or unactived state, in each of two orthogonal polarization directions while the photochromic compound is at least partially aligned in an aligned liquid crystal medium that is contained within a cell assembly. More specifically, the cell assembly comprises two opposing glass substrates that are spaced apart by 20 microns+/−1 micron. The substrates are sealed along two opposite edges to form the cell. The inner surface of each of the glass substrates is coated with a polyimide coating, the surface of which has been at least partially ordered by rubbing. Alignment of the photochromic compound is achieved by introducing the photochromic compound and a liquid crystal medium into the cell assembly and allowing the liquid crystal medium to align with the rubbed polyimide surface. Because the photochromic compound is contained within the liquid crystal medium, alignment of the liquid crystal medium causes the photochromic compound to be aligned. It will be appreciated by those skilled in the art that the choice of the liquid crystal medium and the temperature used during testing can affect the measured absorption ratio. Accordingly, as set forth in more detail in the Examples, for purposes of the CELL METHOD, absorption ratio measurements are taken at room temperature (73° F.+/−0.5° F. or better) and the liquid crystal medium is Licristal® E7 (which is reported to be a mixture of cyanobiphenyl and cyanoterphenyl liquid crystal compounds).

Once the liquid crystal medium and the photochromic compound are aligned, the cell assembly is placed on an optical bench (which is described in more detail in the Examples). To obtain the average absorption ratio in the activated state, activation of the photochromic compound is achieved by exposing the photochromic compound to UV radiation for a time sufficient to reach a saturated or near saturated state (that is, a state wherein the absorption properties of the photochromic compound do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the cell is measured at each time interval for all of the wavelengths tested and the unactivated absorbance (i.e., the absorbance of the cell with the liquid crystal material and the unactivated photochromic compound) over the same range of wavelengths is subtracted to obtain absorption spectra for the photochromic compound in each of the 0° and 90° polarization planes to obtain an average difference absorption spectrum in each polarization plane for the photochromic compound in the saturated or near-saturated state.

For purposes of non-limiting illustration and with reference to FIG. 1, there is shown the average difference absorption spectrum (generally indicated 10) in one polarization plane that was obtained for a photochromic compound according to one non-limiting embodiment disclosed herein. The average absorption spectrum (generally indicated 11) is the average difference absorption spectrum obtained for the same photochromic compound in the orthogonal polarization plane.

Based on the average difference absorption spectra obtained for the photochromic compound, the average absorption ratio for the photochromic compound is obtained as follows. The absorption ratio of the photochromic compound at each wavelength in a predetermined range of wavelengths corresponding to $\lambda_{max\text{-}vis}$+/−5 nanometers (generally indicated as 14 in FIG. 1), wherein $\lambda_{max\text{-}vis}$ is the wavelength at which the photochromic compound had the highest average absorbance in any plane, is calculated according to the following equation:

$$AR_{\lambda i} = Ab^1_{\lambda i}/Ab^2_{\lambda i} \qquad \text{Eq. 1}$$

wherein, $AR_{\lambda i}$ is the absorption ratio at wavelength $\lambda i$, $Ab^1_{\lambda i}$ is the average absorption at wavelength $\lambda i$ in the polarization direction (i.e., 0° or 90°) having the higher absorbance, and $Ab^2_{\lambda i}$ is the average absorption at wavelength $\lambda i$ in the remaining polarization direction. As previously discussed, the "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average absorption ratio ("AR") for the photochromic compound is then calculated by averaging the individual absorption ratios obtained for the wavelengths within the predetermined range of wavelengths (i.e., $\lambda_{max\text{-}vis}$+/−5 nanometers) according to the following equation:

$$AR = (\Sigma AR_{\lambda i})/n_i \qquad \text{Eq. 2}$$

wherein, AR is average absorption ratio for the photochromic compound, $AR_{\lambda i}$ are the individual absorption ratios (as determined above in Eq. 1) for each wavelength within the predetermined the range of wavelengths (i.e., $\lambda_{max\text{-}vis}$+/−5 nanometers), and $n_i$ is the number of individual absorption ratios averaged.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. However, as previously discussed, generally conventional thermally reversible photochromic compounds do not strongly demonstrate dichroism.

As discussed above, non-limiting embodiments disclosed herein provide a thermally reversible photochromic compound having an average absorption ratio greater than 1.5 in at least one state as determined according to CELL METHOD and/or a thermally reversible photochromic compound that can be used as an intermediate in the preparation of a photochromic compound having an absorption ratio greater than 1.5. Thus, the thermally reversible photochromic compound according to this non-limiting embodiment can display useful photochromic properties and/or useful photochromic and dichroic properties. That is, the thermally reversible, photochromic compound can be a thermally reversible, photochromic and/or photochromic-dichroic compound. As used herein with respect to the photochromic compounds described herein, the term "photochromic-dichroic" means displaying both photochromic and dichroic properties under certain conditions, which properties are at least detectable by instrumentation.

In accordance with other non-limiting embodiments, the thermally reversible photochromic compounds can be thermally reversible photochromic-dichroic compounds having an average absorption ratio ranging from 4 to 20, from 3 to 30, or from 2.0 to 50 in at least one state as determined according to CELL METHOD. It will be appreciated by those skilled in the art that the higher the average absorption ratio of the photochromic compound the more linearly polarizing the photochromic compound will be. Therefore, according to various non-limiting embodiments, the thermally reversible photochromic compounds can have any average absorption ratio required to achieve a desired level of linear polarization.

Another non-limiting embodiment provides a thermally reversible, photochromic compound that is free of oxazines and adapted to have at least a first state and a second state, wherein the photochromic compound has an average absorption ratio of at least 1.5 in at least one state as determined according to CELL METHOD. Further, according to this non-limiting embodiment, the average absorption ratio can range from 1.5 to 50 in at least one state as determined according to CELL METHOD.

The groups and substituents of the compounds of the present invention, such as those represented by Formulas I and II, and related compounds as will be described in further detail herein, and the compounds and intermediates used in their preparation, are described in further detail as follows.

Ring-A of the compounds of the present invention, such as the compounds represented by Formula I and Formula II, can in each case be independently selected from unsubstituted aryl, substituted aryl, unsubstituted fused ring aryl, substituted fused ring aryl, unsubstituted heteroaryl, and substituted heteroaryl. Typically, Ring-A, aside from the $(R^1)_i$— group, is selected from unsubstituted aryl, unsubstituted fused ring aryl, and unsubstituted heteroaryl (or aryl, fused ring aryl, and heteroaryl). Examples of aryl groups from which Ring-A can be selected include, but are not limited to, phenyl and biphenyl. Examples of fused ring aryl groups from which Ring-A can be selected include, but are not limited to, polycyclic aromatic hydrocarbons, such as naphthyl and anthracenyl. Examples of heteroaryl groups from which Ring-A can be selected include, but are not limited to, furanyl, pyranyl and pyridinyl.

The Q' and Q''' groups of the compounds of the present invention can with some embodiments each be independently selected from, halogen, —OH, —N$_3$, —CN, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$ and —C(O)NR$^a$R$^a$, in which each R$^a$ is independently selected from hydrogen, hydrocarbyl and substituted hydrocarbyl each optionally and independently interrupted with divalent groups as described previously herein. With some embodiments, for Q' and Q''', each R$^a$ group is independently selected from hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl, and R$^b$ is selected from a perfluorinated alkyl group having from 1 to 18 carbon atoms. Examples of perfluorinated alkyl groups include, but are not limited to, perfluoromethyl (—CF$_3$), perfluoro ethyl (—CF$_2$CF$_3$), perfluoropropy, including perfluoro-n-propyl, perfluoro-iso-propyl, perfluorobutyl including isomers thereof, such as perfluoro-n-butyl and perfluoro-t-butyl, and perfluorooctyl, including isomers thereof.

With some further embodiments of the present invention, for Q' and Q''', each R$^a$ group is independently selected from hydrogen and an alkyl group having from 1 to 6 carbon atoms, and R$^b$ is selected from a perfluorinated alkyl group having from 1 to 6 carbon atoms.

The Q' and Q''' groups, with some embodiments, can each be independently selected from bromo, fluoro, chloro, —N$_3$, —NR$^a$R$^a$, —N(R$^a$)C(O)Q''', —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$, —C(O)NR$^a$R$^a$. Q' can also be lengthening agent L (as described further herein). Each R$^a$ group can be independently selected from hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl. Alternatively two R$^a$ groups can come together with —N and an additional hetero atom selected from N and O to form a heterocycloalkyl. The R$^b$ group can be selected from a perfluorinated alkyl group having from 1 to 18 carbon atoms. The Q'' group can be selected from —OR$^a$, —NR$^a$R$^a$, —C(O)OR$^a$, —SR$^a$, and hydrocarbyl or substituted hydrocarbyl, wherein the substituents are selected from —OH, —NR$^a$R$^a$, —C(O)OR$^a$, —SR$^a$.

With further embodiments, Q' and Q''' are each independently selected from bromo, chloro, —NR$^a$R$^a$, —C(O)R$^a$, and —C(O)OR$^a$. The Q' group can also be lengthening agent L. Each R$^a$ is independently selected from hydrogen and an alkyl group having from 1 to 6 carbon atoms. Alternatively, two R$^a$ groups come together with —N and an additional N atom to form a heterocycloalkyl. The R$^b$ group is selected from a perfluorinated alkyl group having from 1 to 6 carbon atoms.

With some embodiments of the present invention, Q''' is not selected from lengthening agent L.

The R$^5$ group of the indeno-fused ring compounds of the present invention, such as those represented by Formula I above, and Formula Ia (as will be described further herein), can be selected from hydrogen, —C(O)—R$^{13}$ or —S(O$_2$)R$^{13}$, in which R$^{13}$ is hydrocarbyl, or halohydrocarbyl. With some embodiments, R$^5$ is selected from hydrogen and —C(O)—R$^{13}$. Typically, R$^{13}$ can be selected from C$_1$-C$_{12}$ or C$_1$-C$_6$ alkyl groups or perhaloalkyl groups, such as perfluoroalkyl groups.

For the indeno-fused ring compounds, such as represented by Formula I, and the indeno-fused ring pyran compounds, such as represented by Formula II, of the present invention, R$^1$ for each i, and R$^2$ for each t, are each independently selected from: (a) —C(O)X$_{24}$; (b) —OX$_7$ and —N(X$_7$)$_2$; (c) —SX$_{11}$; (d) a nitrogen containing ring represented by Formula i, as will be described in further detail herein; (e) a group represented by Formula II and iii, as will be described in further detail herein; (f) or immediately adjacent $R^1$ groups, and immediately adjacent $R^2$ groups, in each case independently together form a group represented by Formula vii, viii, or ix, as will be described in further detail herein; (g) a lengthening agent L represented by Formula III as will be described in further detail herein; and (h) a group B, as will be described in further detail herein.

With some embodiments, $R^1$ for each i, and $R^2$ for each t, are each independently selected from, (a) —C(O)$X_{24}$, in which $X_{24}$ is chosen from a lengthening agent L (as will be described further herein), hydroxy, $C_1$-$C_{18}$ alkyl, $C_1$-$C_{18}$ alkoxy, phenyl that is unsubstituted or mono-substituted with $C_1$-$C_{18}$ alkyl or $C_1$-$C_{18}$ alkoxy, amino that is unsubstituted, mono- or di-substituted with at least one of $C_1$-$C_{18}$ alkyl, phenyl, benzyl, and naphthyl.

With some further embodiments, $R^1$ for each i, and $R^2$ for each t, are each independently selected from, (a) —C(O)$X_{24}$, in which $X_{24}$ is chosen from a lengthening agent L (as will be described further herein), hydroxy, $C_1$-$C_{12}$ alkyl, $C_1$-$C_{12}$ alkoxy, phenyl that is unsubstituted or mono-substituted with $C_1$-$C_6$ alkyl or $C_1$-$C_6$ alkoxy, amino that is unsubstituted, mono- or di-substituted with at least one of $C_1$-$C_6$ alkyl, phenyl, benzyl, and naphthyl.

In accordance with further embodiments, $R^1$ for each i, and $R^2$ for each t, are each independently selected from, (a) —C(O)$X_{24}$, in which $X_{24}$ is chosen from hydroxy, $C_1$-$C_6$ alkyl, $C_1$-$C_6$ alkoxy, phenyl that is unsubstituted or mono-substituted with $C_1$-$C_6$ alkyl or $C_1$-$C_6$ alkoxy, amino that is unsubstituted, mono- or di-substituted with at least one of $C_1$-$C_6$ alkyl, phenyl, benzyl, and naphthyl.

With some embodiments, $R^1$ for each i, and $R^2$ for each t, are each independently selected from, (b) —$OX_7$ and —N($X_7$)$_2$, in which each $X_7$ is independently chosen from four categories of groups (i), (ii), (iii), and (iv). With some embodiments, $X_7$ is chosen from, (i) hydrogen, a lengthening agent L (as will be described further herein), $C_1$-$C_{18}$ alkyl, $C_1$-$C_{18}$ acyl, phenyl($C_1$-$C_{18}$)alkyl, mono($C_1$-$C_{18}$)alkyl substituted phenyl($C_1$-$C_{18}$)alkyl, mono($C_1$-$C_{18}$)alkoxy substituted phenyl($C_1$-$C_{18}$)alkyl; $C_1$-$C_{16}$ alkoxy($C_1$-$C_{18}$)alkyl; $C_3$-$C_{10}$ cycloalkyl; mono($C_1$-$C_{18}$)alkyl substituted $C_3$-$C_{10}$ cycloalkyl, $C_1$-$C_{18}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{18}$ alkyl, and $C_1$-$C_{18}$ alkoxy. Each $X_7$ can independently be chosen from, (ii) —CH($X_8$)$X_9$, wherein $X_8$ is chosen from hydrogen, a lengthening agent L, or $C_1$-$C_{18}$ alkyl, and $X_9$ is chosen from a lengthening agent L, —CN, —$CF_3$, or —$COOX_{10}$, wherein $X_{10}$ is chosen from hydrogen, a lengthening agent L (as will be described further herein), or $C_1$-$C_{18}$ alkyl. Each $X_7$ can independently be chosen from, (iii) —C(O)$X_6$, in which $X_6$ is chosen from at least one of, hydrogen, a lengthening agent L (as will be described further herein), $C_1$-$C_{18}$ alkoxy, phenoxy that is unsubstituted, mono- or di-substituted with $C_1$-$C_{18}$ alkyl or $C_1$-$C_{18}$ alkoxy, an aryl group that is unsubstituted, mono- or di-substituted with $C_1$-$C_{18}$ alkyl or $C_1$-$C_{18}$ alkoxy, an amino group that is unsubstituted, mono- or di-substituted with $C_1$-$C_{18}$ alkyl, and a phenylamino group that is unsubstituted, mono- or di-substituted with $C_1$-$C_{18}$ alkyl or $C_1$-$C_{18}$ alkoxy. In addition, each $X_7$ can independently be chosen from, (iv) tri($C_1$-$C_{18}$)alkylsilyl, tri($C_1$-$C_{18}$)alkylsilyloxy, tri($C_1$-$C_{18}$)alkoxysilyl, tri($C_1$-$C_{18}$)alkoxysilyloxy, di($C_1$-$C_{18}$)alkyl($C_1$-$C_{18}$ alkoxy)silyl, di($C_1$-$C_{18}$)alkyl($C_1$-$C_{18}$ alkoxy)silyloxy, di($C_1$-$C_{18}$)alkoxy($C_1$-$C_{18}$ alkyl)silyl or di($C_1$-$C_{18}$)alkoxy($C_1$-$C_{18}$ alkyl)silyloxy.

With further embodiments of the present invention, $R^1$ for each i, and $R^2$ for each t, are each independently selected from, (b) —$OX_7$ and —N($X_7$)$_2$, in which each $X_7$ is independently chosen from, (i) hydrogen, a lengthening agent L, $C_1$-$C_{12}$ alkyl, $C_1$-$C_{12}$ acyl, phenyl($C_1$-$C_{12}$)alkyl, mono($C_1$-$C_{12}$)alkyl substituted phenyl($C_1$-$C_{12}$)alkyl, mono($C_1$-$C_{12}$) alkoxy substituted phenyl($C_1$-$C_{12}$)alkyl; $C_1$-$C_{12}$ alkoxy($C_1$-$C_{12}$)alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-substituted benzoyl, naphthoyl or mono-substituted naphthoyl, wherein each of said benzoyl and naphthoyl substituents are independently chosen from $C_1$-$C_6$ alkyl, and $C_1$-$C_6$ alkoxy. Each $X_7$ can also be independently selected from, (ii) —CH($X_8$)$X_9$, wherein $X_8$ is chosen from hydrogen, a lengthening agent L, or $C_1$-$C_{12}$ alkyl; and $X_9$ is chosen from a lengthening agent L, —CN, —$CF_3$, or —$COOX_{10}$, wherein $X_{10}$ is chosen from hydrogen, a lengthening agent L, or $C_1$-$C_{12}$ alkyl. Each $X_7$ can be further selected from, (iii) —C(O)$X_8$, wherein $X_6$ is chosen from at least one of, hydrogen, a lengthening agent L, $C_1$-$C_{12}$ alkoxy, phenoxy that is unsubstituted, mono- or di-substituted with $C_1$-$C_{12}$ alkyl or $C_1$-$C_{12}$ alkoxy, an aryl group that is unsubstituted, mono- or di-substituted with $C_1$-$C_6$ alkyl or $C_1$-$C_6$ alkoxy, an amino group that is unsubstituted, mono- or di-substituted with $C_1$-$C_6$ alkyl, and a phenylamino group that is unsubstituted, mono- or di-substituted with $C_1$-$C_6$ alkyl or $C_1$-$C_6$ alkoxy.

With additional embodiments of the present invention, $R^1$ for each i, and $R^2$ for each t, are each independently selected from, (b) —$OX_7$ and —N($X_7$)$_2$, in which each $X_7$ is independently chosen from, (i) hydrogen, $C_1$-$C_6$ alkyl, $C_1$-$C_6$ acyl, phenyl($C_1$-$C_6$)alkyl, mono($C_1$-$C_8$)alkyl substituted phenyl($C_1$-$C_8$)alkyl, mono($C_1$-$C_6$)alkoxy substituted phenyl($C_1$-$C_6$)alkyl; $C_1$-$C_6$ alkoxy($C_1$-$C_8$)alkyl; $C_{3-5}$ cycloalkyl; mono($C_1$-$C_6$)alkyl substituted $C_{3-5}$ cycloalkyl, $C_1$-$C_6$ haloalkyl, allyl, benzoyl, mono-substituted benzoyl, naphthoyl or mono-substituted naphthoyl, wherein each of said benzoyl and naphthoyl substituents are independently chosen from $C_1$-$C_3$ alkyl, and $C_1$-$C_3$ alkoxy. Each $X_7$ can also be selected from, (ii) —CH($X_8$)$X_9$, wherein $X_8$ is chosen from hydrogen or $C_1$-$C_6$ alkyl; and $X_9$ is chosen from —CN, —$CF_3$, or —$COOX_{10}$, wherein $X_{10}$ is chosen from hydrogen or $C_1$-$C_6$ alkyl. Each $X_7$ can also be further selected from, (iii) —C(O) $X_6$, wherein $X_6$ is chosen from hydrogen, $C_1$-$C_{12}$ alkoxy, phenoxy that is unsubstituted, mono- or di-substituted with $C_1$-$C_6$ alkyl or $C_1$-$C_6$ alkoxy, an aryl group that is unsubstituted, mono- or di-substituted with $C_1$-$C_3$ alkyl or $C_1$-$C_3$ alkoxy, an amino group that is unsubstituted, mono- or di-substituted with $C_1$-$C_3$ alkyl, and a phenylamino group that is unsubstituted, mono- or di-substituted with $C_1$-$C_3$ alkyl or $C_1$-$C_3$ alkoxy.

With some embodiments, $R^1$ for each i, and $R^2$ for each t, are each independently selected from, (c) —$SX_{11}$, wherein $X_{11}$ is chosen from hydrogen, a lengthening agent L, $C_1$-$C_{18}$ alkyl, $C_1$-$C_{18}$ haloalkyl, an aryl group that is unsubstituted, or mono- or di-substituted with $C_1$-$C_{18}$ alkyl, $C_1$-$C_{18}$ alkoxy, or halogen. The $X_{11}$ group of —$SX_{11}$ can also be selected from $C_1$-$C_6$ alkyl, $C_1$-$C_6$ haloalkyl, an aryl group (such as a phenyl group) that is unsubstituted, or mono- or di-substituted with $C_1$-$C_6$ alkyl, $C_1$-$C_6$ alkoxy, or halogen, such as chloro, bromo or fluoro.

With some embodiments, $R^1$ for each i, and $R^2$ for each t, are each independently selected from, (d) a nitrogen containing ring represented by the following Formula i:

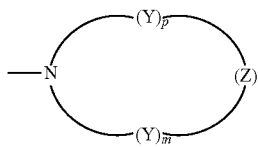

i

With reference to Formula i, each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —S(O)—, —SO$_2$—, —NH—, —N(R$_{13}$')—, or —N(aryl)-, wherein each R$_{13}$' is independently a lengthening group L, or C$_1$-C$_{20}$ alkyl (e.g., C$_1$-C$_{12}$ alkyl or C$_1$-C$_6$ alkyl), each aryl is independently phenyl or naphthyl, m is an integer 1, 2 or 3, and p is an integer 0, 1, 2, or 3, provided that when p is 0, Z is —Y—.

With further embodiments, R$^1$ for each i, and R$^2$ for each t, are each independently selected from, (e) a group represented by the following Formula ii or Formula iii,

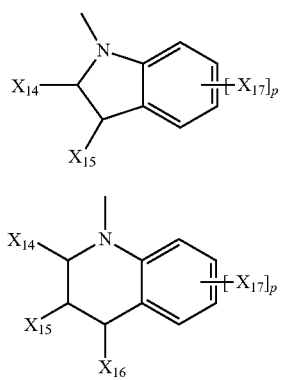

ii iii

With reference to Formulas ii and iii, X$_{14}$, X$_{15}$, and X$_{16}$ are independently chosen for each occurrence from hydrogen, a lengthening agent L, C$_1$-C$_{18}$ alkyl, phenyl or naphthyl, or X$_{14}$ and X$_{15}$ together form a ring of 5 to 8 carbon atoms, p is an integer chosen from 0, 1, or 2, and X$_{17}$ is independently chosen for each occurrence from a lengthening agent L, C$_1$-C$_{18}$ alkyl, C$_1$-C$_{18}$ alkoxy, or halogen.

In accordance with additional embodiments, R$^1$ for each i, and R$^2$ for each t, are each independently selected from, a group represented by the Formula II or Formula iii, as shown above, in which X$_{14}$, X$_{15}$, and X$_{16}$ are independently chosen for each occurrence from hydrogen, a lengthening agent L, C$_1$-C$_{12}$ alkyl, phenyl or naphthyl, or X$_{14}$ and X$_{15}$ together form a ring of 5 to 7 carbon atoms; p is an integer chosen from 0, 1, or 2, and X$_{17}$ is independently chosen for each occurrence from a lengthening agent L, C$_1$-C$_{12}$ alkyl, C$_1$-C$_{12}$ alkoxy, or halogen.

In accordance with further embodiments, R$^1$ for each i, and R$^2$ for each t, are each independently selected from, a group represented by the Formula II or Formula iii, as shown above, in which X$_{14}$, X$_{15}$, and X$_{16}$ are independently chosen for each occurrence from hydrogen, C$_1$-C$_6$ alkyl, or phenyl or X$_{14}$ and X$_{15}$ together form a ring of 5 to 7 carbon atoms; p is an integer chosen from 0, 1, or 2, and X$_{17}$ is independently chosen for each occurrence from C$_1$-C$_6$ alkyl, C$_1$-C$_6$ alkoxy, or halogen.

According to some embodiments, immediately adjacent R$^1$ groups, and immediately adjacent R$^2$ groups, in each case independently together form a group represented by the following Formulas vii, viii, or ix,

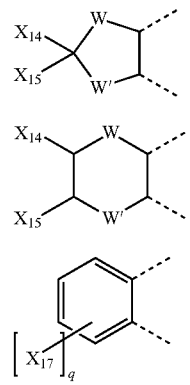

vii viii ix

With reference to Formulas vii and viii, W and W' W and W' are independently chosen for each occurrence from —O—, —N(X$_7$)—, —C(X$_{14}$)—, and —C(X$_{17}$)—. With further reference to Formulas vii, viii, and ix, X$_{14}$ and X$_{15}$ are independently chosen for each occurrence from hydrogen, a lengthening agent L, C$_1$-C$_{18}$ alkyl, phenyl or naphthyl, or X$_{14}$ and X$_{15}$ together form a ring of 5 to 8 carbon atoms; and X$_{17}$ is independently chosen for each occurrence from a lengthening agent L, C$_1$-C$_{18}$ alkyl, C$_1$-C$_{18}$ alkoxy, or halogen. With reference to Formula ix, q is an integer chosen from 0, 1, 2, 3, and 4.

In the case of some embodiments of the present invention, the nitrogen containing ring represented by Formula i, can be alternatively represented by the following Formulas-(XI) and -(XII).

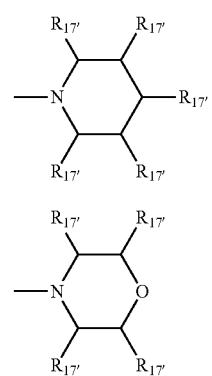

Formula-(XI)

Formula-(XII)

In the case of Formulas-(XI) and -(XII), R$_{17'}$ is in each instance independently selected from hydrogen or alkyl, such as C$_1$-C$_6$ alkyl, or optionally substituted aryl, such as optionally substituted phenyl, and correspondingly, the nitrogen containing ring is selected from substituted or unsubstituted piperidenyl (e.g., Formula-XI), and/or substituted or unsubstituted morpholinyl (e.g., Formula-XII).

In accordance with further embodiments of the present invention, immediately adjacent R$^1$ groups, and immediately adjacent R$^2$ groups, in each case independently together form a group represented by Formulas vii, viii, or ix, as shown above, in which W and W' are independently chosen for each occurrence from —O—, —N(X$_7$)—, —C(X$_{14}$)—, and —C(X$_{17}$)—. The X$_{14}$ and X$_{15}$ groups are each independently chosen for each occurrence from hydrogen, a lengthening agent L, C$_1$-C$_{12}$ alkyl, phenyl or naphthyl, or X$_{14}$ and X$_{15}$ together form a ring of 5 to 7 carbon atoms; and X$_{17}$ is independently chosen for each occurrence from a lengthening agent L, C$_1$-C$_{12}$ alkyl, C$_1$-C$_{12}$ alkoxy, or halogen. In addition, q is an integer chosen from 0 to 3.

In accordance with additional further embodiments of the present invention, immediately adjacent R$^1$ groups, and immediately adjacent R$^2$ groups, in each case independently together form a group represented by Formulas vii, viii, or ix, as shown above, in which W and W' are independently chosen for each occurrence from —O—, —N(X$_7$)—, —C(X$_{14}$)—, and —C(X$_{17}$)—. The X$_{14}$ and X$_{15}$ groups are independently chosen for each occurrence from hydrogen, C$_1$-C$_6$ alkyl, phenyl or naphthyl, or X$_{14}$ and X$_{15}$ together form a ring of 5 to 7 carbon atoms; and X$_{17}$ is independently chosen for each occurrence from C$_1$-C$_6$ alkyl, C$_1$-C$_6$ alkoxy, or halogen. In addition, q is an integer chosen from 0 to 3.

The various groups of the indeno-fused ring compounds and indeno-fused ring pyran compounds of the present invention, including, but not limited to, R$^1$ for each i, R$^2$ for each t, Q', and Q''', can each independently include or be selected from, a lengthening agent L represented by the following Formula III,

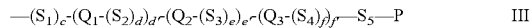

As used herein and the claims the term "lengthening agent L" and similar terms, such as lengthening agent and lengthening group, means in each case, a group that is independently selected from a group represented by Formula III as shown above, and as described in further detail as follows.

As used herein, the term "attached" means directly bonded to or indirectly bonded to through another group. Thus, for example, according to various non-limiting embodiments disclosed herein, L can be directly bonded to the compounds of the present invention as a substituent on the compound, or L can be a substituent on another group (such as a group represented by R$^1$) that is directly bonded to the compound (i.e., L is indirectly bonded to the compound). Although not limiting herein, according to various non-limiting embodiments, L can be attached to the compound so as to extend or lengthen the compound in an activated state such that the absorption ratio of the extended compound (e.g., the photochromic compound) is enhanced as compared to the compound in the absence of a lengthening agent. Although not limiting herein, according to various non-limiting embodiments, the location of attachment of L on the compound can be chosen such that L lengthens the compound in at least one of a direction parallel to or a direction perpendicular to a theoretical transitional dipole moment of the activated form of the compound. Regarding the position of L, it can be subsequently attached to the compound at the location of the Q' or Q''' group. The compounds of the present invention can have at least one Q' or Q''' group at the position(s) indicated, and optionally one or more L groups. As used herein the term "theoretical transitional dipole moment" refers to transient dipolar polarization created by interaction of electromagnetic radiation with the molecule. See, for example, IUPAC Compendium of Chemical Technology, 2$^{nd}$ Ed., International Union of Pure and Applied Chemistry (1997).

With some embodiments, each Q$_1$, Q$_2$, and Q$_3$ of Formula III is independently chosen for each occurrence from, a divalent group chosen from, an unsubstituted or a substituted aromatic group, an unsubstituted or a substituted alicyclic group, an unsubstituted or a substituted heterocyclic group, and mixtures thereof. The substituents the Q$_1$, Q$_2$, and Q$_3$ can be chosen from, a group represented by P, liquid crystal mesogens, halogen, poly(C$_1$-C$_{18}$ alkoxy), C$_1$-C$_{18}$ alkoxycarbonyl, C$_1$-C$_{18}$ alkylcarbonyl, C$_1$-C$_{18}$ alkoxycarbonyloxy, aryloxycarbonyloxy, perfluoro(C$_1$-C$_{18}$)alkoxy, perfluoro(C$_1$-C$_{18}$)alkoxycarbonyl, perfluoro(C$_1$-C$_{18}$)alkylcarbonyl, perfluoro(C$_1$-C$_{18}$)alkylamino, di-(perfluoro(C$_1$-C$_{18}$)alkyl)amino, perfluoro(C$_1$-C$_{18}$)alkylthio, C$_1$-C$_{18}$ alkylthio, C$_1$-C$_{18}$ acetyl, C$_3$-C$_{10}$ cycloalkyl, C$_3$-C$_{10}$ cycloalkoxy, a straight-chain or branched C$_1$-C$_{18}$ alkyl group that is mono-substituted with cyano, halo, or C$_1$-C$_{18}$ alkoxy, or poly-substituted with halo, and a group comprising one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M.

The subscripts c, d, e, and f of Formula-III are each independently an integer selected from 0 to 20, inclusive of the recited values. The S$_1$, S$_2$, S$_3$, S$_4$, and S$_5$ groups of Formula-III are each independently for each occurrence a spacer unit chosen from the following categories (1), (2) and (3). The spacer units of category (1) include, optionally substituted alkylene, optionally substituted haloalkylene, —Si(Z')$_2$(CH$_2$)$_g$—, and

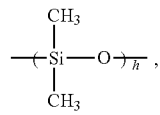

wherein each Z' is independently selected from hydrogen, C$_1$-C$_{18}$ alkyl, C$_3$-C$_{10}$ cycloalkyl, and aryl; g for each occurrence is independently chosen from an integer from 1 to 20; h for each occurrence is independently chosen from an integer from 1 to 16; and said substituents for the alkylene and haloalkylene are independently selected from C$_1$-C$_{18}$ alkyl, C$_3$-C$_{10}$ cycloalkyl and aryl. The spacer units of category (2) include, —N(Z)—, —C(Z)=C(Z)—, —C(Z)=N—, —C(Z')$_2$—C(Z')$_2$— or a single bond, wherein Z is independently chosen for each occurrence from hydrogen, C$_1$-C$_{18}$ alkyl, C$_3$-C$_{10}$ cycloalkyl and aryl, and Z' is independently chosen for each occurrence from C$_1$-C$_{18}$ alkyl, C$_3$-C$_{10}$ cycloalkyl and aryl. The spacer units of category (3) include, —O—, —C(O)—, —C≡C—, —N=N—, —S—, —S(O)—, —S(O)(O)—, —(O)S(O)—, —(O)S(O)O—, —O(O)S(O)O—, or straight-chain or branched C$_1$-C$_{24}$ alkylene residue, said C$_1$-C$_{24}$ alkylene residue being unsubstituted, mono-substituted by cyano or halo, or poly-substituted by halo. With regard to the spacer units from which S$_1$, S$_2$, S$_3$, S$_4$, and S$_5$ can be chosen, there is the proviso that when two spacer units comprising heteroatoms are linked together the spacer units are linked so that heteroatoms are not directly linked to each other. With regard to the spacer units from which S$_1$, S$_2$, S$_3$, S$_4$, and S$_5$ can be chosen, there is the further proviso that when S$_1$ is linked to a compound of the present invention, such as Formula I, and S$_5$ is linked to P, S$_1$ and S$_5$ are in each case so linked such that two heteroatoms are not directly linked to each other.

With further reference to Formula-III, P is chosen from: hydroxy, amino, C$_2$-C$_{18}$ alkenyl, C$_2$-C$_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl ($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl ($C_1$-$C_{18}$)alkoxy($C_1$-$C_{18}$)alkyl, polyethyleneoxy, polypropyleneoxy, ethylenyl, acryloyl, acryloyloxy($C_1$-$C_{18}$) alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound.

The subscripts d', e' and f' of Formula-III can each independently chosen from 0, 1, 2, 3, and 4, provided that the sum of d'+e'+f' is at least 1 in some embodiments, or at least 2 in some further embodiments, or at least 3 in some additional embodiments.

According to various non-limiting embodiments disclosed herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

According to further non-limiting embodiments, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls.

According to another non-limiting embodiment, P can be chosen from a steroid radical, for example and without limitation, a cholesterolic compound.

With some embodiments of the present invention, $R^1$ for each i, and $R^2$ for each t, are each independently selected from a group B. With some embodiments, the group B can be selected from (i) hydrogen, $C_1$-$C_{18}$ alkyl, $C_2$-$C_{18}$ alkylidene, $C_2$-$C_{18}$ alkylidyne, vinyl, $C_3$-$C_{10}$ cycloalkyl, $C_1$-$C_{18}$ haloalkyl, allyl, halogen, and benzyl that is unsubstituted or mono-substituted with at least one of $C_1$-$C_{18}$ alkyl and $C_1$-$C_{18}$ alkoxy. With further embodiments, the group B can be selected from (i) $C_1$-$C_{12}$ alkyl, $C_3$-$C_7$ cycloalkyl, $C_1$-$C_{12}$ haloalkyl and benzyl that is unsubstituted or mono-substituted with at least one of $C_1$-$C_6$ alkyl and $C_1$-$C_6$ alkoxy. With still further embodiments, the group B can be selected from (i) $C_1$-$C_6$ alkyl, $C_3$-$C_5$ cycloalkyl, $C_1$-$C_6$ haloalkyl and benzyl that is unsubstituted or mono-substituted with at least one of $C_1$-$C_3$ alkyl and $C_1$-$C_3$ alkoxy.

In accordance with embodiments of the present invention, the group B can be selected from (ii) phenyl that is mono-substituted at the para position with at least one substituent chosen from: $C_1$-$C_{18}$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_{18}$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material.

With some further embodiments, group B can be selected from (iii) —CH(CN)$_2$ and —CH(COOX$_1$)$_2$, wherein $X_1$ is chosen from at least one of hydrogen, a lengthening agent L, $C_1$-$C_{18}$ alkyl that is unsubstituted or mono-substituted with phenyl, phenyl($C_1$-$C_{18}$)alkyl that is mono-substituted with $C_1$-$C_{18}$ alkyl, $C_1$-$C_{18}$ haloalkyl or $C_1$-$C_{18}$ alkoxy, and an aryl group that is unsubstituted, mono- or di-substituted, wherein each aryl substituent is independently chosen from $C_1$-$C_{18}$ alkyl and $C_1$-$C_{18}$ alkoxy, and lengthening agent L. With some additional embodiments, the group B can be selected from —CH(CN)$_2$ and —CH(COOX$_1$)$_2$, wherein $X_1$ is chosen from at least one of hydrogen, a lengthening agent L, $C_1$-$C_{12}$ alkyl that is unsubstituted or mono-substituted with phenyl, phenyl ($C_1$-$C_6$)alkyl that is mono-substituted with $C_1$-$C_6$ alkyl or $C_1$-$C_6$ alkoxy, and an aryl group that is unsubstituted, mono- or di-substituted, wherein each aryl substituent is independently chosen from $C_1$-$C_6$ alkyl and $C_1$-$C_6$ alkoxy; and lengthening agent L. With further additional embodiments, group B can be selected from —CH(CN)$_2$ and —CH (COOX$_1$)$_2$, wherein $X_1$ is chosen from hydrogen, $C_1$-$C_6$ alkyl that is unsubstituted or mono-substituted with phenyl, phenyl ($C_1$-$C_3$)alkyl that is mono-substituted with $C_1$-$C_3$ alkyl or $C_1$-$C_3$ alkoxy, and an aryl group that is unsubstituted, mono- or di-substituted, wherein each aryl substituent is independently chosen from $C_1$-$C_3$ alkyl and $C_1$-$C_3$ alkoxy; and lengthening agent L.

With some embodiments, group B can be selected from (iv) —CH($X_2$)($X_3$). The $X_2$ group can be chosen from at least one of hydrogen, a lengthening agent L, $C_1$-$C_{18}$ alkyl, and an aryl group that is unsubstituted, mono- or di-substituted, wherein each aryl substituent is independently chosen from $C_1$-$C_{18}$ alkyl and $C_1$-$C_{18}$ alkoxy. The $X_3$ group can be chosen from at least one of —COOX$_1$, —COX$_4$, and —CH$_2$OX$_5$, wherein, $X_4$ is chosen from at least one of morpholino, piperidino, amino that is unsubstituted, mono- or di-substituted with $C_1$-$C_{18}$ alkyl, and an unsubstituted, mono- or di-substituted group chosen from phenylamino and diphenylamino, wherein each substituent is independently chosen from $C_1$-$C_{18}$ alkyl or $C_1$-$C_{18}$ alkoxy; and $X_5$ is chosen from hydrogen, a lengthening agent L, —C(O)$X_2$, $C_1$-$C_{18}$ alkyl that is unsubstituted or mono-substituted with ($C_1$-$C_{18}$)alkoxy or phenyl, phenyl($C_1$-$C_{18}$)alkyl that is mono-substituted with ($C_1$-$C_{18}$)alkoxy, and an aryl group that is unsubstituted, mono- or di-substituted, wherein each aryl substituent is independently chosen from $C_1$-$C_{18}$ alkyl and $C_1$-$C_{18}$ alkoxy.

With some further embodiments, group B can be selected from —CH($X_2$)($X_3$). The $X_2$ group can be chosen from at least one of a lengthening agent L, $C_1$-$C_{12}$ alkyl, and an aryl group that is unsubstituted, mono- or di-substituted, wherein each aryl substituent is independently chosen from $C_1$-$C_8$ alkyl and $C_1$-$C_6$ alkoxy. The $X_3$ group can be chosen from at least one of —COO$X_1$, —CO$X_1$, —CO$X_4$, and —CH$_2$O$X_5$, wherein: $X_4$ is chosen from at least one of morpholino, piperidino, amino that is unsubstituted, mono- or di-substituted with $C_1$-$C_6$ alkyl, and an unsubstituted, mono or di-substituted group chosen from phenylamino and diphenylamino, wherein each substituent is independently chosen from $C_1$-$C_6$ alkyl or $C_1$-$C_6$ alkoxy; and $X_5$ is chosen from hydrogen, a lengthening agent L, —C(O)$X_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$)alkoxy, and an aryl group that is unsubstituted, mono- or di-substituted, wherein each aryl substituent is independently chosen from $C_1$-$C_6$ alkyl and $C_1$-$C_6$ alkoxy.

With some further additional embodiments, group B can be selected from —CH($X_2$)($X_3$). The $X_2$ group can be chosen from at least one of a lengthening agent L, $C_1$-$C_8$ alkyl, and an aryl group that is unsubstituted, mono- or di-substituted, wherein each aryl substituent is independently chosen from $C_1$-$C_3$ alkyl and $C_1$-$C_3$ alkoxy. The $X_3$ is chosen from at least one of —COO$X_1$, —CO$X_4$, and —CH$_2$O$X_5$, wherein: $X_4$ group can be chosen from at least one of morpholino, piperidino, amino that is unsubstituted, mono- or di-substituted with $C_1$-$C_3$ alkyl, and an unsubstituted, mono or di-substituted group chosen from phenylamino and diphenylamino, wherein each substituent is independently chosen from $C_1$-$C_3$ alkyl or $C_1$-$C_3$ alkoxy; and $X_5$ is chosen from hydrogen, a lengthening agent L, —C(O)$X_2$, $C_1$-$C_6$ alkyl that is unsubstituted or mono-substituted with ($C_1$-$C_6$)alkoxy or phenyl, phenyl($C_1$-$C_{12}$)alkyl that is mono-substituted with ($C_1$-$C_6$)alkoxy, and an aryl group that is unsubstituted, mono- or di-substituted, wherein each aryl substituent is independently chosen from $C_1$-$C_3$ alkyl and $C_1$-$C_3$ alkoxy.

Group B can in some embodiments be selected from (v) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl. Each aryl and heteroaromatic group substituent can independently be chosen for each occurrence from: (1) a lengthening agent L; (2) —COO$X_1$ or —C(O)$X_6$; (3) aryl, halogen, haloaryl, $C_3$-$C_{10}$ cycloalkylaryl, and an aryl group that is mono- or di-substituted with $C_1$-$C_{18}$ alkyl or $C_1$-$C_{18}$ alkoxy; (4) $C_1$-$C_{18}$ alkyl, $C_3$-$C_{10}$ cycloalkyl, $C_3$-$C_{10}$ cycloalkyloxy($C_1$-$C_{18}$)alkyl, aryl($C_1$-$C_{18}$)alkyl, aryloxy($C_1$-$C_{18}$)alkyl, mono- or di-($C_1$-$C_{18}$)alkylaryl($C_1$-$C_{18}$)alkyl, mono- or di-($C_1$-$C_{18}$)alkoxyaryl($C_1$-$C_{18}$)alkyl, $C_1$-$C_{18}$ haloalkyl, and mono($C_1$-$C_{18}$)alkoxy($C_1$-$C_{18}$)alkyl; (5) $C_1$-$C_{18}$ alkoxy, $C_3$-$C_{10}$ cycloalkoxy, cycloalkyloxy($C_1$-$C_{18}$)alkoxy, aryl($C_1$-$C_{18}$)alkoxy, aryloxy($C_1$-$C_{18}$)alkoxy, mono- or di-($C_1$-$C_{18}$)alkylaryl($C_1$-$C_{18}$)alkoxy, and mono- or di-($C_1$-$C_{18}$)alkoxyaryl($C_1$-$C_{18}$)alkoxy; (6) aminocarbonyl, aminocarbonyl($C_1$-$C_{18}$)alkylene, amino, mono- or di-alkylamino, diarylamino, piperazino, N—($C_1$-$C_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen; (7) —O$X_7$ or —N($X_7$)$_2$; (8) —S$X_{11}$; (9) a nitrogen containing ring represented by Formula i; (10) a group represented by Formula II or iii; and (11) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, $C_1$-$C_{18}$ alkyl, $C_1$-$C_{18}$ alkoxy, phenyl, hydroxy, amino or halogen.

Each aryl and heteroaromatic group substituent can additionally and independently be chosen for each occurrence from, (12) a group represented by Formula iv or Formula v,

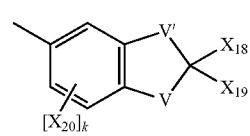

iv

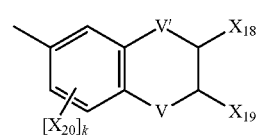

v

With reference to Formulas iv and v: (I) V' is independently chosen in each formula from —O—, —CH—, $C_1$-$C_8$ alkylene, and $C_3$-$C_{10}$ cycloalkylene; (II) V is independently chosen in each formula from —O— or —N($X_{21}$)—, wherein $X_{21}$ is hydrogen, a lengthening agent L, $C_1$-$C_{18}$ alkyl, and $C_2$-$C_{18}$ acyl, provided that if V is —N($X_{21}$)—, V' is —CH$_2$—; (III) $X_{18}$ and $X_{19}$ are each independently chosen from hydrogen, a lengthening agent L, and $C_1$-$C_{18}$ alkyl; and (IV) k is chosen from 0, 1, and 2, and each $X_{20}$ is independently chosen for each occurrence from a lengthening agent L, $C_1$-$C_{18}$ alkyl, $C_1$-$C_{18}$ alkoxy, hydroxy and halogen.

Each aryl and heteroaromatic group substituent can additionally and independently be chosen for each occurrence from, (13) a group represented by Formula vi,

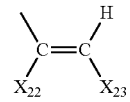

vi

With reference to Formula vi: (I) $X_{22}$ is chosen from hydrogen, a lengthening agent L, and $C_1$-$C_{18}$ alkyl; and (II) $X_{23}$ is chosen from a lengthening agent L and an unsubstituted, mono-, or di-substituted group chosen from naphthyl, phenyl, furanyl and thienyl, wherein each substituent is independently chosen for each occurrence from $C_1$-$C_{18}$ alkyl, $C_1$-$C_{18}$ alkoxy, and halogen.

In accordance with some further embodiments, group B can be selected from an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl. Each aryl and heteroaromatic group substituent is independently chosen for each occurrence from: (1) a lengthening agent L; (2) —COOX$_1$ or —C(O)X$_8$; (3) aryl, haloaryl, C$_3$-C$_7$ cycloalkylaryl, and an aryl group that is mono- or di-substituted with C$_1$-C$_{12}$ alkyl or C$_1$-C$_{12}$ alkoxy; (4) C$_1$-C$_{12}$ alkyl, C$_3$-C$_7$ cycloalkyl, C$_3$-C$_7$ cycloalkyloxy(C$_1$-C$_{12}$)alkyl, aryl(C$_1$-C$_{12}$)alkyl, aryloxy(C$_1$-C$_{12}$)alkyl, mono- or di-(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, haloalkyl, and mono(C$_1$-C$_{12}$)alkoxy(C$_1$-C$_{12}$)alkyl; (5) C$_1$-C$_{12}$ alkoxy, C$_3$-C$_7$ cycloalkoxy, cycloalkyloxy(C$_1$-C$_{12}$)alkoxy, aryl(C$_1$-C$_{12}$)alkoxy, aryloxy(C$_1$-C$_{12}$)alkoxy, mono- or di-(C$_1$-C$_{12}$)alkylaryl(C$_1$-C$_{12}$)alkoxy, and mono- or di-(C$_1$-C$_{12}$)alkoxyaryl(C$_1$-C$_{12}$)alkoxy; (6) amido, amino, mono- or di-alkylamino, diarylamino, piperazino, N—(C$_1$-C$_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen; (7) —OX$_7$ or —N(X$_7$)$_2$; (8) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, C$_1$-C$_6$ alkyl, C$_1$-C$_6$ alkoxy, phenyl, hydroxy, amino or halogen.

In accordance with some further embodiments, group B can be selected from an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl.

Each substituent can be independently chosen for each occurrence from: (1) a lengthening agent L; (2) —C(O)X$_6$; (3) aryl, haloaryl, C$_3$-C$_7$ cycloalkylaryl, and an aryl group that is mono- or di-substituted with C$_1$-C$_{12}$ alkyl or C$_1$-C$_{12}$ alkoxy; (4) C$_1$-C$_6$ alkyl, C$_3$-C$_5$ cycloalkyl, C$_3$-C$_5$ cycloalkyloxy(C$_1$-C$_6$)alkyl, aryl(C$_1$-C$_6$)alkyl, aryloxy(C$_1$-C$_6$)alkyl, mono- or di-(C$_1$-C$_6$)alkylaryl(C$_1$-C$_6$)alkyl, mono- or di-(C$_1$-C$_6$)alkoxyaryl(C$_1$-C$_6$)alkyl, haloalkyl, and mono(C$_1$-C$_6$)alkoxy(C$_1$-C$_6$)alkyl; (5) C$_1$-C$_6$ alkoxy, C$_3$-C$_6$ cycloalkoxy, cycloalkyloxy(C$_1$-C$_6$)alkoxy, aryl(C$_1$-C$_6$)alkoxy, aryloxy(C$_1$-C$_6$)alkoxy, mono- or di-(C$_1$-C$_6$)alkylaryl(C$_1$-C$_6$)alkoxy, and mono- or di-(C$_1$-C$_6$)alkoxyaryl(C$_1$-C$_6$)alkoxy; (6) aminocarbonyl, aminocarbonyl(C$_1$-C$_{18}$)alkylene, amino, mono- or di-alkylamino, diarylamino, piperazino, N—(C$_1$-C$_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen; (7) —OX$_7$ or —N(X$_7$)$_2$; and (8) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, C$_1$-C$_3$ alkyl, C$_1$-C$_3$ alkoxy, phenyl, hydroxy, amino or halogen.

The R$^3$ and R$^4$ groups of the indeno-fused ring compounds, for example represented by Formula I, and the indeno-fused ring pyran compounds, for example represented by Formula II, of the present invention can each be independently selected from: (i) hydrogen, C$_1$-C$_{20}$ alkyl, C$_1$-C$_{20}$ haloalkyl, C$_3$-C$_{10}$ cycloalkyl, allyl, benzyl, or mono-substituted benzyl, said benzyl substituents being chosen from halogen, C$_1$-C$_{20}$ alkyl or C$_1$-C$_{20}$ alkoxy; (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, C$_1$-C$_{20}$ alkyl or C$_1$-C$_{20}$ alkoxy; (iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material; (iv) the group —CH(R$^{10}$)G, wherein R$^{10}$ is hydrogen, C$_1$-C$_{20}$ alkyl or the unsubstituted, mono- or di-substituted aryl groups phenyl or naphthyl, and G is —CH$_2$OR$^{11}$, wherein R$^{11}$ is hydrogen, —C(O)R$^{10}$, C$_1$-C$_{20}$ alkyl, C$_1$-C$_{20}$ alkoxy(C$_1$-C$_{20}$)alkyl, phenyl(C$_1$-C$_{20}$)alkyl, mono(C$_1$-C$_{20}$)alkoxy substituted phenyl(C$_1$-C$_{20}$)alkyl, or the unsubstituted, mono- or di-substituted aryl groups phenyl or naphthyl, each of said phenyl and naphthyl group substituents being C$_1$-C$_{20}$ alkyl or C$_1$-C$_{20}$ alkoxy.

According to some alternative embodiments, (v) R$^3$ and R$^4$ can together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom. The spiro-carbocyclic ring and the spiro-heterocyclic ring are each annellated with 0, 1 or 2 benzene rings. The substituents of the spiro rings can be chosen from hydrogen or C$_1$-C$_{20}$ alkyl (e.g., C$_1$-C$_6$ alkyl).

In accordance with further embodiments of the present invention, R$^3$ and R$^4$ are each independently selected from hydrogen, C$_1$-C$_8$ alkyl, C$_1$-C$_8$ haloalkyl, and C$_3$-C$_7$ cycloalkyl. Alternatively, R$^3$ and R$^4$ together can form a spiro substituent selected from a substituted or unsubstituted spiro-carbocyclic ring containing 3 to 6 carbon atoms.

The B and B' groups of the indeno-fused ring pyran compounds of the present invention, for example represented by Formula II, can each independently be selected from those classes, groups and examples as described previously herein with regard to group B.

Alternatively, B and B' can with some embodiments together form fluoren-9-ylidene, mono- or di-substituted fluoren-9-ylidene, or a saturated C$_3$-C$_{12}$ spiro-monocyclic hydrocarbon ring, saturated C$_7$-C$_{12}$ spiro-bicyclic hydrocarbon rings, saturated C$_7$-C$_{12}$ spiro-tricyclic hydrocarbon rings; and said fluoren-9-ylidene substituents being selected from the group consisting of C$_1$-C$_4$ alkyl, C$_1$-C$_4$ alkoxy, bromo, fluoro and chloro.

Further alternatively, B and B' can with some embodiments together form fluoren-9-ylidene, mono- or di-substituted fluoren-9-ylidene, or a saturated C$_3$-C$_8$ spiro-monocyclic hydrocarbon ring, saturated C$_7$-C$_{10}$ spiro-bicyclic hydrocarbon rings, saturated C$_7$-C$_{10}$ spiro-tricyclic hydrocarbon rings, said fluoren-9-ylidene substituents being selected from the group consisting of C$_1$-C$_3$ alkyl, C$_1$-C$_3$ alkoxy, fluoro and chloro.

With some embodiments, B and B' together form fluoren-9-ylidene, adamantylidene, bornylidene, norbornylidene or bicyclo(3.3.1)nonan-9-ylidene.

The indeno-fused ring compound can with some embodiments of the present invention, be represented by the following Formula Ia,

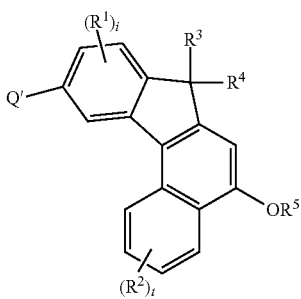

With reference to Formula Ia, subscript (t) is selected from 0 to 4, and the groups $R^1$, $R^2$, $R^3$, $R^4$, $R^5$, and Q', and subscript (i) are each as described previously herein.

With further embodiments, Q' of the indeno-fused ring compound represented by Formula Ia is selected from —CN, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$ and —C(O)NR$^a$R$^a$, in which R$^a$ and R$^b$ are each independently as described previously herein.

In accordance with some embodiments of the present invention, the indeno-fused ring pyran compound is represented by the following Formula IIa,

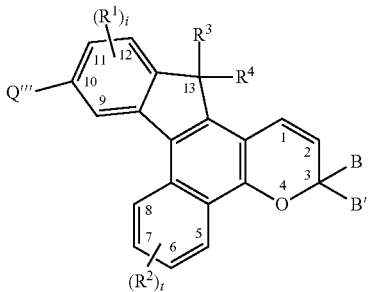

With reference to Formula IIa, subscript (t) is selected from 0 to 4, and the groups $R^1$, $R^2$, $R^3$, $R^4$, Q''', B and B', and subscript (i) are each as described previously herein. The numbers within the ring structures of Formula IIa indicate positions to which various groups can be bonded thereto. For example, B and B' are each bonded to Position-3, $R^3$ and $R^4$ are each bonded to Position-13, and Q''' is bonded to Position-10. The $R^1$ group(s) can be bonded to Positions-9, 11, and 12, and the $R^2$ group(s) can be bonded to Positions-5, 6, 7, and 8.

With further embodiments, Position-12 of the indeno-fused ring pyran compound represented by Formula IIa, is substituted with hydrogen, and Q''' is —CN.

With additional embodiments, and with further reference to the indeno-fused ring pyran compound represented by Formula IIa, i is at least 1, Position-12 has $R^1$ bonded thereto, and Q''' is selected from —N$_3$, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, and —OS(O$_2$)R$^b$.

In accordance with further embodiments of the present invention, each lengthening agent L of the indeno-fused ring compounds and the indeno-fused ring pyran compounds of the present invention, can be independently selected from the compounds listed in Table 1 of U.S. Pat. No. 7,342,112, which disclosure is incorporated herein by reference, and the following compounds.

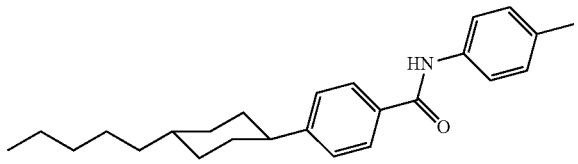 [SMILES: CCCCCC1CCC(c2ccc(C(=O)Nc3ccc(C)cc3)cc2)CC1]

(4-((1s,4r)-4-pentylcyclohexyl)benzamido)phenyl

4-((4-((1s,4r)-4-pentylcyclohexyl)phenoxy)carbonyl) phenyl

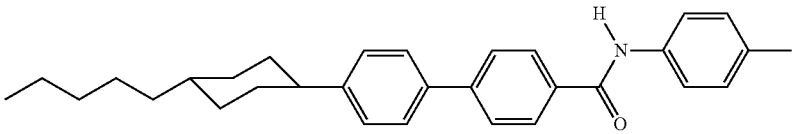 [SMILES: CCCCCC1CCC(c2ccc(-c3ccc(C(=O)Nc4ccc(C)cc4)cc3)cc2)CC1]

4-(4-(4-((1s,4r)-4-pentylcyclohexyl)phenyl)benzamido) phenyl

4-((((1's,4'r)-4'-pentyl-[1,1'-bi(cyclohexan)]-4-yl)oxy)carbonyl)phenyl
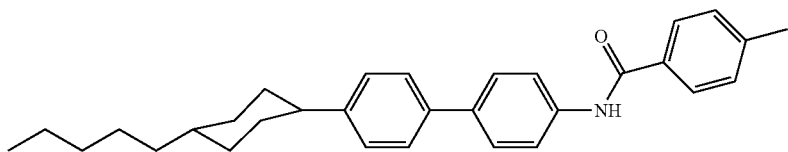 [SMILES: CCCCCC1CCC(c2ccc(-c3ccc(NC(=O)c4ccc(C)cc4)cc3)cc2)CC1]
4-(4'-(4-pentylcyclohexyl)-[1,1'-biphenyl]-4-ylcarboxamido)phenyl
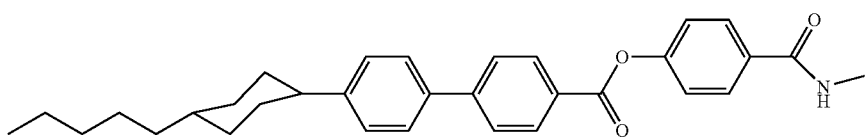 [SMILES: CCCCCC1CCC(c2ccc(-c3ccc(C(=O)Oc4ccc(C(=O)NC)cc4)cc3)cc2)CC1]
4-((4'-(4-pentylcyclohexyl)-[1,1'-biphenyl]-4-carbonyl)oxy)benzamido
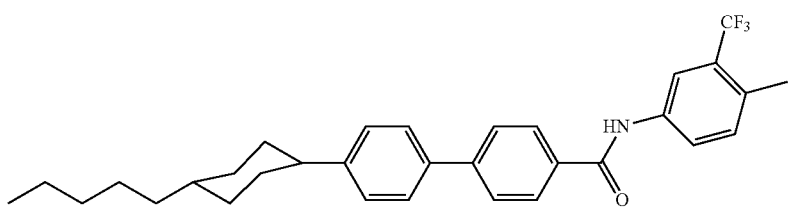 [SMILES: CCCCCC1CCC(c2ccc(-c3ccc(C(=O)Nc4ccc(C)c(C(F)(F)F)c4)cc3)cc2)CC1]
4-(4'-(4-pentylcyclohexyl)-[1,1'-biphenyl]-4-carbonyl)piperazin-1-yl
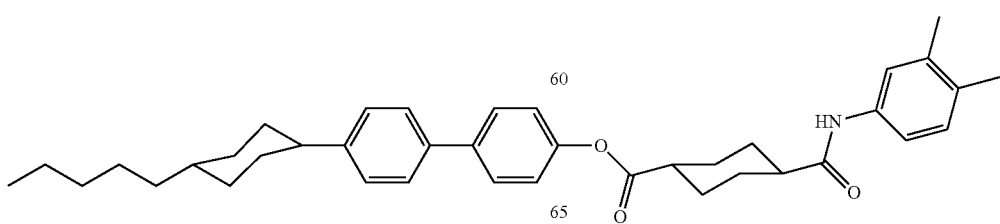 [SMILES: CCCCCC1CCC(c2ccc(-c3ccc(OC(=O)C4CCC(C(=O)Nc5ccc(C)c(C)c5)CC4)cc3)cc2)CC1]
4-(4-(4-((1s,4r)-4-pentylcyclohexyl)phenyl)benzamido)-2-(trifluoromethyl)phenyl 2-methyl-4-((1r,4r)-4-((4'-((1s,4r)-4-pentylcyclohexyl)biphenyl-4-yloxy)carbonyl)cyclohexanecarboxamido)phenyl

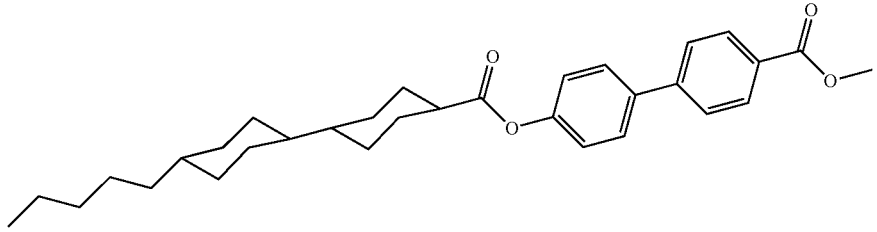 [SMILES: CCCCCC1CCC(C2CCC(C(=O)Oc3ccc(-c4ccc(C(=O)OC)cc4)cc3)CC2)CC1]

4'-((1r,1's,4R,4'R)-4'-pentylbi(cyclohexane-4-) carbonyloxy)biphenylcarbonyloxy

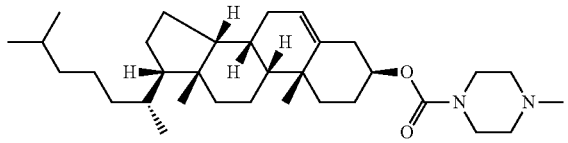

4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl

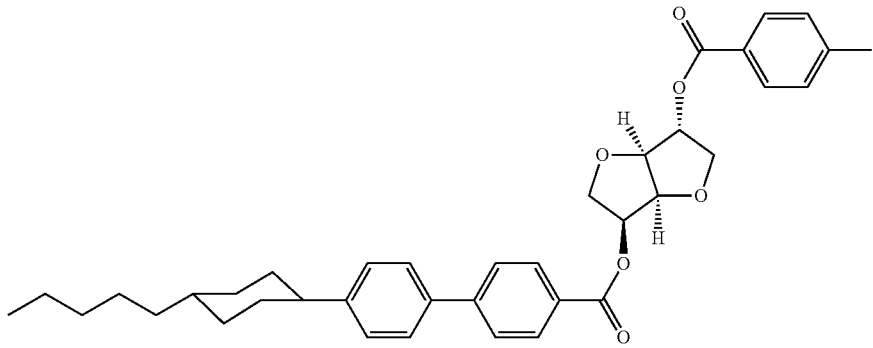 [SMILES: CCCCCC1CCC(c2ccc(-c3ccc(C(=O)O[C@H]4CO[C@@H]5[C@H]4OC[C@H]5OC(=O)c4ccc(C)cc4)cc3)cc2)CC1]

4-((S)-2-methylbutoxy)phenyl)-10-(4-(((3R,3aS,6S,6aS)-6-(4'-((1s,4S)-4-pentylcyclohexyl)biphenylcarbonyloxy)hexahydrofuro[3,2-b]furan-3-yloxy)carbonyl)phenyl The indeno-fused ring pyran compounds of the present invention, such as those represented by Formulas II and IIa, can be used to render compositions and/or articles photochromic. Examples of articles that can be rendered photochromic by the indeno-fused ring pyran compounds of the present invention include, but are not limited to, optical elements, displays, windows (or transparencies), mirrors, and components or elements of liquid crystal cells. As used herein the term "optical" means pertaining to or associated with light and/or vision. Examples of optical elements that can be rendered photochromic include, without limitation, ophthalmic elements, display elements, windows, mirrors, and liquid crystal cell elements. As used herein the term "ophthalmic" means pertaining to or associated with the eye and vision.

Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Articles can be rendered photochromic with the indeno-fused ring pyran compounds of the present invention by methods including, but not limited to, imbibition methods, cast-in-place methods, coating methods, in-mold coating methods, over-mold methods, and lamination methods. With imbibition methods, the indeno-fused ring pyran compound is typically diffused into a polymeric material of a previously formed or fabricated article, such as a substrate or previously mmersing the polymeric material of a previously formed or applied coating or film. Imbibition can be performed by ifabricated article in a solution containing the indeno-fused ring pyran compound, with or without heating. Thereafter, although not required, the indeno-fused ring pyran compound can be bonded with the polymeric material (e.g., of the substrate or coating).

With cast-in-place methods, the indeno-fused ring pyran compound can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set (e.g., cured) within the mold so as to form a photochromic article.

With articles that include a substrate, the indeno-fused ring pyran compounds of the present invention can be connected to at least a portion of the substrate as part of a coating that is connected to at least a portion of the substrate. The substrate can be a polymeric substrate or an inorganic substrate (such as, but not limited to, a glass substrate). The indeno-fused ring pyran compound of the present invention can be incorporated into at least a portion of a coating composition prior to application of the coating composition to the substrate. Alternatively, a coating composition can be applied to the substrate, at least partially set, and thereafter the indeno-fused ring pyran compound of the present invention can be imbibed into at least a portion of the coating. As used herein, the terms "set" and "setting" include, without limitation, curing, polymerizing, cross-linking, cooling, and drying.

Photochromic articles can be prepared using the indeno-fused ring pyran compounds of the present invention by art-recognized in-mold coating (or in-mold casting) methods. With in-mold coating methods, a photochromic coating composition including the indeno-fused ring pyran compound of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the indeno-fused ring pyran compounds according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles prepared using the indeno-fused ring pyran compounds of the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space.

Photochromic articles, prepared using the indeno-fused ring pyran compounds of the present invention, can also be formed by art-recognized lamination methods. With lamination methods, a film comprising the indeno-fused ring pyran compounds of the present invention can be adhered or otherwise connect to a portion of the substrate, with or without an adhesive and/or the application of heat and pressure. Thereafter, if desired, a second substrate can be applied over the first substrate and the two substrates can be laminated together (e.g., by the application of heat and pressure) to form an element wherein the film comprising the indeno-fused ring pyran compound is interposed between the two substrates. Methods of forming films comprising a photochromic material can include for example and without limitation, combining a photochromic material with a polymeric solution or oligomeric solution or mixture, casting or extruding a film therefrom, and, if required, at least partially setting the film. Additionally or alternatively, a film can be formed (with or without a photochromic material) and imbibed with the photochromic material.

The indeno-fused ring pyran compounds of the present invention, can be used alone or in combination with other photochromic materials. Classes of photochromic materials that can be used in combination (e.g., in mixture) with the indeno-fused ring pyran compounds of the present invention include, but are not limited to: spiro(indoline)naphthoxazines and spiro(indoline)benzoxazines, for example as described in U.S. Pat. Nos. 3,562,172, 3,578,602, 4,215,010, 4,342,668, 5,405,958, 4,637,698, 4,931,219, 4,816,584, 4,880,667, and 4,818,096; benzopyrans, for example as described in U.S. Pat. Nos. 3,567,605, 4,826,977, 5,066,818, 4,826,977, 5,066, 818, 5,466,398, 5,384,077, 5,238,931, and 5,274,132; photochromic organo-metal dithizonates, such as, (arylazo)-thioformic arylhydrazidates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

The present invention also relates to a photochromic composition that includes: (a) a indeno-fused ring pyran compound of the present invention; and (b) an organic material selected from a polymer, an oligomer, a monomer, and combinations of two or more thereof. The polymer of the photochromic composition can be selected from polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and combinations thereof.

The photochromic compositions of the present invention can optionally further include, at least one additive selected from dyes, alignment promoters, photoinitiators, thermal initiators, polymerization inhibitors, solvents, light stabilizers, heat stabilizers, mold release agents, rheology control agents, leveling agents, free radical scavengers, and adhesion promoters.

The present invention also relates to a photochromic coating composition that includes: (a) a indeno-fused ring pyran compound of the present invention; (b) a film forming composition selected from a curable resin composition, a thermoplastic resin composition, and combinations thereof; and (c) optionally a solvent composition.

The present invention also relates to photochromic articles that include the indeno-fused ring pyran compound of the present invention. Examples of photochromic articles of the preset invention include, but are not limited to, optical elements selected from at least one of, an ophthalmic element, a display element, a window, a mirror, packaging material, an active liquid crystal cell element, and a passive liquid crystal cell element.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

Examples of photochromic ophthalmic elements of the present invention include, but are not limited to, corrective lenses, non-corrective lenses, contact lenses, intra-ocular lenses, magnifying lenses, protective lenses, and visors. Examples of display elements include, but are not limited to, screens, monitors, and security elements.

Further, the photochromic compounds according to various non-limiting embodiments of the present invention can have an average absorption ratio of at least 1.5 in an activated state as determined according to CELL METHOD. According to other non-limiting embodiments, the photochromic compound can have an average absorption ratio ranging from 4 to 20, 3 to 30, or 2.5 to 50 in an activated state as determined according to CELL METHOD. According to still other non-limiting embodiments, the photochromic compounds can have an average absorption ratio ranging from 1.5 to 50 in an activated state as determined according to CELL METHOD.

Reaction sequences for forming the photochromic compounds according to various non-limiting embodiments of the present invention having an L group are disclosed in Reaction Sequences A through J, K, M, N, P, Q, T in U.S. Pat. No. 7,342,112, which disclosure is incorporated herein by reference.

As discussed in the schemes outlined further below, compound 105 represents one of the indenofused ring compounds described herein. It also serves as the basis for preparing other indenofused ring compounds described herein. For example, it can be prepared as shown in Schemes 1, 2, 3, 4 and 5. Once prepared, the hydroxy functionality of compound 106 can be used for pyran formation and the halogen of 105 or one of its precursors 408 can be used for converting to Q' as shown in Scheme 6. All structures from Scheme 6 are the indenofused ring compounds described herein.

Detailed chemical reactions that can be used for converting 106 to 604 can be observed in Scheme 7, 8 and 9. Detailed chemical reactions for converting the pyran dye 606 to 605 can be found in Scheme 10.

For all the indenofused ring compounds described in Schemes 1-5, X, which is a halogen group, was introduced into the structure before formation of the indenofused ring. The X group was then converted to another member from which Q' can be selected. Scheme 11 shows that X can also be introduced into the indenofused ring compound after the formation of indenofused ring. Scheme 11 also shows that other members from which Q' can be selected, can be introduced into the structure without going through or requiring the presence of X.

In all schemes, X may be selected from halogen, e.g., F, Sr, Cl and I. Each t and i is an integer chosen from 0 to the total number of available positions. From Scheme 1 to Scheme 6, $R^1$ for each occurrence, may be independently selected from hydrogen, halogen and optionally substituted chiral or achiral groups selected from alkyl, perfluoroalkyl, alkenyl, alkynyl, cycloalkyl, aryl, heteroaryl, alkoxy, perfluoroalkoxy, heteroalkyl, heterocycloalkyl, alkylthiol, arylthiol, amino aminocarbonyl, aryloxycarbonyl, alkyloxycarbonyl, aminocarbonyloxy, alkoxycarbonylamino, aryloxycarbonylamino, cycloalkoxycarbonylamino, heterocycloalkyloxycarbonylamino and heteroaryloxycarbonylamino. $R^2$ is selected from $R^1$.

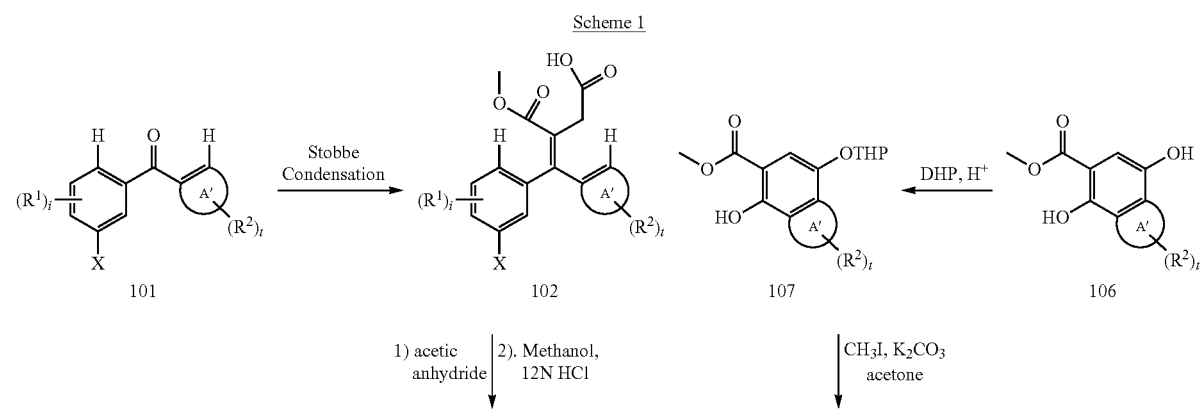

Scheme 1

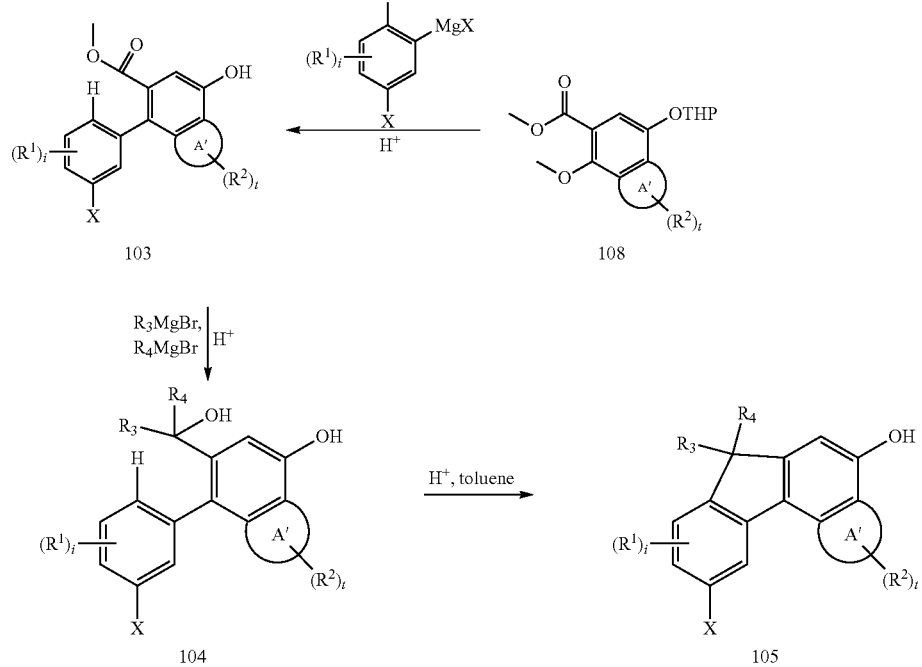

X = Br, I, Cl

Scheme 1 shows one way of preparing compound 105. $R_3$ and $R_4$ may be selected from optionally substituted chiral or achiral groups such as heteroalkyl, alkyl, perfluoroalkyl, alkenyl, alkynyl, aryl, heteroaryl, cycloalkyl, and heterocycloalkyl.

The aryl ketone 101 can either be purchased or prepared by Friedel-Crafts methods or Grignard or Cuperate methods known in the art. For example, see the publication *Friedel-Crafts and Related Reactions*, George A. Olah, Interscience Publishers, 1964, Vol. 3, Chapter XXXI (Aromatic Ketone Synthesis); "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; "Addition of Grignard Reagents to Aryl Acid Chlorides: An efficient synthesis of aryl ketones" by Wang, Xiaojun et al, Organic Letters, Vol. 7, No. 25, 5593-5595, 2005, and references cited therein, which disclosures related to the aforementioned synthetic methods are incorporated herein by reference in their entireties. A Stobbe reaction of aryl ketone 101 with dimethyl succinate in the presence of potassium t-butoxide provides the condensed product of compound 102, which undergoes a ring closure reaction in acetic anhydride followed by methanolysis to form the product of compound 103.

Compound 103 can also be prepared from an ester-mediated nucleophilic aromatic substitution reaction starting from compound 106 by methods known to those skilled in the art, for example, as further described in Synthesis, January 1995, pages 41-43; The Journal of Chemistry Society Perkin Transaction 1, 1995, pages 235-241 and U.S. Pat. No. 7,557,208 B2, which disclosures related to such synthetic methods are incorporated herein by reference in their entireties.

Compound 103 can be further converted to the indeno-fused product of compound 105 with various substitutions on the bridge carbon via various multistep reactions that can be found in U.S. Pat. Nos. 5,645,767; 5,869,658; 5,698,141; 5,723,072; 5,961,892; 6,113,814; 5,955,520; 6,555,028; 6,296,785; 6,555,028; 6,683,709; 6,660,727; 6,736,998; 7,008,568; 7,166,357; 7,262,295; 7,320,826 and 7,557,208, which disclosures related to the substituents on the bridge carbon are incorporated herein by reference in their entireties. Scheme 1 illustrates that compound 103 reacts with Grignard reagent followed by a ring closure reaction to provide compound 105.

Scheme 2

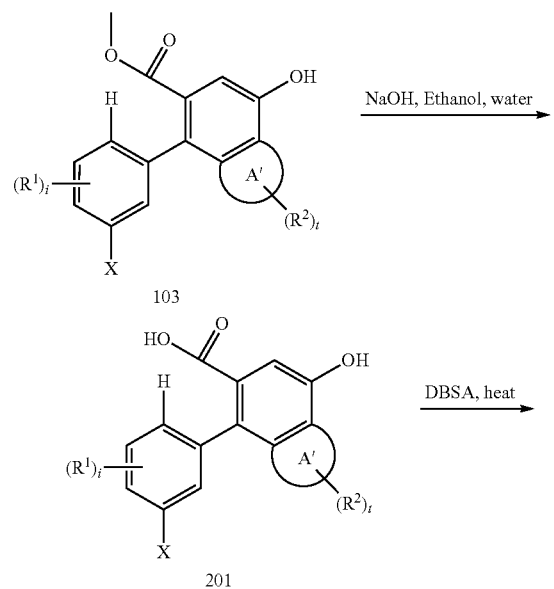

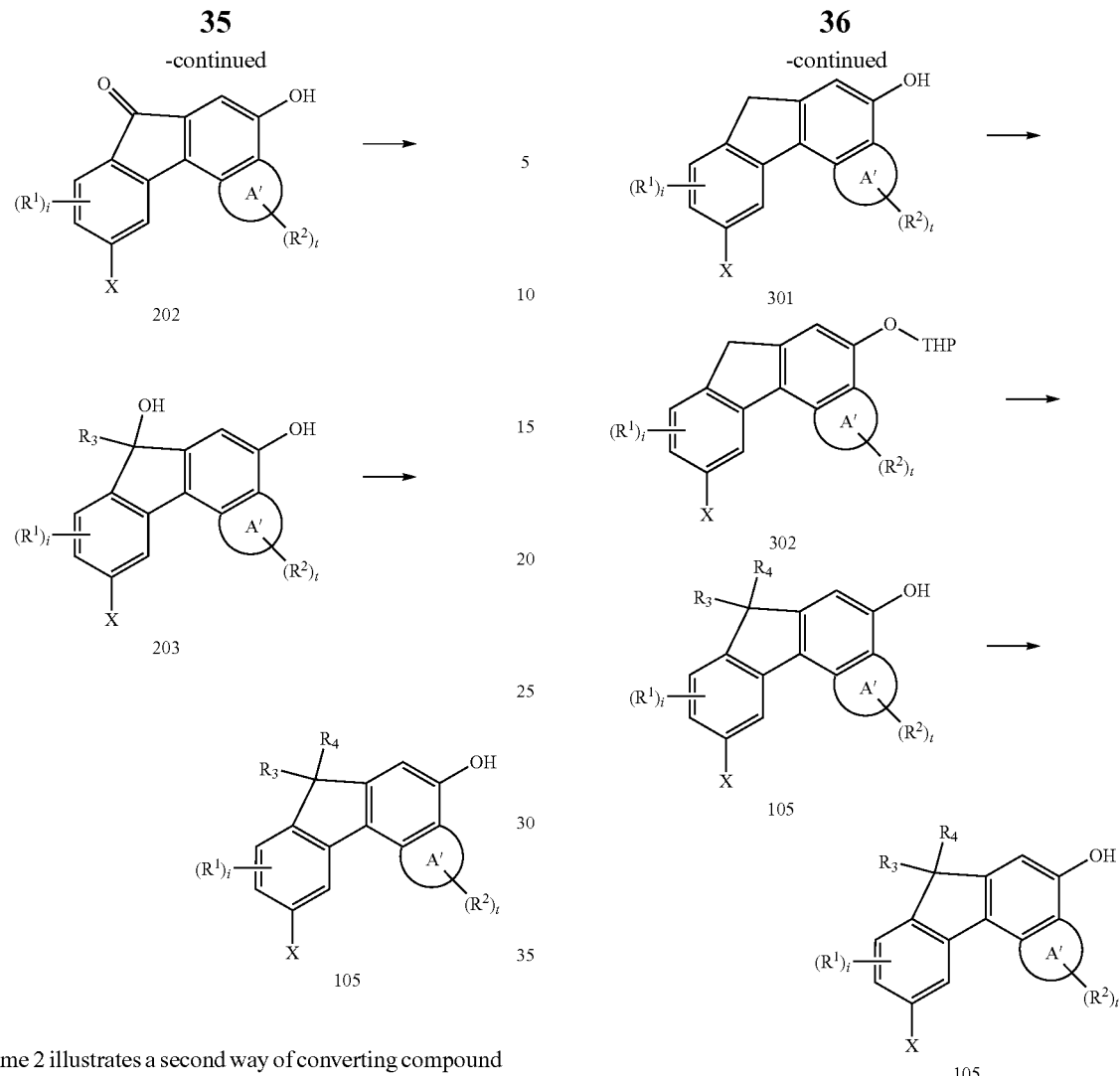

Scheme 2 illustrates a second way of converting compound 103 to compound 105. After hydrolysis of compound 103 followed by a ring closure reaction, compound 202 was obtained. The carbonyl of compound 202 can react with a nucleophile, like a Grignard reagent, an Organo lithium reagent, or a perfluoalkyl trimethylsilane to form compound 203. $R^3$ may be selected from optionally substituted chiral or achiral groups such as heteroalkyl, alkyl, perfluoroalkyl, alkenyl, alkynyl, aryl, heteroaryl, cycloalkyl and heterocycloalkyl. The hydroxyl group of compound 203 can be converted into $R^4$, which may be selected from halogen and optionally substituted chiral or achiral groups such as alkoxy, silanoxy, heteroaryloxy and aryloxy.

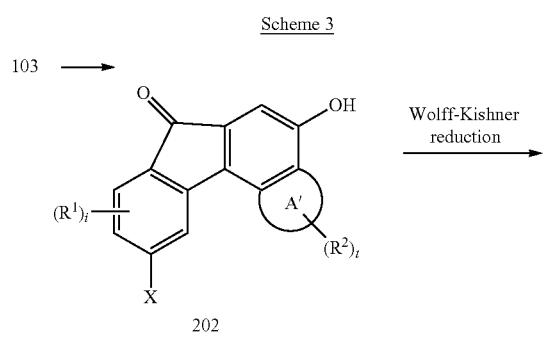

Scheme 3 illustrates a third way of converting compound 103 to compound 105. Compound 202 from Scheme 2 can be reduced to 301 using a Wolff-Kishner reduction or its modified version. Examples can be found in "Practical procedures for the preparation of N-tert-butyldimethylsilylhydrozones and their use in modified Wolff-Kishner reductions and in the synthesis of vinyl halides and gem-dihalides" by Furrow, M. E., et al, J Am Chem Soc: 126(17): 5436-45, May 5, 2004, and references therein, which disclosures related to the Wolff-Kishner reduction are incorporated herein by reference. After hydroxy protection, compound 302 has a very nucleophilic gem-carbon once deprotonated by base like LDA or methyl Grignard reagent. By those skilled in the art, the deprotonated compound 302 can be converted to $R^3$ and $R^4$ substituted compound by reacting it with electrophiles such as alkyl halides, carbon dioxide, acid chlorides, nitriles and chloroformate derivatives. As a result, compound 105 can be prepared with $R^3$ and $R^4$ selected from hydrogen, optionally substituted chiral or achiral groups selected from heteroalkyl, alkyl, cycloalkyl, carboxy, alkylcarbonyl, alkoxycarbonyl, alkylcarbonyl, alkoxycarbonyl, aminocarbonyl, arylcarbonyl, aryloxycarbonyl, or $R^3$ and $R^4$ may be taken together with any intervening atoms to form a group selected from oxo, optionally substituted cycloalkyl, and optionally substituted heterocycloalkyl.

Schemes 4 and 5 summarize two novel methods of preparing compound 105, which are not believed to have been previously described.

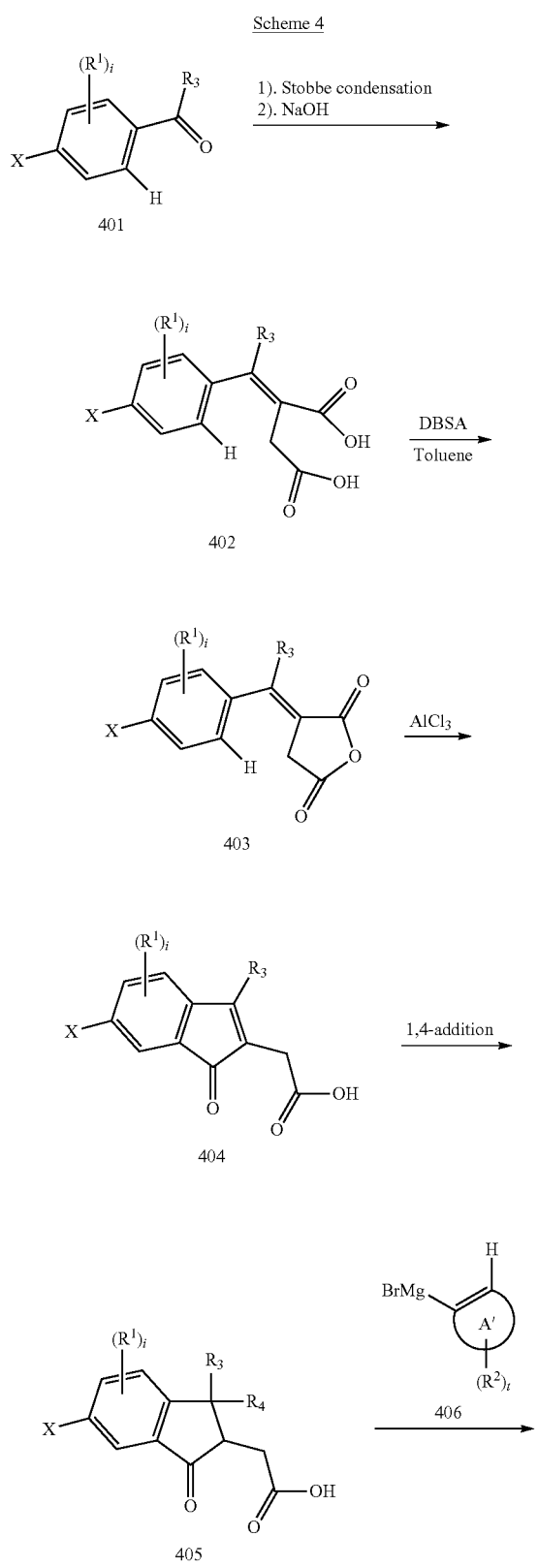

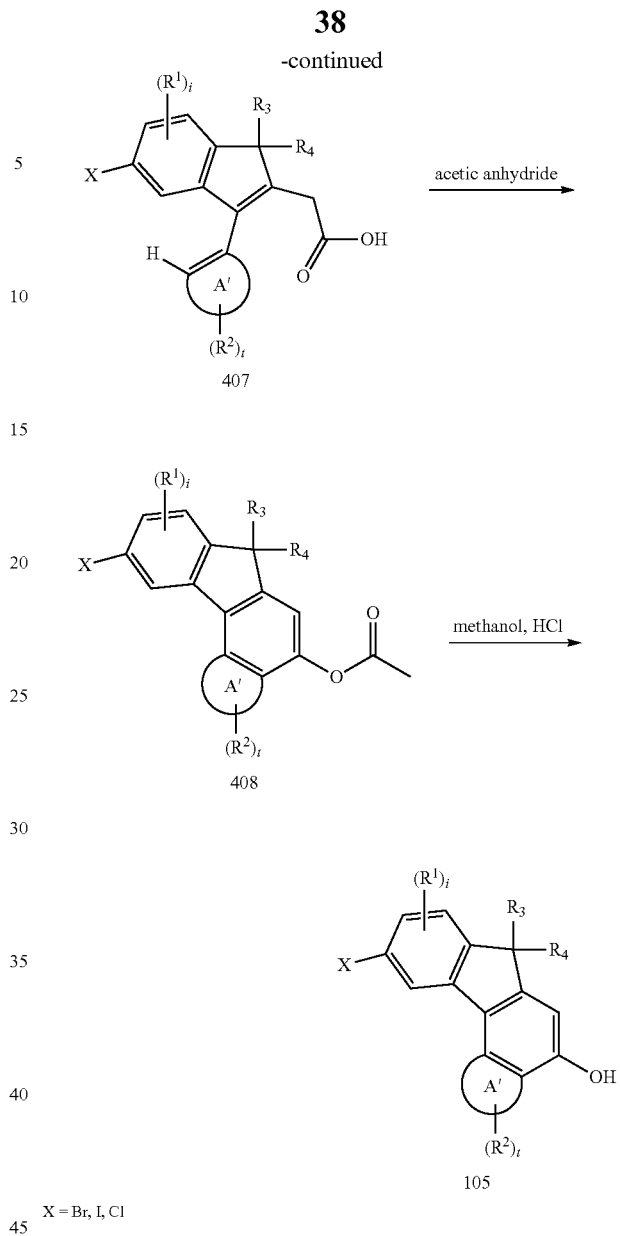

X = Br, I, Cl

Scheme 4 starts with aryl ketone 401. $R_3$ may be selected from hydrogen, optionally substituted chiral or achiral groups such as heteroalkyl, alkyl, perfluoroalkyl, alkenyl, alkynyl, aryl, heteroaryl, cycloalkyl and heterocycloalkyl.

After a Stobbe reaction with dimethyl succinate, compound 402 is converted to an anhydride 403. This anhydride can be transformed into an indenone acid 404 with the use of aluminum chloride. A 1,4-addition reaction can be done with the use of nucleophiles like organometallic reagent, amine, alcohol and thiol. The reaction produces indano acid 405. $R_4$ may be selected from hydrogen, optionally substituted chiral or achiral groups such as heteroalkyl, alkyl, alkenyl, alkynyl, aryl, heteroaryl, cycloalkyl, heterocycloalkyl, amino, alkoxy, and thiol. Compound 405 can be reacted with a Grignard reagent 406 to form compound 407 after an acidic workup. Compound 407 undergoes a ring closure reaction in acetic anhydride followed by methanolysis to form product 408, which can be either used directly in Scheme 6 or converted to compound 105 by hydrolysis.

Scheme 5

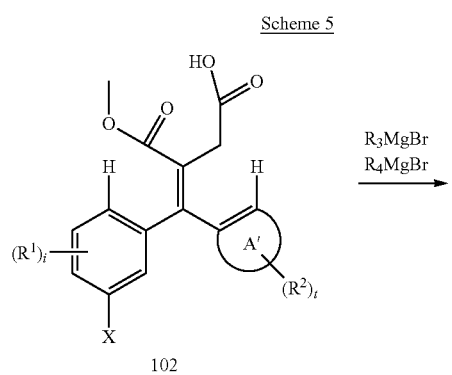

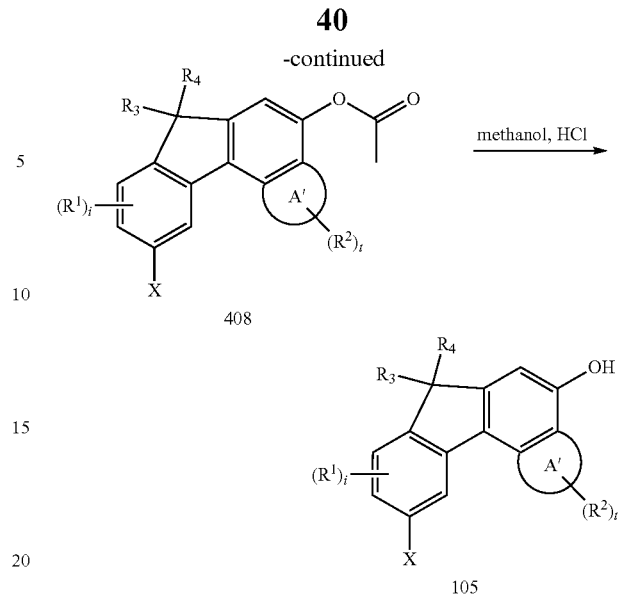

Scheme 5 starts with Stobbe product 102, which reacts with a Grignard reagent to provide compound 501. $R_3$ and $R_4$ may be selected from optionally substituted chiral or achiral groups such as heteroalkyl, alkyl, perfluoroalkyl, alkenyl, alkynyl, aryl, heteroaryl, cycloalkyl and heterocycloalkyl. After treating with bismuth triflate in toluene and then acetic anhydride, two ring closure reactions occur in the same pot sequentially. The reaction results in compound 408, which can be converted into compound 105.

Scheme 6

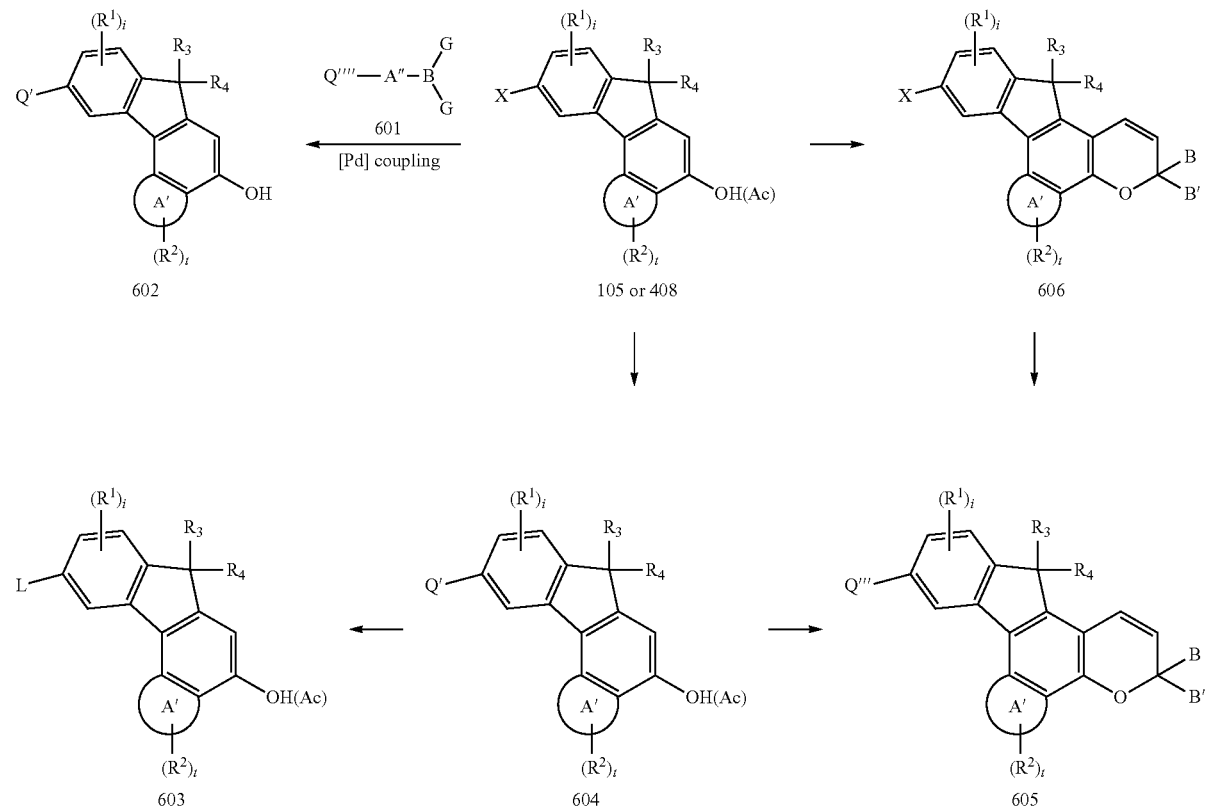

Scheme 6 illustrates methods of converting compounds 105 (with —OH) or 408 (with acetate) into other indenofused ring compounds. The hydroxy group of 105 can be used in the chemistry for forming pyran dye 606, the halogen of which can be converted to Q''' as observed in Scheme 10. Halogen X of 105 can be converted to Q' with the formation of compound 604. Details are discussed in Schemes 7-9. Compound 604 can react with a propargyl alcohol to form pyran dye 605. The Q' of 604 can also be converted to a different Q' represented by the lengthening group L. When the Suzuki reaction is used, the Q'''' and A'' of the boronic acid derivative 601, together form a Q' on 602. Methods for the synthesis of the boronic acid derivatives can be found from "Palladium(0)-Catalyzed Cross-Coupling Reaction of Alkoxydiboron with Haloarenes: A Direct Procedure for Arylboronic Esters, J. Org. Chem. 60, page 7508-7519, 1995" by Miyaura, Norio et als and references therein, which disclosures related to such synthetic methods are incorporated herein by reference. As described herein, G may be —OH or —O-Alkyl; A'' may be selected from aryl, alkenyl, alkynyl and heteroaryl; Q'''' may be selected from halogen, —OH, —N$_3$, —NR$^a$R$^a$, —N(R$^a$)C(O)Q'', —CN, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$, C(O)NR$^a$R$^a$ and a lengthening agent L. The groups Q'''' and A'' together form the Q' group. B and B' may be each independently selected from L, hydrogen, halogen, and optionally substituted chiral or achiral groups such as metallocenyl, alkyl or perfluoroalkyl, alkenyl, alkynyl, heteroalkyl, alkoxy, perfluoroalkoxy, aryl, heteroaryl, heterocycloalkyl, and cycloalkyl, or wherein B and B' are taken together with any intervening atoms to form a group such as optionally substituted cycloalkyl and optionally substituted heterocycloalkyl.

The group Q' may be selected from halogen, —OH, —N$_3$, —NR$^a$R$^a$, —N(R$^a$)C(O)Q'', —CN, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$, C(O)NR$^a$R$^a$ and a lengthening agent L. The group Q''' may be selected from halogen, —OH, —N$_3$, —NR$^a$R$^a$, —N(R$^a$)C(O)Q'', —CN, —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$, and C(O)NR$^a$R$^a$ Schemes 7, 8 and 9 illustrate details of converting halogen to Q'. The chemistries are done at hydroxy stage starting from compound 105, which is shown as compound 701 representing a naphthol in Schemes 7 and 8. The product of scheme 8, represented by compound 801 is used in Scheme 9 as the starting material to form the compounds shown. Each of the hydroxy products of compounds 702, 706, 708, 709, 710, 802, 803, 807, 809, 810, 811, 812, 901, 903, 904 and 906 can be converted to pyran photochromic compounds using the propargyl alcohol chemistry shown in Scheme 6.

Scheme 7

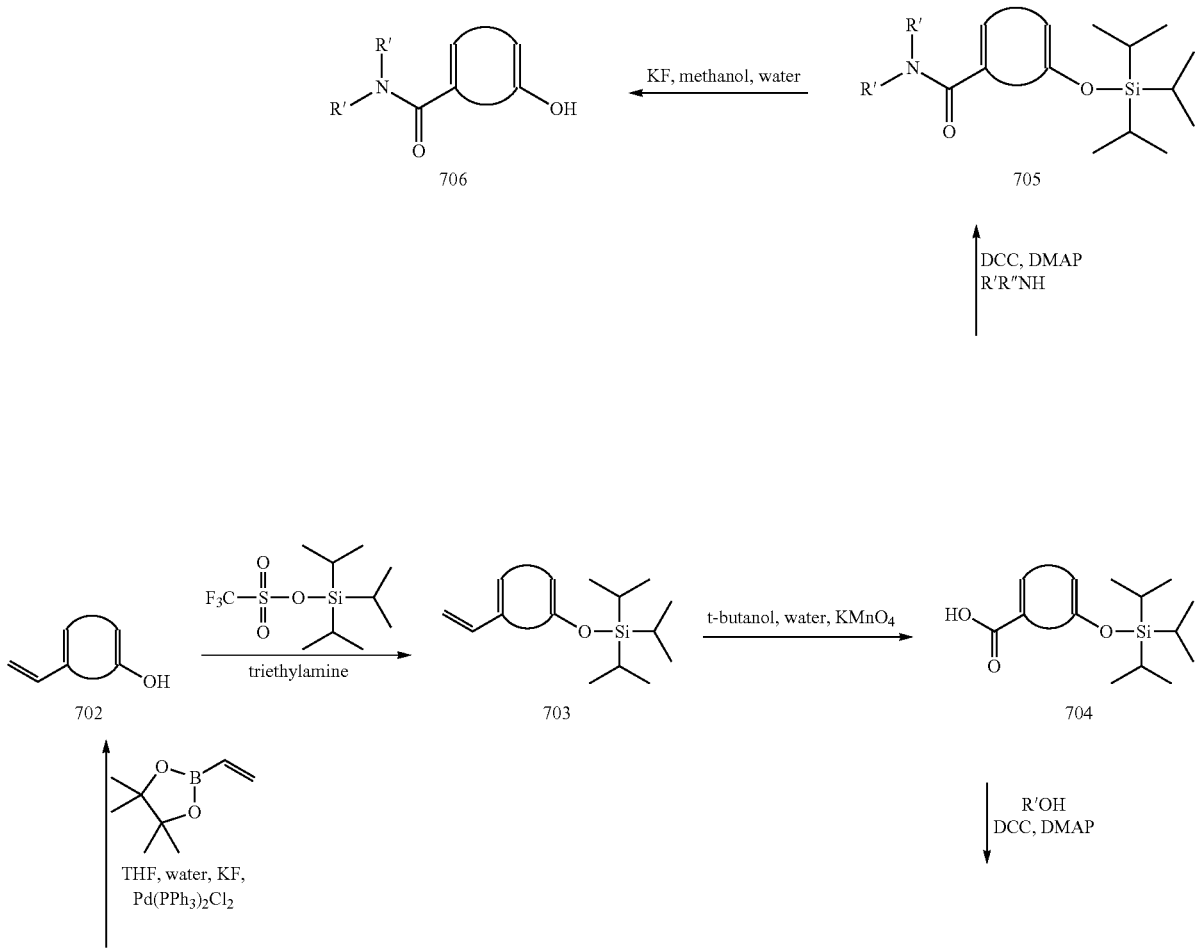

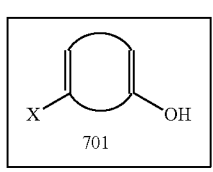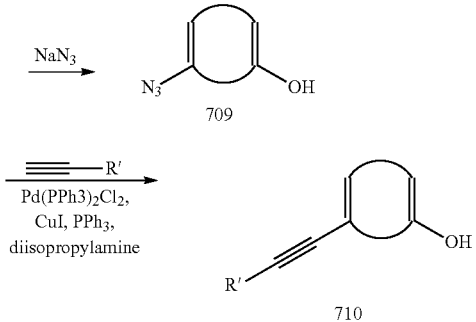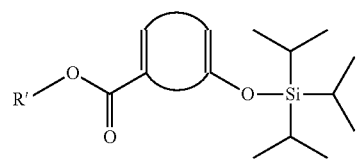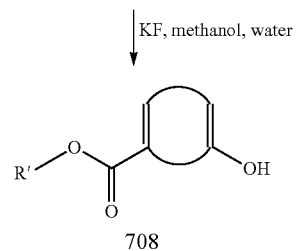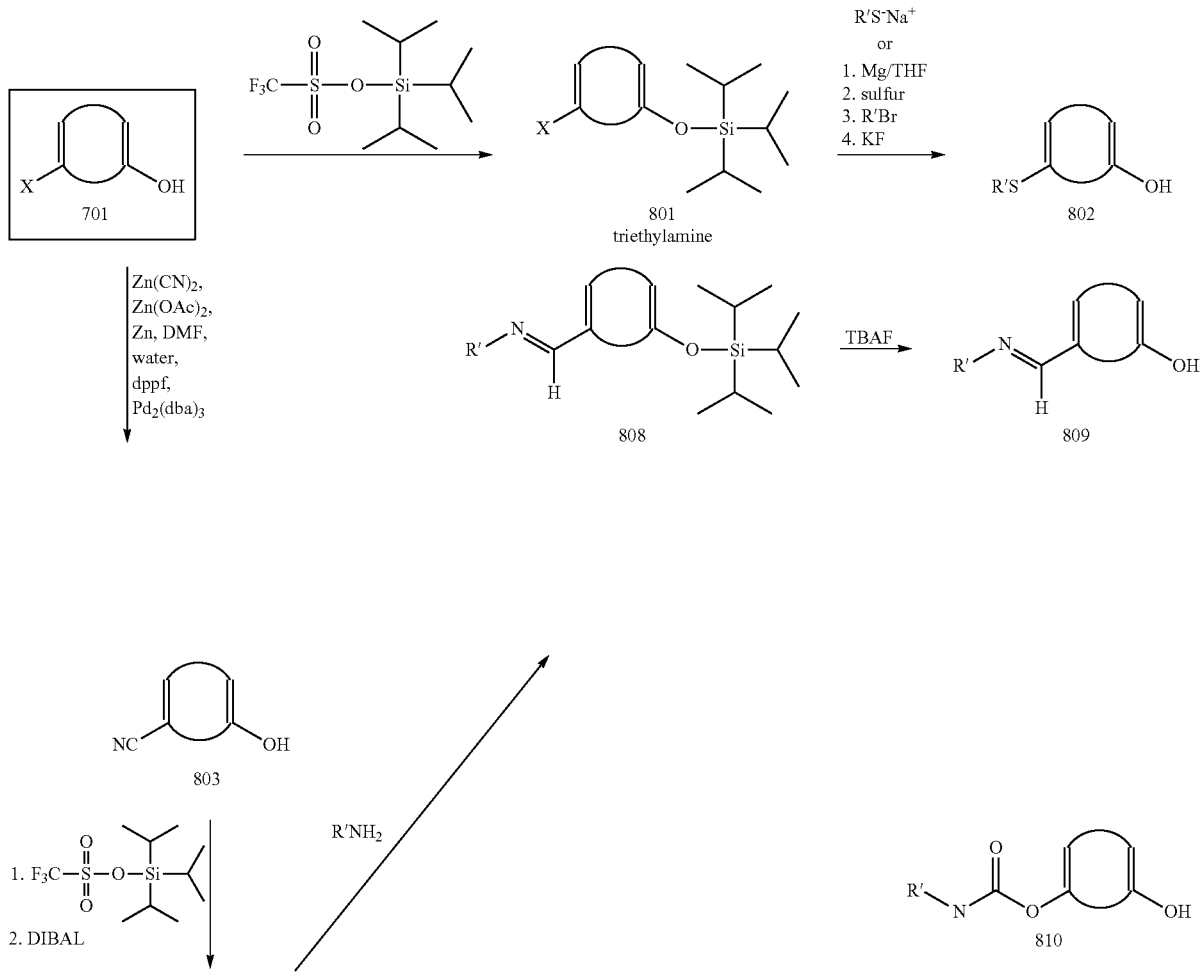

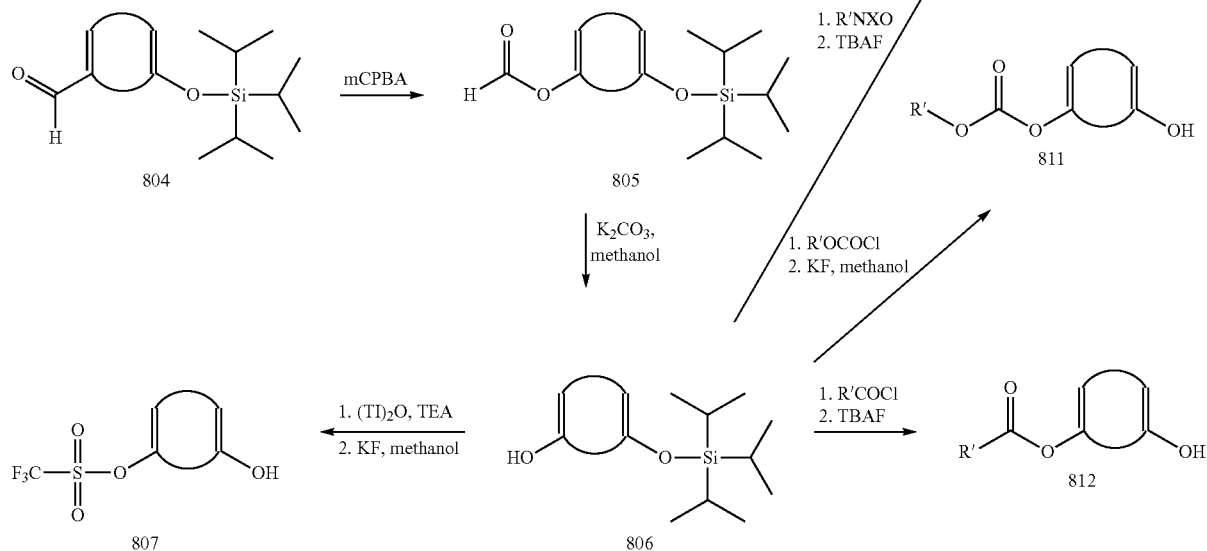
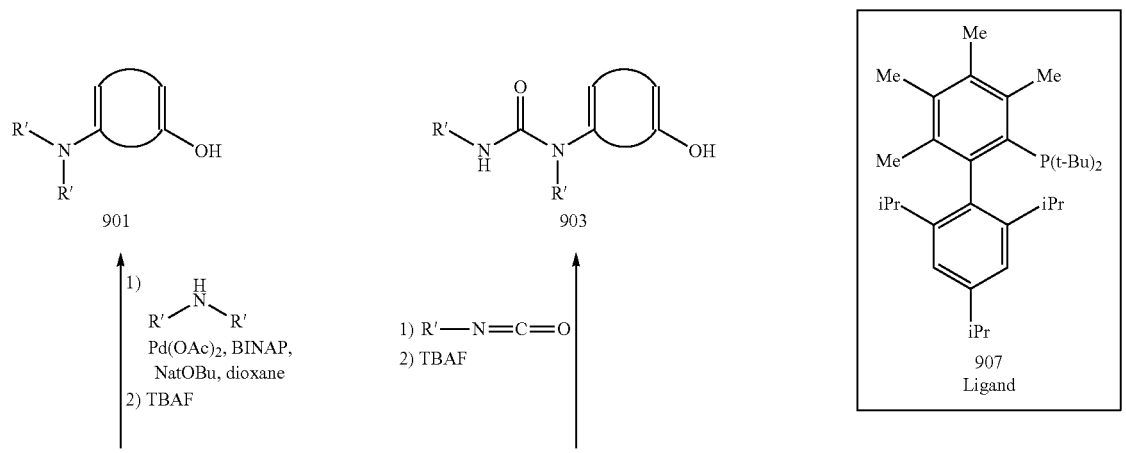
Scheme 9
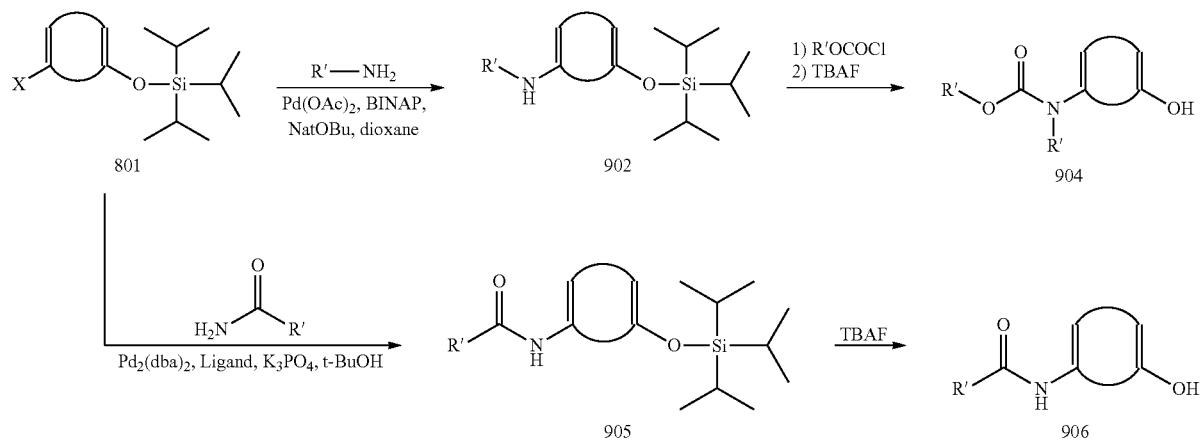

Scheme 10 shows the chemical reactions that can be done on the photochromic dichroic dye. A''' is a simplified representation of 606 from Scheme 6. Scheme 10 demonstrates how to convert —X to -Q''' groups such as cyano, aldehyde, carboxylic acid, and optionally substituted chiral or achiral groups selected from imine, alkoxycarbonyl, aminocarbonyl and aryloxycarbonyl at the described position. The cyanation and oxidation methods have been described in U.S. Patent Pub. No. 2009/0309076A1, wherein these cyanation and oxidation methods are incorporated herein by reference.

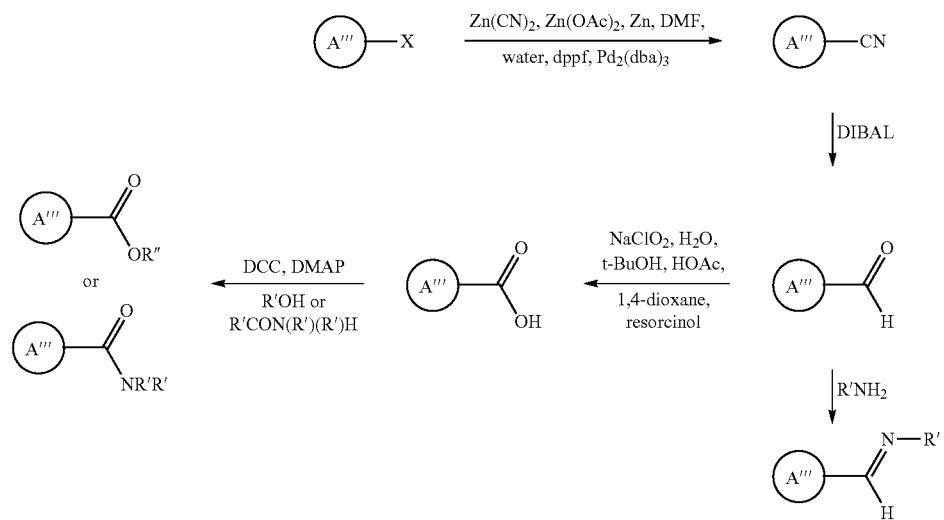

Schemes 1 to 5 have a halogen (X) incorporated into the starting materials and intermediates before formation of the indenofused ring. Also all non-halogen Q's in Schemes 6 to 10, are prepared either directly or indirectly through halogen intermediates. Scheme 11 represents a method of incorporating X after formation of the indenofused ring structure. Scheme 11 also demonstrates the formation of Q' without going through starting materials or intermediates that include halogen X.

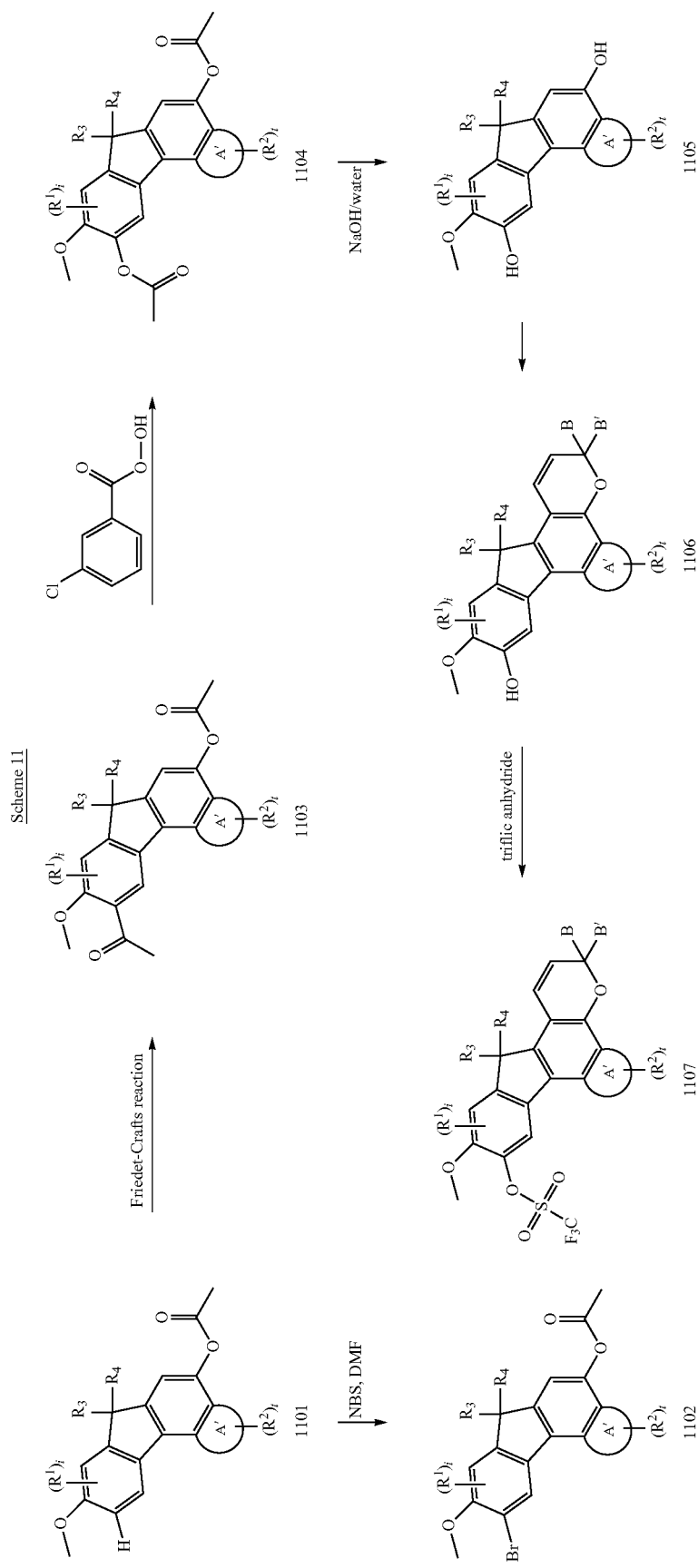

Compound 1101 can be prepared using Scheme 5 as well as other schemes. Compared with the indenofused ring compounds described in the other Schemes herein, Compound 1101 does not have a Q' group attached thereto. The methoxy group in the structure is not limited to methoxy, and can be replaced with other electron donating groups, such as other alkoxy groups, substituted amino groups and alkyl groups. When treated with N-Bromosuccinimide in DMF, the desired position is brominated selectively to provide 1102. A Friedel-Crafts reaction can result in the formation or attachment of a Q' group, such as acetyl, at the desired position, so as to provide 1103. Q' can be converted to other Q' groups in either the pre-pyran stage or pyran stage as shown in Scheme 11. For example, a Baeyer-Villiger reaction can be used to convert the acetyl of 1103 to the ester of 1104. The ester groups of 1104 can be subjected to hydrolysis resulting in formation of the hydroxy groups of 1105. When the pyran ring of 1106 is formed, the hydroxyl at the Q' position of 1105 is not affected and is present in 1106. The same hydroxy is converted to triflate by reaction with triflic anhydride in the presence of a base, such as triethylamine. All compounds from 1103 to 1107 are prepared without going through one or more halogenated intermediates, in contrast to Schemes 1 to 10.

The present invention is more particularly described in the following examples, which are intended to be illustrative only, since numerous modifications and variations therein will be apparent to those skilled in the art. Unless otherwise specified, all parts and all percentages are by weight.

EXAMPLES

Part 1 describes the preparation of Examples 1-21 and 23-27 corresponding to the naphthols and Examples 1A-5A, 9A, 10A, 13A-22A, 27A and 28A corresponding to the indenonaphthopyran. Part 2 describes the testing of the photochromic properties of the Examples 2A-5A, 10A, 13A, 18A-22A, 27A and 28A.

In the examples below, the following abbreviations have the following meanings. If an abbreviation is not defined, it has its generally accepted meaning.

BINAP=2,2'-bis(diphenylphosphino)-1,1'-binaphthyl
Bi(OTf)$_3$=bismuth triflate
CuI=copper iodide
DHP=3,4-dihydro-2H-pyran
DCC=dicyclohexylcarbodlimide
DCM=dichloromethane
DBSA=dodecylbenzenesulfonic acid
DIBAL=diisobutylaluminium hydride
DMAP=4-dimethylaminopyridine
DME=dimethyl ether
DMF=N,N-dimethylformamide
DMSO=dimethylsulfoxide
Dppf=1,1'-bis(diphenylphosphino)ferrocene
EtMgBr=ethyl magnesium bromide
Et$_2$O=diethylether
g=gram
h=hour
HPLC=high-performance liquid chromatography
(iPr)$_2$NH diisopropyl amine
HOAc=acetic acid
LDA=lithium diisopropylamide
KMnO$_4$=potassium permanganate
M=molar (molarity)
mCPBA=meta-Chloroperoxybenzoic acid
MeLi=methyl lithium
mg=milligram
min=minutes
mL=milliliter
mmol=millimoles
mM=millimolar
NatOBu=sodium tert-butoxide
N=normal (normality)
ng=nanogram
nm=nanometer
nM=nanomolar
NMP=N-methylpyrrolidone
NMR=nuclear magnetic resonance
Pd(OAc)$_2$=palladium acetate
Pd$_2$(dba)$_3$=tris(dibenzylideneacetone)dipalladium(0)
PPh$_3$=triphenyl phosphine
PPTS=pyridine p-toluenesulfonate
pTSA=p-toluenesulfonic acid
PdCl$_2$(PPh$_3$)$_2$=bis(triphenylphosphine)palladium(II) chloride
PBS=phosphate buffered saline
TBAF=Tetra-n-butylammonium fluoride
THF=tetrahyrdofuran
TLC=thin layer chromatography
t-BuOH=t-butanol
(Tf)$_2$O=trifluoromethanesulfonic acid anhydride
μL=microliter
μM=micromolar
Zn(OAc)$_2$=zinc acetate
Zn(CN)$_2$=Zinc cyanide Part 1

Preparation of Examples

Example 1

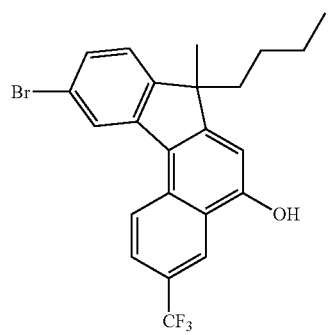 [SMILES: CCCCC1(C)c2ccc(Br)cc2-c2c1cc(O)c1cc(C(F)(F)F)ccc21]

Step 1

A mixture of 4-bromoacetophenone (148 g), dimethyl succinic ester (130 g) and toluene (2.5 L) was mechanically stirred in a suitable reaction flask. Potassium t-butoxide (100 g) was added in one portion and a precipitate formed. After mixing one hour, water (1 L) was added. The recovered aqueous layer was washed with toluene (200 ml) twice and acidified by 12 N HCl to pH of 2. The product was extracted with ethyl acetate and then recrystallized from a mixture of ethyl ether/hexanes (1/1). White crystals (170 g) were obtained. NMR indicated that the product had a structure consistent with (E)-4-(4-bromophenyl)-3-(methoxycarbonyl)pent-3-enoic acid.

Step 2

The product from Step 1 (160 g) was mixed with 50 wt % sodium hydroxide water solution (200 g) and water (4 liters) in a four liter beaker. The mixture was heated to boil and after one hour later the pH of the solution was adjusted to about 2 using 12 N HCl. The resulting precipitate was collected by filtration. Off-White crystals (152 grams) were obtained. NMR indicated that the product had a structure consistent with (E)-2-(1-(4-bromophenyl)ethylidene)succinic acid.

Step 3

A mixture of the product from Step 2 (152 g), DBSA (5 g) and toluene (1 L) was added to a reaction flask and heated up to reflux with water removal using a Dean-Stark trap, for two hours. The resulting mixture was passed through a silica gel plug column and washed off the plug column with 2/8 (v/v) ethyl aceate/hexanes, and concentrated. The type of silica gel used in this and other examples was Grade 60, 230-400 mesh. To the resulting oil, hexanes (1 L) was added. The product crystallized and was collected by filtration and dried under vacuum. Off-white crystals (130 grams) were obtained. NMR indicated that the product had a structure consistent with (E)-3-(1-(4-bromophenyl)ethylidene)dihydrofuran-2,5-dione.

Step 4

To a stirred mixture of the aluminum chloride (130 g) and methylene chloride (1 L), the product from Step 3 (125 g) was added in three portions over a 5 minute interval. After stirring at room temperature for 2 hours, HPLC showed that reaction was completed with the formation of two products. The reaction mixture was poured slowly into water (2 L). Smoke generation was observed. A large amount of yellow solid formed. THF (1 L) was added to the mixture to dissolve the yellow solid. The water layer was saturated with solid NaCl and then removed by a separatory funnel. The recovered organic layer was dried over magnesium sulfate and concentrated. Ethyl acetate (200 mL) was added and the yellow crystals that formed were collected and dried (50 grams). NMR indicated that the product had a structure consistent with 2-(6-bromo-3-methyl-1-oxo-1H-inden-2-yl)acetic acid.

Step 5

A reaction flask containing a mixture of manganese chloride (7.46 g) and lithium chloride (5 g) was dried at 200° C. in a vacuum oven for an hour. Under the protection of nitrogen, THF was added (200 mL). After 30 minutes, copper (I) chloride (0.59 g) and the product from Step 4 (19.4 g) were added. The mixture was stirred until clear and cooled to 0° C. To the resulting mixture, a 2M THF solution of butyl magnesium bromide (99 mL) was added dropwise over 2 hours. After the addition, the mixture was stirred at 0° C. for 2 hours and water (200 mL) was added. The pH of the mixture was adjusted to ~2 using 12 N HCl. Ethyl acetate (200 mL) was added. The recovered organic portion was dried, and concentrated. The product was purified by CombiFlash® Rf from Teledyne ISCO. Oil (4 g) was obtained as the product. NMR indicated that the product had a structure consistent with 2-(5-bromo-1-butyl-1-methyl-3-oxo-2,3-dihydro-1H-inden-2-yl)acetic acid.

Step 6

Solid magnesium (1.5 g) was placed in a reaction flask equipped with a dropping funnel and dried in an oven. THF (60 mL) and 1-bromo-4-trifluoromethylbenzene (15.3 g) were added. With the initiation of one drop of 1,2-dibromoethane, Grignard reagent started to form. An ice bath was used to control the temperature around room temperature. After two hours a solution of the product from Step 5 (4.2 g) in anhydrous THF (20 mL) was put into the dropping funnel and added to the reaction mixture over a 10 minute interval. After the addition, the mixture was stirred at room temperature for 2 hours and water (100 mL) was added. The pH was adjusted to about 2 using 12 N HCl. Ethyl acetate (100 mL) was added and the resulting organic phase was collected by a separatory funnel, washed with NaCl/water, dried over magnesium sulfate and concentrated. The obtained oil was re-dissolved in toluene (100 mL) in a reaction flask. Acetic anhydride (10 grams) and bismuth triflate (0.5 g) was added. The mixture was refluxed for 1 hour and cooled to room temperature. Methanol (100 mL) and 12 N HCl (1 mL) was added. The mixture was refluxed for 12 hours. All the solvent was removed. A silica gel plug column separation was applied to the crude product. Oil (3 g) was obtained as the product. NMR indicated that the product had a structure consistent with 10-bromo-7-butyl-7-methyl-3-(trifluoromethyl)-7H-benzo[c]fluoren-5-ol.

Example 1A

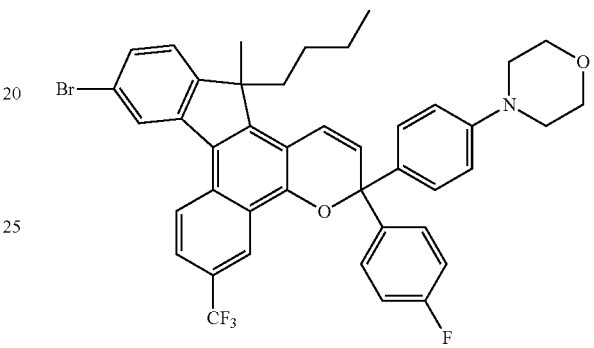

The product from Step 6 (3 g) of Example 1 was placed in a reaction flask. To the flask, 1-(4-fluorophenyl)-1-(4-(N-morpholino)phenyl)prop-2-yn-1-ol (2.1 g), 1,2-dichloroethane (30 mL) and p-toluenesulfonic acid (70 mg) were added. The mixture was refluxed for 4 hours. All solvent was removed. A silica gel plug column was used to purify the product. A brownish oil (2 grams) was obtained as the product. NMR indicated that the product had a structure consistent with 3-(4-fluorophenyl)-3-(4-(N-morpholino)phenyl)-10-bromo-6-trifluoromethyl-13-methyl-13-butyl-3,13-dihydro-indeno[2',3':3,4]naphtho[1,2-b]pyran.

Example 2

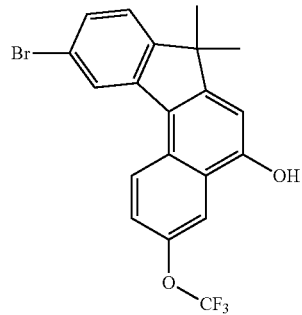 [SMILES: CC1(C)c2ccc(Br)cc2-c2c1cc(O)c1cc(OC(F)(F)F)ccc21]

The procedures from Example 1 were followed except that: in Step 5, 1.4 M THF solution of methyl magnesium bromide was used in place of butyl magnesium bromide; and in Step 6, 1-bromo-4-trifluoromethoxybenzene was used in place of 1-bromo-4-trifluoromethylbenzene. NMR indicated that the product had a structure consistent with 10-bromo-7,7-dimethyl-3-(trifluoromethoxy)-7H-benzo[c]fluoren-5-ol.

Example 2A

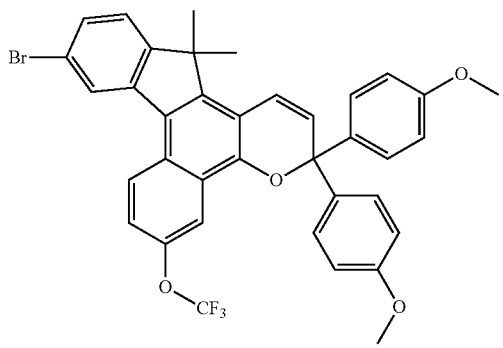 [SMILES: COc1ccc(C2(c3ccc(OC)cc3)C=Cc3c4c(c5ccc(OC(F)(F)F)cc5c3O2)-c2cc(Br)ccc2C4(C)C)cc1]

The procedures from Example 1A were followed except that: 10-bromo-7,7-dimethyl-3-(trifluoromethoxy)-7H-benzo[c]fluoren-5-ol from Example 2 was used in place of 10-bromo-7-butyl-7-methyl-3-(trifluoromethyl)-7H-benzo[c]fluoren-5-ol; 1,1-bis(4-methoxyphenyl)prop-2-yn-1-ol was used in place of 1-(4-fluorophenyl)-1-(4-(N-morpholino)phenyl)prop-2-yn-1-ol. NMR indicated that the product had a structure consistent with 3,3-bis(4-methoxyphenyl)-10-bromo-6-trifluoromethoxy-13,13-dimethyl-3,13-dihydro-indeno[2',3':3,4]naphtho[1,2-b]pyran.

Example 3

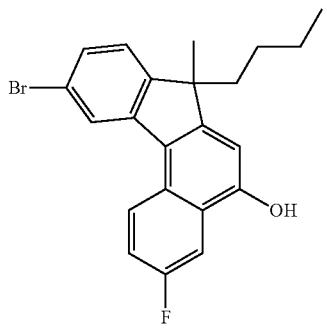 [SMILES: CCCCC1(C)c2ccc(Br)cc2-c2c1cc(O)c1cc(F)ccc21]

The procedures from Example 1 were followed except that in Step 6, 1-bromo-4-fluorobenzene was used in place of 1-bromo-4-trifluoromethylbenzene. NMR indicated that the product had a structure consistent with 10-bromo-7-butyl-3-fluoro-7-methyl-7H-benzo[c]fluoren-5-ol.

Example 3A

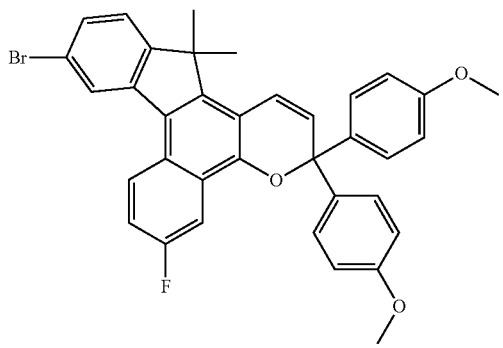 [SMILES: COc1ccc(C2(c3ccc(OC)cc3)C=Cc3c4c(c5ccc(F)cc5c3O2)-c2cc(Br)ccc2C4(C)C)cc1]

The procedures from Example 1A were followed except that: 10-bromo-7-butyl-3-fluoro-7-methyl-7H-benzo[c]fluoren-5-ol from Example 3 was used in place of 10-bromo-7-butyl-7-methyl-3-(trifluoromethyl)-7H-benzo[c]fluoren-5-ol; 1,1-bis(4-methoxyphenyl)prop-2-yn-1-ol was used in place of 1-(4-fluorophenyl)-1-(4-(N-morpholino)phenyl)prop-2-yn-1-ol. NMR indicated that the product had a structure consistent with 3,3-bis(4-methoxyphenyl)-10-bromo-6-fluoro-13-methyl-13-butyl-3,13-dihydro-indeno[2',3':3,4]naphtho[1,2-b]pyran.

Example 4

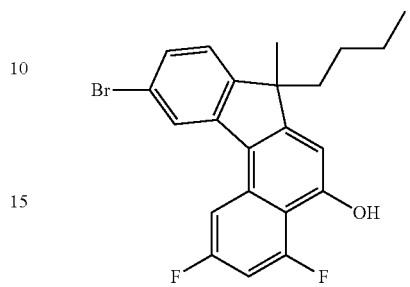

The procedures from Example 1 were followed except that in Step 6, 1-bromo-3,5-difluorobenzene was used in place of 1-bromo-4-trifluoromethylbenzene. NMR indicated that the product had a structure consistent with 10-bromo-7-butyl-2,4-difluoro-7-methyl-7H-benzo[c]fluoren-5-ol.

Example 4A

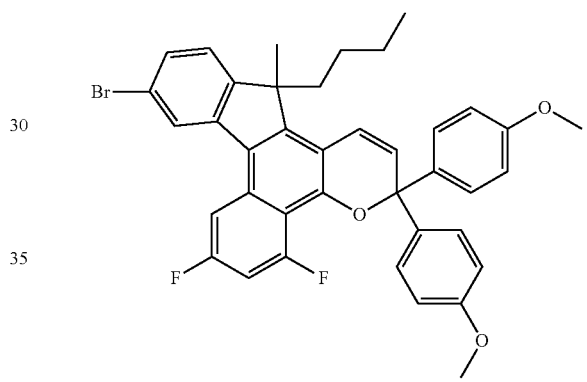

The procedures from Example 1A were followed except that: 10-bromo-7-butyl-2,4-difluoro-7-methyl-7H-benzo[c]fluoren-5-ol from Example 4 was used in place of 10-bromo-7-butyl-7-methyl-3-(trifluoromethyl)-7H-benzo[c]fluoren-5-ol; 1,1-bis(4-methoxyphenyl)prop-2-yn-1-ol was used in place of 1-(4-fluorophenyl)-1-(4-(N-morpholino)phenyl)prop-2-yn-1-ol. NMR indicated that the product had a structure consistent with 3,3-bis(4-methoxyphenyl)-10-bromo-5,7-difluoro-13-methyl-13-butyl-3,13-dihydro-indeno[2',3':3,4]naphtho[1,2-b]pyran.

Example 5

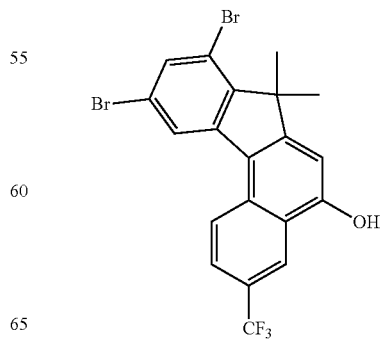

Step 1

A 2 L flask with tribromobenzene (100 g) and a magnetic stir bar was dried in a vacuum oven at 80° C. for 4 hours, Dry THF (500 ml) was added. The resulting mixture was placed in an NaCl saturated ice bath. 3M Isopropyl magnesium chloride (160 ml) was added drop wise to the solution at a rate so that the inside temperature was controlled to −20 to 0° C. The addition was finished in about 30 minutes to 1 hour. The mixture was stirred for half an hour at the same temperature and bis[2-(N,N-dimethylamino)ethyl]ether (61 g) was added slowly over a 5 minutes interval and a large amount of precipitate formed. The resulting mixture was stirred for 20 more minutes and a mixture of 4-trifluoromethylbenzoyl chloride (73 g) and THF (100 ml) was added over a 5 minute interval. The resulting mixture was stirred overnight. Water (100 ml) was added slowly and the pH was adjusted to 2 with 3N HCl. The organic layer was collected by a separatory funnel, washed with 5% NaOH/water and NaCl/water, dried and concentrated. To the recovered oil, methanol (300 ml) was added and the product crystallized. The product was collected by filtration. NMR showed that the obtained white crystals (87 g) have a structure consistent with 3,5-dibromo-4'-trifluoromethylbenzophenone.

Step 2

A mixture of 3,5-dibromo-4'-trifluoromethylbenzophenone (75 g) from Step 1, dimethyl succinic ester (32.2 g) and toluene (800 ml) were placed in a three neck 5 L flask equipped with a mechanical stir. Solid of potassium t-butoxide (22.6 g) was added batchwise over a 30 minute interval. An exothermic reaction along with the formation of a large amount of precipitate was observed. After two hours, water (500 ml) was added and a milky mixture was obtained. The pH of the mixture was adjusted to ~2 using 3 N HCl. After stirring at room temperature for 10 minutes, the organic layer was collected, washed with NaCl/HCl, dried over MgSO4. After concentration, hexanes were added and white crystals formed. The crystals were collected by filtration. NMR showed that the obtained product (62 grams) had a structure consistent with (E)-4-(3,5-dibromophenyl)-3-(nnethoxycarbonyl)-4-(4-(trifluoromethyl)phenyl)but-3-enoic acid.

Step 3

Solid anhydrous lanthanum (III) chloride (100 g) was ground to a very fine powder and then mixed with lithium chloride (52 g) and dry THF (1 liter) in a 5 liter three-neck flask equipped with a mechanical stir and a dropping funnel. The mixture was refluxed for few hours until it dissolved. Solid (E)-4-(3,5-dibromophenyl)-3-(methoxycarbonyl)-4-(4-(trifluoromethyl)phenyl)but-3-enoic acid (106 g) from Step 2 was dissolved in the mixture. The mixture was then cooled to −15° C. A solution of 3M methyl magnesium chloride (238 ml) was placed in the dropping funnel. The first 30% of the Grignard was added slowly to the mixture. Generation of gas bubbles was observed. After the temperature returned to −15° C., the remainder of the Grignard was added to the mixture in 2 minutes. After 30 minutes, water (1 L) was added slowly to the mixture and the pH was adjusted to acidic using acetic acid. The mixture turned clear with formation of two layers. Water layer was drained off. Organic layer was washed with NaCl/water four times and then concentrated to dry. A light yellowish solid was recovered and dissolved in toluene. The solution was filtered using a silica gel plug column and the recovered clear solution was concentrated to dryness. White solid product was obtained and used in the next Step without further purification. A portion of the product was recrystallized from methanol and NMR analysis showed that the purified crystals had a structure consistent with (E)-4-((3,5-dibromophenyl)(4-(trifluoromethyl)phenyl)methylene)-5,5-dimethyldihydrofuran-2(3H)-one.

Step 4

Into a reaction flask was added the product from Step 3, toluene (500 ml), bismuth triflate (20 g) and acetic acid (0.24 g). The resulting mixture was stirred at reflux for 1 hour. After it cooled to room temperature, acetic anhydride (100 ml) was added. The mixture was heated to reflux again and after one hour, the mixture was cooled to room temperature and filtered through a silica gel plug column. The recovered clear solution was concentrated to dryness. Acetone (50 ml) was added to the obtained solid to form a slurry and methanol (250 ml) was subsequently added. The resulting mixture was cooled to form crystals. The recovered white crystals (58 g) were analyzed by NMR which showed that the product had a structure consistent with 8,10-dibromo-7,7-dimethyl-3-(trifluoromethyl)-7H-benzo[c]fluoren-5-yl acetate.

Step 5

To a flask containing 8,10-dibromo-7,7-dimethyl-3-(trifluoromethyl)-7H-benzo[c]fluoren-5-yl acetate (2.42 g) from Step 4 was added methanol (20 mL) and tetrahydrofuran (10 mL). Concentrated hydrochloric acid (1 mL) was added and the solution was heated to reflux for 4 h. The solvent was removed under vacuum and the residue was purified by filtration through a plug of silica gel, using 4:1 hexane/ethyl acetate mixture as the eluent. Fractions containing the desired material were grouped and concentrated to provide a cream colored solid (1.63 g). NMR analysis of the cream colored solid indicated a structure that was consistent with 8,10-dibromo-7,7-dimethyl-3-(trifluoromethyl)-7H-benzo[c]fluoren-5-ol.

Example 5A

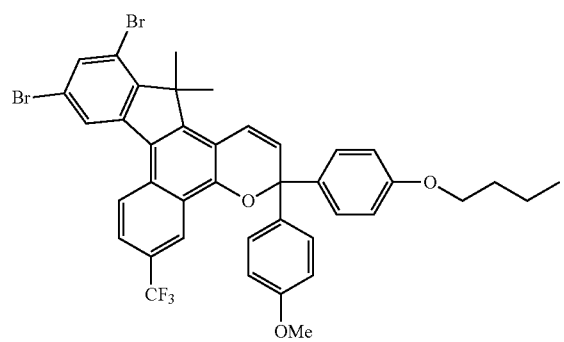 [SMILES: CCCCOc1ccc(C2(c3ccc(OC)cc3)C=Cc3c4c(c5ccc(C(F)(F)F)cc5c3O2)-c2cc(Br)cc(Br)c2C4(C)C)cc1]

To a chloroform solution (100 mL) of the product from Step 5 of Example 5, (36.24 g) was added 1-(4-butoxyphenyl)-1-(4-methoxyphenyl)prop-2-yn-1-ol (28.00 g) and 4-dodecylbenzenesulfonic acid (2.40 g). The solution was heated to reflux for 8 h. The reaction mixture was concentrated under reduced pressure to provide an oily residue. The residue was purified by column chromatography using 9:1 hexane ethyl acetate mixtures as the eluant. Fractions containing the desired material were grouped and concentrated to an oily residue. The residue was re-crystallized from dichloromethane and methanol. The crystals were collected by vacuum filtration and dried to provide a grey solid (20.00 g). NMR analysis of the grey solid indicated a structure that was consistent with 3-(4-butoxyphenyl)-3-(4-methoxyphenyl)-10,12-dibromo-6-trifluoromethyl-13,13-dimethyl-3,13-dihydro-indeno[2',3':3,4]naphtho[1,2-b]pyran.

Example 6

8,10-Dibromo-7,7-dimethyl-3-(trifluoromethyl)-7H-benzo[c]fluoren-5-yl acetate (53.88 g) from Step 4 of Example 5 and 4'-(4-trans-pentylcyclohexyl)-N-(4-(4,4,5,5-tetramethyl-1,3,2-dioxaborolan-2-yl)phenyl)-[1,1'-biphenyl]-4-carboxamide (56.27 g) were dissolved in a reaction flask containing a 1:1 mixture of toluene (1000 mL) and ethanol (1000 mL). Potassium carbonate (42.26 g) and triphenylphosphine (8.02 g) were added and the solution was degassed by bubbling nitrogen for 20 min. Palladium acetate (2.29 g) was added and the mixture was heated to reflux for 3 h. The reaction mixture was cooled to room temperature and a degassed suspension of bis(triphenylphosphine)palladium (II) chloride (7.15 g) in toluene (100 mL) and ethanol (100 mL) was added. The reaction mixture was heated to reflux for 16 h. The reaction mixture was cooled to room temperature and diluted with ethyl acetate (500 mL). The mixture was filtered through a bed of CELITE® filter aid and the filtrate was collected and concentrated in vacuo to provide a residue. The residue was purified by column chromatography using 19:1 toluene and ethyl acetate mixture as the eluant. Fractions that contained the desired product were grouped and concentrated in vacuo to provide a cream colored residue. Toluene was added to the residue to precipitate the product. The resulting precipitate was collected by vacuum filtration and dried to provide a cream colored solid (32 g). NMR analysis of the cream colored solid indicated a structure that was consistent 7,7-dimethyl-3-trifluoromethyl-10-[4-(4-(4-(4-trans-pentylcyclohexyl)phenyl)benzamido)phenyl]-7H-benzo[c]fluoren-5-ol.

Example 7

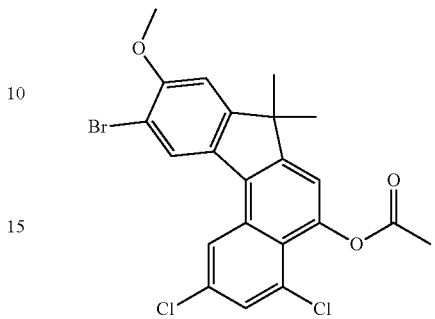

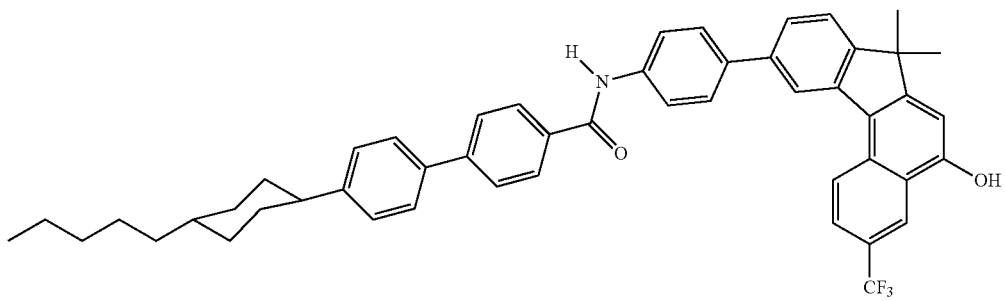 [SMILES: CCCCCC1CCC(c2ccc(-c3ccc(C(=O)Nc4ccc(-c5ccc6c(c5)-c5c(cc(O)c7cc(C(F)(F)F)ccc57)C6(C)C)cc4)cc3)cc2)CC1]

Step 1 to Step 4

Procedures from Steps 1 to 4 of Example 5 were followed except that in Step 1,3,5-dichlorobromobenznene and 4-methoxybenzoyl chloride was used in place of tribromobenzene and 4-trifluoromethylbenzoyl chloride. An off-white solid was obtained as the product. NMR indicated that the product had a structure consistent with 2,4-dichloro-9-methoxy-7,7-dimethyl-7H-benzo[c]fluoren-5-yl acetate.

Step 5

A mixture of the product from Step 4 (5 g), NBS (2.7 g) and DMF (100 mL) was stirred in a reaction flask and heated to 90° C. Two hours later, the reaction mixture was poured into water (400 mL) and extracted with 1/1 ethyl acetate/THF (200 mL). The organic layer was collected, washed with sodium bisulfite water solution three times, dried and concentrated. To the recovered product, methanol (100 mL) was added. After filtration, an off white solid (4.4 g) was obtained as the product. NMR indicated that the product had a structure consistent with 10-bromo-2,4-dichloro-9-methoxy-7,7-dimethyl-7H-benzo[c]fluoren-5-yl acetate.

Example 8

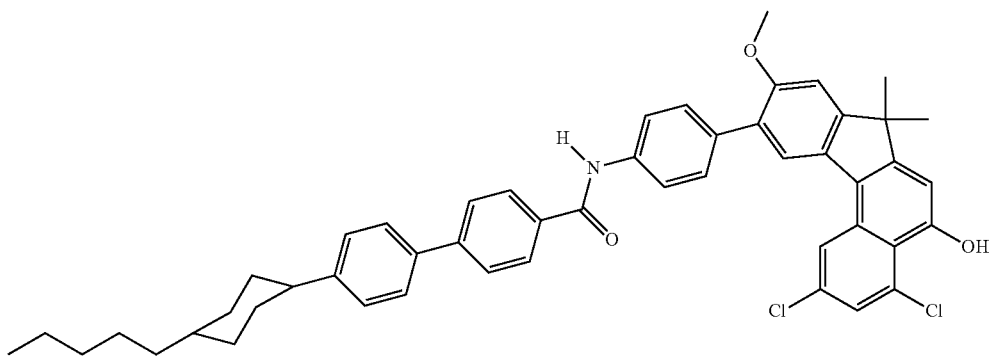 [SMILES: CCCCCC1CCC(c2ccc(-c3ccc(C(=O)Nc4ccc(-c5cc6c(cc5OC)C(C)(C)c5cc(O)c7c(Cl)cc(Cl)cc7c5-6)cc4)cc3)cc2)CC1]

A mixture of the product of Example 7, 10-bromo-2,4-dichloro-9-methoxy-7,7-dimethyl-7H-benzo[c]fluoren-5-yl acetate (4.3 g), 4'-(4-trans-pentylcyclohexyl)-N-(4-(4,4,5,5-tetramethyl-1,3,2-dioxaborolan-2-yl)phenyl)-[1,1'-biphenyl]-4-carboxamide (4.94 g), sodium carbonate (4 g), THF (200 mL), water (20 mL) and Tetrakis(triphenylphosphine) palladium(0) (1 g) was placed in a reaction flask and degassed by bubbling nitrogen through the mixture for 10 minutes. The mixture was heated to reflux for 17 hours. Potassium carbonate (5 g) and ethanol (50 mL) was added and the resulting mixture was refluxed for 8 hours, extracted using THF and sodium chloride saturated water. The resulting organic layer was collected, washed with 100 mL 1 N HCl three times, washed with 100 mL 1 N sodium sulfite water solution once, washed with sodium chloride saturated water once, dried over magnesium sulfate and concentrated. The recovered residue was dissolved in 10/1 (v/v) toluene/THF (200 mL) and passed through a silica gel plug column which was washed using 10/1 toluene/INF to recover the product. The resulting clear solution was concentrated and added to methanol and stirred for half an hour. The resulting solid was collected and dried to provide an off-white solid (7.5 g) as the product. NMR indicated that the product had a structure consistent with 2,4-dichloro-7,7-dimethyl-9-methox-10-[4-(4-(4-(4-trans-pentylcyclohexyl)phenyl)benzamido)phenyl]-7H-benzo[c]fluoren-5-ol.

Example 9

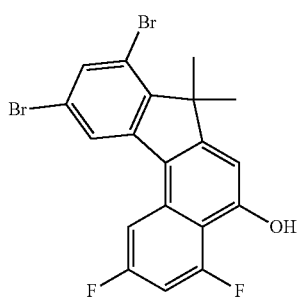 [SMILES: CC1(C)c2cc(O)c3c(F)cc(F)cc3c2-c2cc(Br)cc(Br)c21]

The procedures from Example 5 were followed except that in Step 1,3,5-difluorobenzoyl chloride was used in place of 4-trifluoromethylbenzoyl chloride to produce in Step 5, the desired product which was recrystallized using ethyl acetate as the solvent. NMR indicated that the product had a structure consistent with 8,10-dibromo-2,4-difluoro-7,7-dimethyl-7H-benzo[c]fluoren-5-ol.

Example 9A

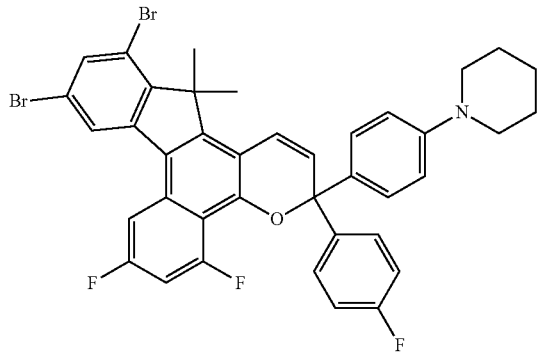 [SMILES: CC1(C)c2c(Br)cc(Br)cc2-c2c1c1c(c3c(F)cc(F)cc23)OC(c2ccc(F)cc2)(c2ccc(N3CCCCC3)cc2)C=C1]

The procedures from Example 1A were followed except that: 8,10-dibromo-2,4-difluoro-7,7-dimethyl-7H-benzo[c]fluoren-5-ol from Example 9 was used in place of 10-bromo-7-butyl-7-methyl-3-(trifluoromethyl)-7H-benzo[c]fluoren-5-ol and 1-(4-fluorophenyl)-1-(4-(N-piperidinyl)phenyl)prop-2-yn-1-ol was used in place of 1-(4-fluorophenyl)-1-(4-(N-morpholino)phenyl)prop-2-yn-1-ol. NMR showed that the product had a structure consistent with 3-(4-fluorophenyl)-3-(4-(N-piperidinyl)phenyl)-10,12-dibromo-5,7-difluoro-13,13-dimethyl-butyl-3,13-dihydro-indeno[2',3':3,4]naphtho[1,2-b]pyran.

Example 10

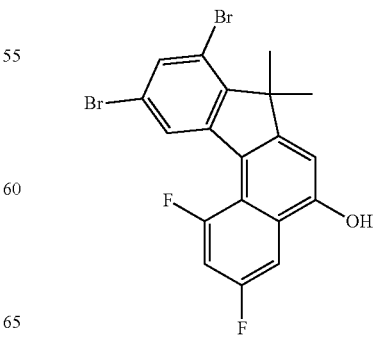

The procedures from Example 5 were followed except that in Step 1,2,4-difluorobenzoyl chloride was used in place of 4-trifluoromethylbenzoyl chloride. NMR analysis indicated that the product had a structure consistent with 8,10-dibromo-1,3-difluoro-7,7-dimethyl-7H-benzo[c]fluoren-5-ol.

Example 10A

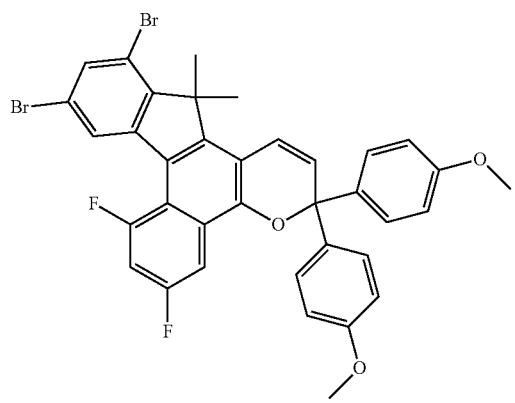 [SMILES: COc1ccc(C2(c3ccc(OC)cc3)C=Cc3c4c(c5c(F)cc(F)cc5c3O2)-c2cc(Br)cc(Br)c2C4(C)C)cc1]

The procedures from Example 1A were followed except that 8,10-dibromo-1,3-difluoro-7,7-dimethyl-7H-benzo[c]fluoren-5-ol was used in place of 10-bromo-7-butyl-7-methyl-3-(trifluoromethyl)-7H-benzo[c]fluoren-5-ol and 1,1-bis(4-methoxyphenyl)prop-2-yn-1-ol was used in place of 1-(4-fluorophenyl)-1-(4-(N-morpholino)phenyl)prop-2-yn-1-ol. NMR showed that the product had a structure consistent with 3,3-bis(4-methoxyphenyl)-10,12-dibromo-6,8-difluoro-13,13-dimethyl-3,13-dihydro-indeno[2',3':3,4]naphtho[1,2-b]pyran.

Example 11

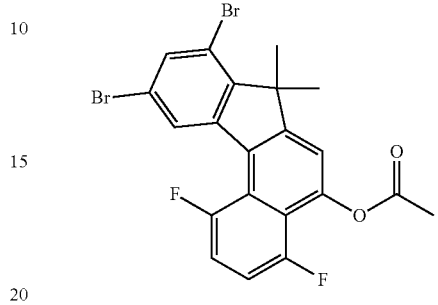

The procedures from Step 1 to Step 4 of Example 5 were followed except that in Step 1, 2,5-difluorobenzoyl chloride was used in place of 4-trifluoromethylbenzoyl chloride. NMR analysis indicated that the product had a structure consistent with 8,10-dibromo-1,4-difluoro-7,7-dimethyl-7H-benzo[c]fluoren-5-yl acetate.

Example 12

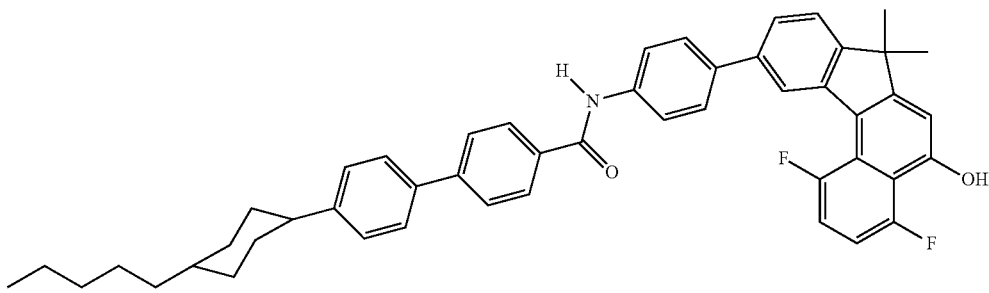 [SMILES: CCCCCC1CCC(c2ccc(-c3ccc(C(=O)Nc4ccc(-c5ccc6c(c5)-c5c(cc(O)c7c(F)ccc(F)c57)C6(C)C)cc4)cc3)cc2)CC1]

Procedures Example 6 were followed except that 8,10-dibromo-1,4-difluoro-7,7-dimethyl-7H-benzo[c]fluoren-5-yl acetate was used in place of 8,10-Dibromo-7,7-dimethyl-3-(trifluoromethyl)-7H-benzo[c]fluoren-5-yl acetate. NMR analysis of the solid indicated a structure consistent with 7,7-dimethyl-1,4-difluoro-10-[4-(4-(4-(4-trans-pentylcyclohexyl)phenyl)benzamido)phenyl]-7H-benzo[c]fluoren-5-ol.

Example 13

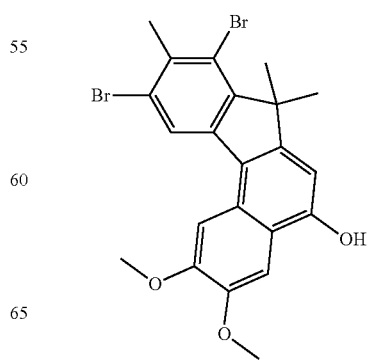

Step 1

Magnesium (3.9 g) and THF (50 mL) was placed in a dry flask equipped with a dropping funnel, which contained a THF (800 mL) solution of 2,4,6-tribromotoluene (53 g). One tenth of the THF solution in the dropping funnel was added to the flask and the reaction flask started to boil. The reaction flask was placed in an ice bath was applied and the reaction mixture was maintained at 0° C. and the remainder of the solution in the dropping funnel was added drop wise over a half an hour. After stirring 1.5 h, bis[2-(N,N-dimethylamino) ethyl]ether (28.4 g) was added. After stirring for one hour, 3,4-dimethoxybenzoyl chloride (35.5 g) was added in one portion. The resulting mixture was stirred overnight, water (500 mL) was added to the mixture and 12N HCl was used to adjust pH to ~2. DCM was added to the mixture (500 mL) and the resulting organic layer was collected, washed with water once, washed with sodium bicarbonate once, dried over magnesium sulfate and concentrated. A yellow oil (65 g) was obtained. The oil was used directly in the next step.

Step 2

The product from Step 1 (65 g), dimethyl succinate (30 g) and toluene (500 mL) were added to a reaction flask equipped with a mechanical stirrer, a dropping funnel and a nitrogen blanket. The mixture was stirred at room temperature until the solids were dissolved. A toluene solution of potassium t-pentoxide (25 wt %, 87.4 g) was added through a dropping funnel and the mixture was stirred at room temperature for 2 hours. The resulting reaction mixture was poured into 1 L of water and the aqueous layer, which contained the product, was collected. The toluene layer was extracted with 200 mL water. The combined water extracts was washed with toluene. HCl (12 N) was added to the water extracts until pH was adjusted to 5. A yellow oil precipitated. The resulting mixture was extracted with ethyl acetate, dried over magnesium sulfate, concentrated and dried in vacuum. A yellow glassy oil (35 g) was obtained as product. It was used directly in the next step.

Step 3

A mixture of the Stobbe acid products from Step 2 (35 g), bismuth triflate (2.1 g), dichloromethane (200 mL) and acetic anhydride (27 g) was mixed and stirred at room temperature in a reaction flask for one hour. The resulting mixture was concentrated by vacuum evaporation and methanol (500 mL) and HCl (12 N, 2 mL) were added. The resulting mixture was refluxed for 4 hours and concentrated to provide an oil. The oil was passed through a silica gel plug column separation followed by recrystallization from 2/8 (v/v) ethyl acetate/hexane. White crystals (5 g) were obtained as the product. NMR indicated that the product had a structure consistent with methyl 1-(3,5-dibromo-4-methylphenyl)-4-hydroxy-6,7-dimethoxy-2-naphthoate.

Step 4

The product from Step 3 (1.5 g) was dissolved in 30 mL of anhydrous THF in an oven dried flask equipped with a dropping funnel and a magnetic stir bar. The mixture was stirred at room temperature, and 7 mL 3 M THF solution of methyl magnesium bromide was added dropwise. After the addition, the mixture was stirred at room temperature for overnight. The reaction mixture was then poured into 100 mL water. The pH value of the mixture was adjusted to ~5 using HCl (12 N). Ethyl acetate (100 mL) was added. The resulting organic layer was separated, dried over magnesium sulfate, concentrated and dried in vacuum. The recovered white solid (1.5 g) was used directly in the next step.

Step 5

The product from Step 4 (1.5 g), toluene (100 mL) and bismuth triflate (0.04 g) were added to a reaction flask equipped with a magnetic stir bar. The resulting mixture was refluxed for 4 hours. The reaction mixture was passed through a silica gel plug column. After concentration, white solid (0.8 g) was obtained. NMR indicated that the white solid had a structure consistent with 8,10-dibromo-2,3-dimethoxy-7,7,9-trimethyl-7H-benzo[c]fluoren-5-ol.

Example 13A

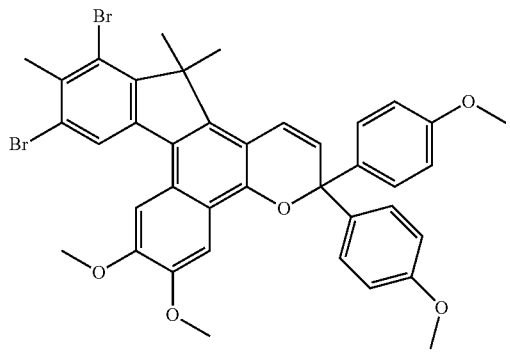 [SMILES: COc1ccc(C2(c3ccc(OC)cc3)C=Cc3c4c(c5cc(OC)c(OC)cc5c3O2)-c2cc(Br)c(C)c(Br)c2C4(C)C)cc1]

To a reaction flask containing a toluene solution (20 ml) of the product from Example 13 (0.8 g) 1,1-bis(4-methoxyphenyl)prop-2-yn-1-ol (0.8 g) and a few crystals of p-toluene sulfonic acid were added. After stirring for one hour at room temperature, all solvent was evaporated. The recovered product was purified by CombiFlash®Rf followed by recrystallization from ether ether. White crystals (0.95 g) were obtained as the product. NMR indicated that the product had a structure consistent with 3,3-bis(4-methoxyphenyl)-10,12-dibromo-6,7-dimethoxy-11,13,13-trimethyl-3,13-dihydro-indeno[2',3':3,4]naphtho[1,2-b]pyran.

Example 14A

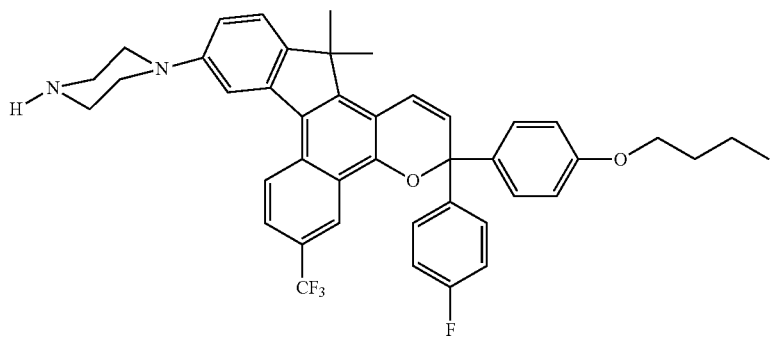 [SMILES: CCCCOc1ccc(C2(c3ccc(F)cc3)C=Cc3c4c(c5ccc(C(F)(F)F)cc5c3O2)-c2cc(N3CCNCC3)ccc2C4(C)C)cc1]

Step 1

To a mixture of degassed dioxane (100 mL) and toluene (100 mL) in a reaction flask was added 2,2'-bis(diphenylphosphino)-1,1'-binaphthyl (1.20 g) and palladium (II) acetate (0.30 g). The product from Step 4 of Example 5, 8,10-dibromo-7,7-dimethyl-3-(trifluoromethyl)-7H-benzo[c]fluoren-5-yl acetate (5.10 g) was added followed by 1-formylpiperazine (2.80 g) under a stream of nitrogen. Sodium Pert-butoxide (2.80 g) was added and the solution was heated to reflux for 22 h. The reaction mixture was cooled to room temperature and diluted with tetrahydrofuran. The solution was filtered through a bed of CELITE® filter aid and the filtrate was concentrated under vacuum. The residue was purified by column chromatography using 1:4 (v:v) methylene chloride and ethyl acetate mixtures as the eluant. Fractions containing the desired material were grouped and concentrated. The residue (1.25 g) was used directly for the next step. NMR analysis of the residue indicated a structure that was consistent with 4-(8-bromo-5-hydroxy-7,7-dimethyl-3-(trifluoromethyl)-7H-benzo[c]fluoren-10-yl)piperazine-1-carbaldehyde.

Step 2

The product of Step 1, (0.69 g) and 1-(4-butoxyphenyl)-1-(4-fluorophenyl)prop-2-yn-1-ol (0.60 g) were dissolved in 1,2-dichloroethane (20 mL) in a reaction flask. p-Toluenesulfonic acid (0.1 g) was added and the solution was heated to reflux for 18 h. The reaction mixture was cooled to room temperature and the solvent was removed in vacuo. The residue was purified by column chromatography using 1:1 hexanes and dichloromethane mixtures as the eluant. Fractions containing the desired material were grouped and concentrated. The residue (0.75 g) was used directly in the next step.

Step 3

The product of Step 2 (2.00 g) was dissolved in dioxane (30 mL) in a reaction flask. 10% HCl aq (5 mL) was added and the solution was heated to reflux for 2 h. The reaction mixture was cooled to room temperature and poured into a saturated aqueous sodium bicarbonate solution (300 mL). The recovered aqueous layer was extracted with ethyl acetate (300 mL). The ethyl acetate solution was dried with anhydrous sodium sulfate, filtered and concentrated to provide a residue. The residue was purified by column chromatography using 1:1 (v:v) ethyl acetate and methanol mixture as the eluant. Fractions containing the desired material were grouped and concentrated. The residue was collected as the product. NMR indicated that the structure was consistent with 3-(4-fluorophenyl)-3-(4-butoxyphenyl)-10-(piperazin-1-yl)-6-trifluoromethyl-13,13-dimethyl-3,13-dihydro-indeno[2',3':3,4]naphtho[1,2-b]pyran.

Example 15A

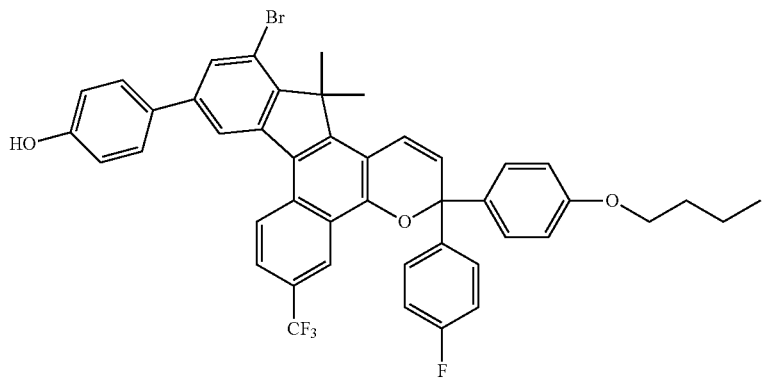 [SMILES: CCCCOc1ccc(C2(c3ccc(F)cc3)C=Cc3c4c(c5ccc(C(F)(F)F)cc5c3O2)-c2cc(-c3ccc(O)cc3)cc(Br)c2C4(C)C)cc1]

Step 1

The procedure from Example 5A was followed except that 1-(4-fluorophenyl)-1-(4-butoxyphenyl)prop-2-yn-1-ol was used in place of 1-(4-butoxyphenyl)-1-(4-methoxyphenyl)prop-2-yn-1-ol. NMR analysis of the purple colored product indicated a structure that was consistent with 3-(4-butoxyphenyl)-3-(4-fluorophenyl)-10,12-dibromo-6-trifluoromethyl-13,13-dimethyl-indeno[2',3':3,4]naphtho[1,2-b]pyran.

Step 2

To a mixture of the product of Step 1 (2.00 g) and 4-(4,4,5,5-tetramethyl-1,3,2-dioxaborolan-2-yl)phenol (0.57 g) in 1:1 mixture of THF (25 mL) and water (25 mL) in a reaction flask was added potassium fluoride (1.5 g). The solution was degassed by bubbling nitrogen for 10 min. To the degassed solution, bis(triphenylphosphine) palladium(II) chloride (0.25 g) was added. The solution was heated to reflux for 8 h. The reaction mixture was cooled to room temperature and diluted with ethyl acetate. The mixture was then filtered through a bed of CELITE® filter aid and the filtrate was partitioned with ethyl acetate and water. The ethyl acetate extract was collected, dried with anhydrous sodium sulfate and concentrated to provide an oily residue. The residue was purified by column chromatography using 9:1 (v:v) hexane and ethyl acetate mixture as the eluant. Fractions that contained the desired product were grouped and concentrated in vacuo to provide an oily residue. The oil was dissolved in a minimum amount of dichloromethane and added drop-wise to a vigorously stirred solution of methanol. The resulting precipitate was collected by vacuum filtration and dried to provide a solid (1.00 g). NMR analysis of the solid indicated a structure that was consistent with 3-(fluorophenyl)-3-(4-butoxyphenyl)-10-(4-hydroxyphenyl)-6-trifluoromethyl-12-bromo-13,13-dimethyl-3,13-dihydro-indeno[2',3':3,4]naphtho[1,2-b]pyran.

Example 16

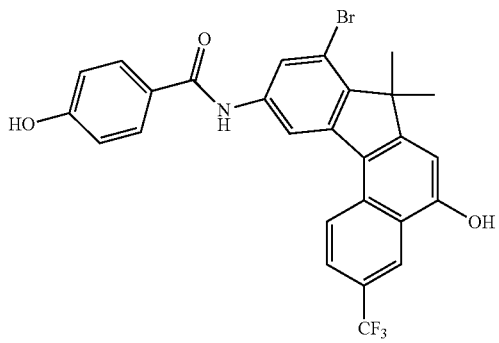 [SMILES: CC1(C)c2cc(O)c3cc(C(F)(F)F)ccc3c2-c2cc(NC(=O)c3ccc(O)cc3)cc(Br)c21]

To a three neck round bottom flask (100 mL) were added bis(dibenzylideneacetone)plalladium(0) (0.55 g), 2-di-tert-butylphosphino-3,4,5,6-tetramethyl-2',4',6'-triisopropyl-1,1'-biphenyl (1.14 g), crushed potassium phoshate (8.72 g), 8,10-dibromo-7,7-dimethyl-3-(trifluoromethyl)-7H-benzo[c]fluoren-5-yl acetate from Step 4 of Example 5 (5.00 g) and 4-hydroxybenzamide (2.15 g). The flask was evacuated and filled with nitrogen. Degassed tert-butanol (30 mL) was added and the mixture was heated to reflux for 6 h. The reaction mixture was cooled to room temperature and diluted with EtOAc. The solution was filtered through a bed of CELITE® filter aid and the filtrate was collected. The filtrate was concentrated and the residue was purified by column chromatography using 4:1 (v:v) ethyl acetate and hexanes mixture as the eluant. Fractions containing the desired material were grouped and concentrated to provide an oil. The oil was added to a minimum amount of ethyl acetate and hexanes was added, and the flask was scratched to provide crystals. The crystals were collected by vacuum filtration and dried to provide a white colored solid (4.27 g). NMR analysis of the white colored solid indicated a structure that was consistent with 8-bromo-7,7-dimethyl-3-trifluoromethyl-10-(4-hydroxybenzamido)-7H-benzo[c]fluoren-5-ol.

Example 16A

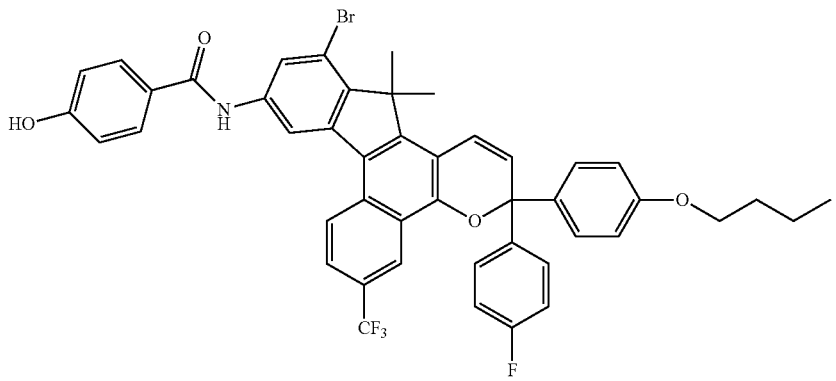 [SMILES: CCCCOc1ccc(C2(c3ccc(F)cc3)C=Cc3c4c(c5ccc(C(F)(F)F)cc5c3O2)-c2cc(NC(=O)c3ccc(O)cc3)cc(Br)c2C4(C)C)cc1]

The procedure from Example 5A was followed except that 1-(4-fluorophenyl)-1-(4-butoxyphenyl)prop-2-yn-1-ol was used in place of 1-(4-butoxyphenyl)-1-(4-methoxyphenyl)prop-2-yn-1-ol and the product from Example 16 was used in place of 8,10-dibromo-7,7-dimethyl-3-(trifluoromethyl)-7H-benzo[c]fluoren-5-ol. NMR analysis of the cream colored solid indicated a structure that was consistent with 3-(fluorophenyl)-3-(4-butoxyphenyl)-10-(4-hydroxybenzamido)-6-trifluoromethyl-12-bromo-13,13-dimethyl-3,13-dihydro-indeno[2',3':3,4]naphtho[1,2-b]pyran.

Example 17

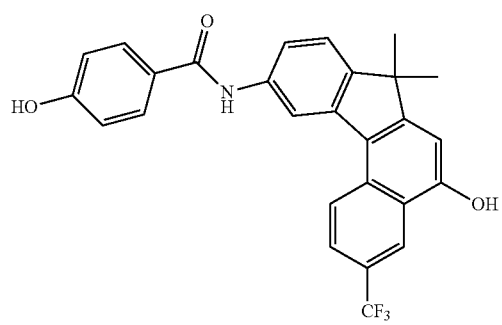 [SMILES: CC1(C)c2ccc(NC(=O)c3ccc(O)cc3)cc2-c2c1cc(O)c1cc(C(F)(F)F)ccc21]

8-Bromo-7,7-dimethyl-3-trifluoromethyl-10-(4-hydroxybenzamido)-7H-benzo[c]fluoren-5-ol (5.00 g) from Example 16, potassium carbonate (5.10 g), 2-butanol (50 mL) and methanol (50 mL) were added to a round bottom flask and degassed for 10 min. Tetrakistriphenylphosphine palladium (0) (0.55 g) was added and heated to reflux under nitrogen for 2 h. The reaction mixture was cooled to room temperature and filtered through a bed of CELITE® filter aid. The filtrate was concentrated and the residue was purified by column chromatography using 4:1 (v:v) ethyl acetate and hexanes mixture as the eluant. Fractions containing the desired material were grouped and concentrated to provide a foam (4.00 g). NMR analysis of the foam indicated a structure that was consistent with 4-hydroxy-N-(5-hydroxy-7,7-dimethyl-3-(trifluoromethyl)-7H-benzo[c]fluoren-10-yl)benzamide.

Example 17A

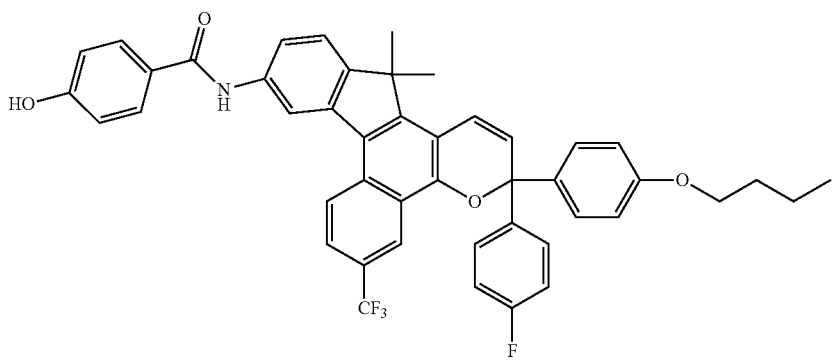 [SMILES: CCCCOc1ccc(C2(c3ccc(F)cc3)C=Cc3c4c(c5ccc(C(F)(F)F)cc5c3O2)-c2cc(NC(=O)c3ccc(O)cc3)ccc2C4(C)C)cc1]

The procedure from Example 5A was followed except that 1-(4-fluorophenyl)-1-(4-butoxyphenyl)prop-2-yn-1-ol was used instead of 1-(4-butoxyphenyl)-1-(4-methoxyphenyl)prop-2-yn-1-ol and the product from Example 17 was used in place of 8,10-dibromo-7,7-dimethyl-3-(trifluoromethyl)-7H-benzo[c]fluoren-5-ol. NMR analysis of the cream colored solid indicated a structure that was consistent with 3-(fluorophenyl)-3-(4-butoxyphenyl)-10-(4-hydroxybenzamido)-6-trifluoromethyl-13,13-dimethyl-3,13-dihydro-indeno[2',3':3,4]naphtho[1,2-b]pyran.

Example 18

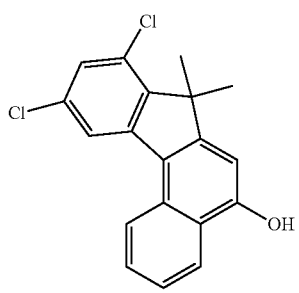 [SMILES: CC1(C)c2cc(O)c3ccccc3c2-c2cc(Cl)cc(Cl)c21]

Step 1

Magnesium (5.38 g) and THF (50 mL) was placed in a dry flask equipped with a dropping funnel which contained a mixture of 1-bromo-3,5-dichlorobenzene (50 g) and THF (300 mL). 30 mL of the solution in the dropping funnel was added to the flask. A few drops of dibromoethane were also added to the flask and a few minutes later, solvent in the reaction flask started to boil. The remainder of the solution in the dropping funnel was added drop wise. Ice water was used occasionally to help the reaction mixture to stay at around room temperature. After the addition, the mixture was stirred at room temperature for two hours. Benzonitrile (22.82 g) was added to the reaction mixture and the mixture was refluxed for 2 days. 3 N HCl (300 mL) was added and the mixture was stirred for 4 hours and then extracted using ethyl acetate. The organic layer was collected and then concentrated. The recovered oil (49 g) was used in the next step without further purification.

Step 2

The product from Step 1 (47 g), dimethyl succinate (36 g) and toluene (500 mL) were added to a reaction flask equipped with a mechanical stirrer, a solid addition funnel and a nitrogen blanket. The mixture was stirred at room temperature until the solids were dissolved. Solid potassium t-butoxide (23.1 g) was added through the solid addition funnel and the mixture was stirred at room temperature for 4 hours. The resulting reaction mixture was poured into 1 L of water and the aqueous layer, which contained the product, was collected. The toluene layer was extracted with 200 mL water. The combined water solution was washed with toluene. HCl (3 N) was added to the water solution to adjust the pH to 5. The resulting mixture was extracted with ethyl acetate, dried over magnesium sulfate, concentrated and dried in vacuum. Oil was obtained as product (65 g). It was used directly in the next step.

Step 3

A mixture of the product (65 g) from Step 2 and acetic anhydride (200 mL) was mixed and refluxed in a reaction flask equipped with a condenser. After one hour, the acetic anhydride was removed by vacuum evaporation and the obtained oil (67 g) was used directly in the next step.

Step 4

To a reaction flask containing the product of Step 3 (67 g) was added methanol (500 mL) of and HCl (12 N, 1 mL). The mixture was refluxed for two hours. Methanol was removed by vacuum evaporation. The recovered oil was dissolved in methylene chloride, washed with sodium bicarbonate saturated water, dried over magnesium sulfated, concentrated and dried in vacuum. Clear oil (48 g) was obtained. Ethyl acetate/hexane (1/9) ((v/v) was used to crystallize the product. White crystals (12 g) were obtained as the undesired regio-isomer. The mother liquor was concentrated. Oil (31 g) was obtained. NMR indicated that majority of the product in the oil (80%) had a structure consistent with methyl 1-(3,5-dichlorophenyl)-4-hydroxy-2-naphthoate.

Step 5

The product (31 g) from Step 4 was dissolved in anhydrous THF (500 ml) in an oven dried flask equipped with a dropping funnel and a magnetic stir bar. The mixture was stirred mixture at room temperature, and 1.6 M toluene/THF (1:1) solution of methyl magnesium bromide (160 ml) was added dropwise. After the addition, the mixture was stirred at room temperature for about 16 hours. The reaction mixture was then poured into 2 L of ice water. The pH value of the mixture was adjusted to ~2 using HCl (12 N). Ethyl acetate (500 mL) was added. The resulting organic layer was separated, dried over magnesium sulfate, concentrated and dried in vacuum. The recovered product (30 g of oil) was used directly in the next step.

Step 6

The product from Step 5 (30 g) and xylene (300 were added to a reaction flask equipped with a magnetic stir bar. p-Toluenesulfonic acid (1 g) was added and the resulting mixture was refluxed for eight hours. Xylene was removed by vacuum evaporation and the resulting oily product was dissolved in ethyl acetate, washed with water, dried over magnesium sulfate and concentrated. The crude product was obtained as oil (20 g). A small portion of the product (1.8 g) was purified using a CombiFlash Rf from Teledyne ISCO. After separation, two components were obtained. NMR analysis showed the major component had a structure consistent with: 8,10-dichloro-7,7-dimethyl-7H-benzo[c]fluoren-5-ol.

Example 18A

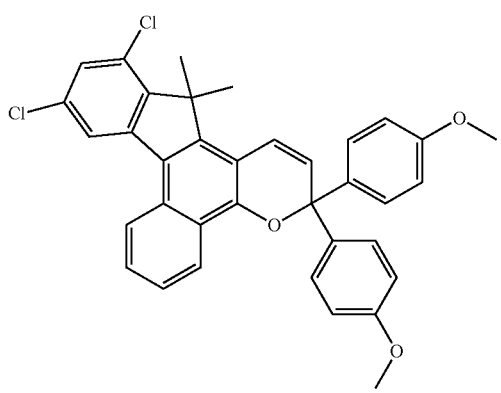 [SMILES: COc1ccc(C2(c3ccc(OC)cc3)C=Cc3c4c(c5ccccc5c3O2)-c2cc(Cl)cc(Cl)c2C4(C)C)cc1]

The crude product from Step 6 of Example 18 (18 g) was placed in a reaction flask. To the flask was added of 1,1-bis(4-methoxyphenyl)prop-2-yn-1-ol (20 g), a few crystals of p-toluenesulfonic acid and methylene chloride (300 ml). The mixture was stirred at room temperature for one hour. The product was purified using a CombiFlash® Rf from Teledyne ISCO followed by a recrystallization from ethyl ether. A grey solid (10 g) was obtained as the product. NMR analysis indicated that the product had a structure consistent with 3,3-bis(4-methoxyphenyl)-10,12-dichloro-13,13-trimethyl-3,13-dihydro-indeno[2',3':3,4]naphtho[1,2-b]pyran.

Example 19

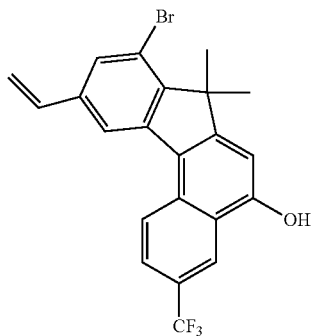 [SMILES: C=Cc1cc(Br)c2c(c1)-c1c(cc(O)c3cc(C(F)(F)F)ccc13)C2(C)C]

Triphenylphosphine (2.23 g) and palladium acetate (0.64 g) were added to a degassed mixture of toluene (30 mL) and ethanol (30 mL). 8,10-Dibromo-7,7-dimethyl-3-(trifluoromethyl)-7H-benzo[c]fluoren-5-yl acetate (15.00 g) from Step 4 of Example 5 and vinylboronic pinacol ester (8.75 g) were added and the solution was degassed by bubbling nitrogen for 10 min. Potassium carbonate (11.75 g) was added and the mixture was heated to reflux for 18 h. The reaction mixture was cooled to room temperature and carefully poured into 10% aqueous HCl. The mixture was stirred for 10 min and the aqueous was partitioned with EtOAc. The EtOAc extract was washed with saturated sodium bisulfite. The EtOAc extract was then filtered through Celite. The filtrate was concentrated under vacuum to provide a residue. The residue was purified by a plug of silica and eluting with 9:1 hexane:EtOAc. Fractions containing the desired material were grouped and concentrated to provide a white solid (8 g). NMR analysis of the white solid indicated a structure that was consistent with 8-bromo-7,7-dimethyl-3-trifluoromethyl-10-vinyl-7H-benzo[c]fluoren-5-ol.

Example 19A

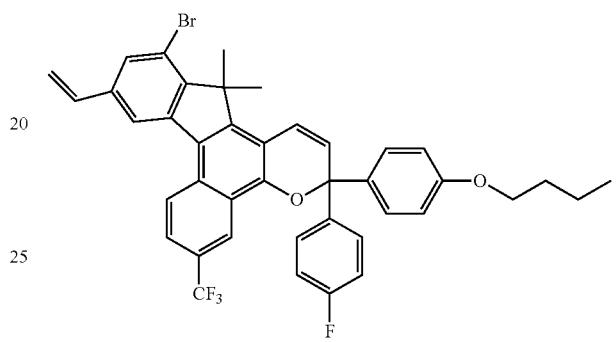

The procedure from Example 5A was followed except that 1-(4-fluorophenyl)-1-(4-butoxyphenyl)prop-2-yn-1-ol was used in place of 1-(4-butoxyphenyl)-1-(4-methoxyphenyl)prop-2-yn-1-ol and the product from Example 19 was used in place of 8,10-dibromo-7,7-dimethyl-3-(trifluoromethyl)-7H-benzo[c]fluoren-5-ol. NMR analysis of the cream colored solid indicated a structure that was consistent with 3-(4-fluorophenyl)-3-(4-butoxyphenyl)-10-vinyl-6-trifluoromethyl-12-bromo-13,13-dimethyl-3,13-dihydro-indeno[2',3':3,4]naphtho[1,2-b]pyran.

Example 20

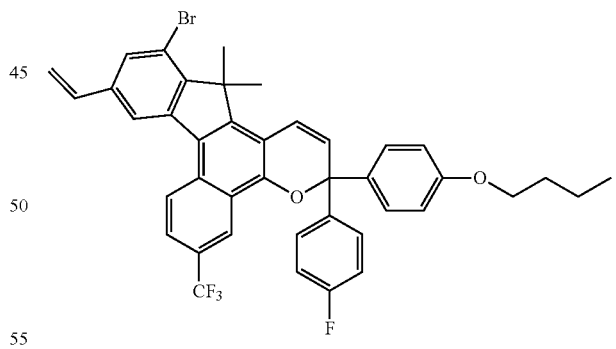

The product from Step 1 of Example 19, 8-bromo-7,7-dimethyl-3-(trifluoromethyl)-10-vinyl-7H-benzo[c]fluorenol (8.44 g), potassium carbonate (10.75 g), 2-butanol (20 mL) and methanol (20 mL) were added to a round bottom flask (100 mL) and degassed for 10 min. Bis(triphenylphosphine)palladium(II)chloride (0.7 g) was added and heated to reflux for 18 h. The reaction mixture was cooled to room temperature and carefully poured into 10% HCl. The mixture was diluted with ethyl acetate and partitioned. The ethyl acetate extract was washed with sodium bisulfite and dried with sodium sulfate. The ethyl acetate solution was then filtered through a bed of Celite and the filtrate was concentrated. The residue was purified by column chromatography using 9:1 hexane ethyl acetate mixtures as the eluent. Fractions containing the desired material were grouped and concentrated to provide a yellow colored oil (6.91 g). NMR analysis of the yellow colored oil confirmed that the structure was consistent with 7,7-dimethyl-3-trifluoromethyl-10-vinyl-7H-benzo[c]fluoren-5-ol.

Example 20A

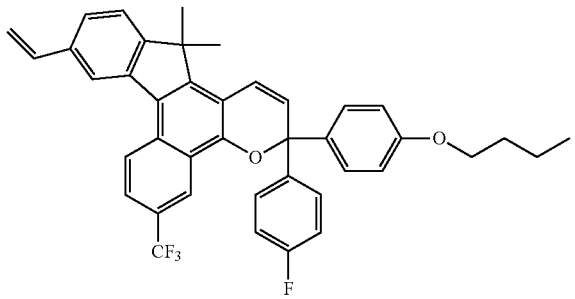 [SMILES: C=Cc1ccc2c(c1)-c1c(c3c(c4cc(C(F)(F)F)ccc14)OC(c1ccc(F)cc1)(c1ccc(OCCCC)cc1)C=C3)C2(C)C]

The procedure from Example 5A was followed except that 1-(4-fluorophenyl)-1-(4-butoxyphenyl)prop-2-yn-1-ol was used in place of 1-(4-butoxyphenyl)-1-(4-methoxyphenyl)prop-2-yn-1-ol and the product from Example 20 was used in place of 8,10-dibromo-7,7-dimethyl-3-(trifluoromethyl)-7H-benzo[c]fluoren-5-ol. NMR analysis of the foam indicated a structure that was consistent with 3-(4-fluorophenyl)-3-(4-butoxyphenyl)-10-vinyl-6-trifluoromethyl-13,13-dimethyl-3,13-dihydro-indeno[2',3':3,4]naphtho[1,2-b]pyran.

Example 21

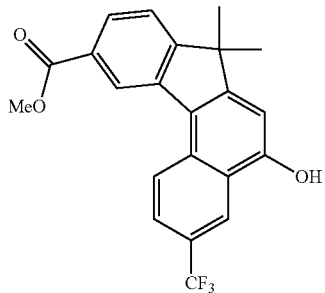 [SMILES: COC(=O)c1ccc2c(c1)-c1c(cc(O)c3cc(C(F)(F)F)ccc13)C2(C)C]

Step 1

The product from Step 1 of Example 20, 7,7-dimethyl-3-(trifluoronnethyl)-10-vinyl-7H-benzo[c]fluorenol-5-ol (5.87 g) was dissolved in dichloromethane (20 mL). Triethylamine (7 mL) was added and stirred for 5 mins. Triisopropylsilyl trifloromethanesulfonate (11.00 g) was added drop-wise. The reaction mixture was stirred at room temperature for 30 min. Saturated sodium bicarbonate (300 mL) was poured into the reaction mixture and stirred for 5 min. The aqueous was diluted with dichloromethane and partitioned. The organic layer was collected, dried with anhydrous sodium sulfate and filtered. The filtrate was concentrated to provide a residue. The residue was purified by column chromatography using activated alumina basic and 9:1 hexane ethyl acetate mixtures as the eluent. Fractions containing the desired material were grouped and concentrated to provide a colorless oil (6.91 g).

Step 2

The product from Step 1 of Example 21 (6.91 g) was dissolved in t-butanol (42 mL), water (94 mL) and cooled to 0° C. A solution of KMNO4 (6.4 g) in water (60 mL) was added slowly to the solution of the starting material. The pH of the solution was adjusted to 8-10 by the addition of aqueous sodium carbonate. The ice bath was removed and the reaction mixture was warmed to room temperature and stirred for 20 h. The mixture was filtered through a bed of Celite and the filtrate was carefully acidified to pH 4 by the addition of 10% aqueous HCl. The aqueous solution was partitioned with ethyl acetate and the organic layer was collected, dried with anhydrous sodium sulfate and concentrated in vacuo to afford an oily residue. The oily residue was purified through a silica plug and eluted with 4:1 hexane ethyl acetate mixtures. Fractions containing the desired material were grouped and concentrated in vacuo to provide a white solid (3.36 g). NMR analysis of the white solid indicated a structure that was consistent with 7,7-dimethyl-3-(trifluoromethyl)-5-((triisopropylsilypoxy)-7H-benzo[c]fluorene-10-carboxylic acid.

Step 3

The product from Step 2 of Example 21 (1.80 g) was dissolved in methylene chloride (10 mL). Methanol (0.2 mL) was added followed by dimethylamino pyridine (0.06 g) and N,N'-dicylcohexylcabodiimide (0.85 g). The mixture was stirred for 1 h at room temperature. The mixture was diluted with methylene chloride and filtered. The filtrate was collected and concentrated in vacuo. The crude material was dissolved in THF (12 mL) and water (12 mL). Potassium fluoride (0.6 g) was added and the mixture stirred at room temperature for 18 h. Ethyl acetate (100 mL) was added and was partitioned with water. The ethyl acetate extract was collected, dried with anhydrous sodium sulfate and concentrated in vacuo to provide a residue. The residue was dissolved in methylene chloride and hexane was added until a precipitate formed. The precipitate (1.13 g) was collected by vacuum filtration and washed with cold hexane. NMR analysis of the precipitate indicated a structure that was consistent with 7,7-dimethyl-3-trifluoromethyl-10-methoxycarbonyl-7H-benzo[c]fluoren-5-ol.

Example 21A

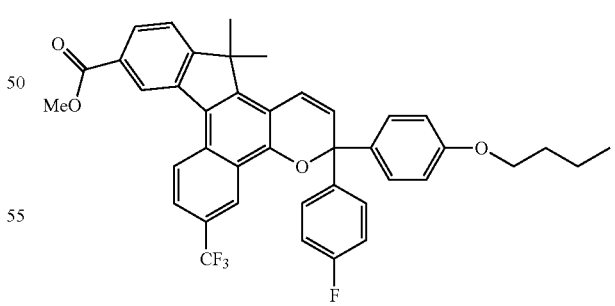

The procedure from Example 5A was followed except that 1-(4-fluorophenyl)-1-(4-butoxyphenyl)prop-2-yn-1-ol was used in place of 1-(4-butoxyphenyl)-1-(4-methoxyphenyl)prop-2-yn-1-ol and the product from Example 21 was used in place of 8,10-dibromo-7,7-dimethyl-3-(trifluoronnethyl)-7H-benzo[c]fluoren-5-ol. NMR analysis of the cream colored solid indicated a structure that was consistent with 3-(4-fluorophenyl)-3-(4-butoxyphenyl)-10-methoxycarbonyl-6-trifluoromethyl-13,13-dimethyl-3,13-dihydro-indeno[2',3':3,4]naphtho[1,2-b]pyran.

Example 22A

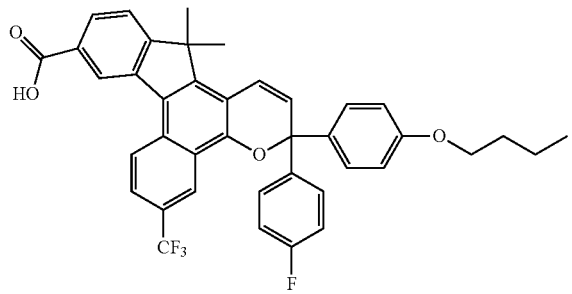 [SMILES: CCCCOc1ccc(C2(c3ccc(F)cc3)C=Cc3c4c(c5ccc(C(F)(F)F)cc5c3O2)-c2cc(C(=O)O)ccc2C4(C)C)cc1]

The product from Step 1 of Example 21A (0.63 g) was dissolved in tetrahydrofuran (10 mL), methanol (5 mL). 50% wt aqueous sodium hydroxide (3 mL) was added and the mixture was stirred at room temperature for 30 min. The mixture was poured in 10% aqueous HCl and stirred for 5 min. The aqueous was partitioned with ethyl acetate. The ethyl acetate layer was collected, dried with anhydrous sodium sulfate and concentrated to provide a residue. The residue was purified by column chromatography using 4:1 hexanes ethyl acetate mixtures. Fractions containing the desired material were grouped and concentrated to provide a purple colored foam (0.56 g). NMR analysis of the purple colored foam indicated a structure that was consistent with 3-(4-fluorophenyl)-3-(4-butoxyphenyl)-10-(carboxylic acid)-6-trifluoromethyl-13,13-dimethyl-3,13-dihydro-indeno[2',3':3,4]naphtho[1,2-b]pyran.

Example 23

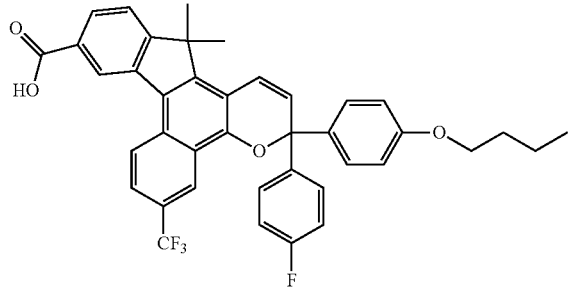 [SMILES: CCCCOc1ccc(C2(c3ccc(F)cc3)C=Cc3c4c(c5ccc(C(F)(F)F)cc5c3O2)-c2cc(C(=O)O)ccc2C4(C)C)cc1]

The product from Step 2 of Example 21 (0.51 g) and 4'-(trans-4-pentylcyclohexyl)-[1,1'-biphenyl]-4-amine (0.31 g) were dissolved in DCM (10 mL). DMAP (0.10 g) and DBSA (0.05 g) was added followed by DCC (0.25 g). The reaction mixture was stirred at room temperature for 2 h. The reaction mixture was filtered through a silica plug and the filtrate was collected and concentrated. The residue was dissolved in THF (10 mL) and a solution of potassium fluoride (0.6 g) in water (5 mL) was added and stirred at room temperature for 18 h. The reaction mixture was diluted with EtOAc and partitioned. The EtOAc layer was collected and concentrated to provide a residue. The residue was purified by column chromatography using 4:1 hexanes ethyl acetate mixtures. Fractions containing the desired material were grouped and concentrated to provide a white solid (0.47 g). NMR analysis of the white solid indicated a structure that was consistent with 7,7-dimethyl-3-trifluoromethyl-10-[(4'-(trans-4-pentylcyclohexyl)-[1,1'-biphenyl]-4-yl)carbamoyl]-7H-benzo[c]fluoren-5-ol.

Example 24

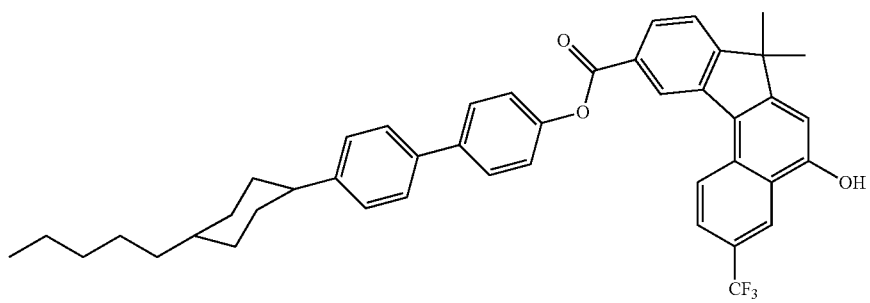 [SMILES: CCCCCC1CCC(c2ccc(-c3ccc(OC(=O)c4ccc5c(c4)-c4c(cc(O)c6cc(C(F)(F)F)ccc46)C5(C)C)cc3)cc2)CC1]

The procedure from Example 23 was followed except that 4'-(trans-4-pentylcyclohexyl)-[1,1'-biphenyl]-4-ol was used in place of 4'-(trans-4-pentylcyclohexyl)-[1,1'-biphenyl]-4-amine. NMR analysis of the white solid indicated a structure that was consistent with 7,7-dimethyl-3-trifluoromethyl-10-[((4'-(trans-4-pentylcyclohexyl)-[1,1'-biphenyl]-4-yl)oxy)carbonyl]-7H-benzo[c]fluoren-5-ol.

Example 25

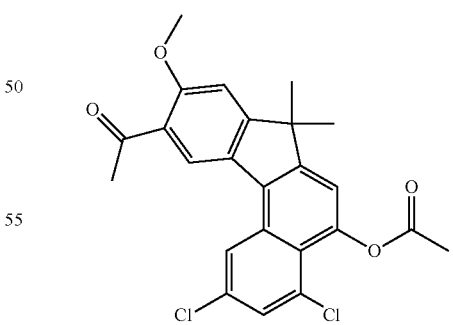

Procedures from Steps 1 to 4 of Example 5 were followed except that in Step 1, 3,5-dichlorobromobenzene and 4-methoxybenzoyl chloride was used in place of tribromobenzene and 4-trifluoromethylbenzoyl chloride. Compound 2,4-dichloro-9-methoxy-7,7-dimethyl-7H-benzo[c]fluoren-5-yl acetate was obtained as the undesired major product. The desired minor product was also collected as off-white powder.

NMR indicated that the desired product had a structure consistent with 10-acetyl-2,4-dichloro-9-methoxy-7,7-dimethyl-7H-benzo[c]fluoren-5-yl acetate. The formation of more of the desired minor product could be achieved by extending the reaction time in Step 4.

Example 26

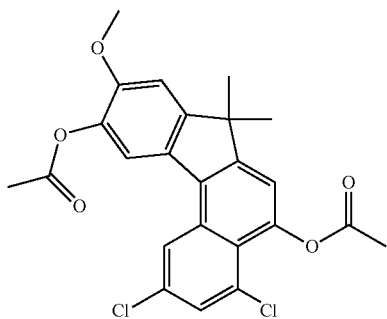 [SMILES: COc1cc2c(cc1OC(C)=O)-c1c(cc(OC(C)=O)c3c(Cl)cc(Cl)cc13)C2(C)C]

A mixture of 10-acetyl-2,4-dichloro-9-methoxy-7,7-dimethyl-7H-benzo[c]fluoren-5-yl acetate from Example 25 (3.5 g), 3-Chloroperoxybenzoic acid (4 g) and dichloromethane were placed in a reaction flask and refluxed for 4 hours. The reaction mixture was stirred at room temperature for 17 hours. All solvent was removed. Methanol (100 ml) was added to the obtained solid and the mixture was stirred at room temperature for 10 minutes. Solid was collected by vacuum filtration and further purified by recrystallization from mixture solvent dichloromethane and methanol. White crystals (3.4 g) were obtained as the product. NMR indicated that the product had a structure consistent with 2,4-dichloro-9-methoxy-7,7-dimethyl-7H-benzo[c]fluorene-5,10-diyl diacetate.

Example 27

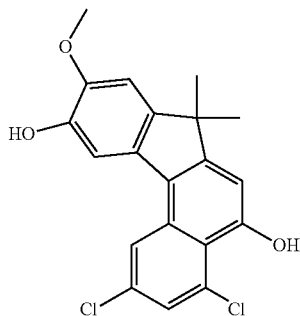 [SMILES: COc1cc2c(cc1O)-c1c(cc(O)c3c(Cl)cc(Cl)cc13)C2(C)C]

To a stirred mixture of 2,4-dichloro-9-methoxy-7,7-dimethyl-7H-benzo[c]fluorene-5,10-diyl diacetate (3.4 g) from Example 24 and THF (100 ml), 50 wt % water solution of sodium hydroxide (10 ml) was added. The mixture was refluxed for 10 minutes. Ethyl acetate (100 ml) was then added and pH of the mixture was adjusted to 2 using 3 N HCl water solution. The mixture was extracted with water, dried over magnesium sulfate and concentrated. Yellow oil (1.9 g) was obtained as the product. NMR indicated that the product had a structure consistent with 2,4-dichloro-9-methoxy-7,7-dimethyl-7H-benzo[c]fluorene-5,10-diol.

Example 27A

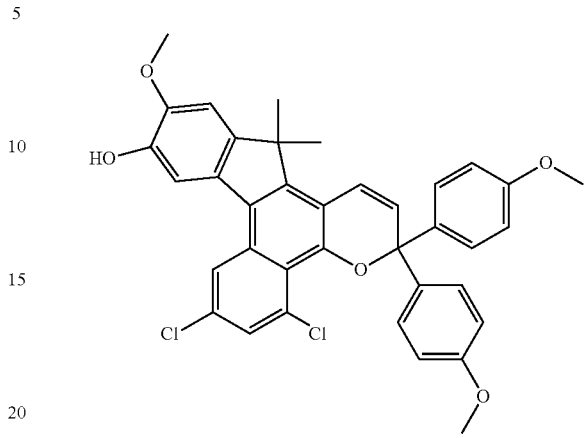

A mixture of 2,4-dichloro-9-methoxy-7,7-dimethyl-7H-benzo[c]fluorene-5,10-diol from Example 27 (1.9 g), 1,1-bis(4-methoxyphenyl)prop-2-yn-1-ol (1.3 g), p-toluenesulfonic acid (0.1 g) and methylene chloride (100 ml) was refluxed for an hour. All solvent was removed. The black crude product was purified using a CombiFlash followed by recrystallization from methylene chloride/methanol. Yellow crystals (0.9 g) were obtained as the product. NMR indicated the minor product had a structure consistent with 3,3-bis(4-methoxyphenyl)-5,7-dichloro-10-hydroxy-11-methoxy-13,13-dimethyl-3,13-dihydro-indeno[2',3':3,4]naphtho[1,2-b]pyran.

Example 28A

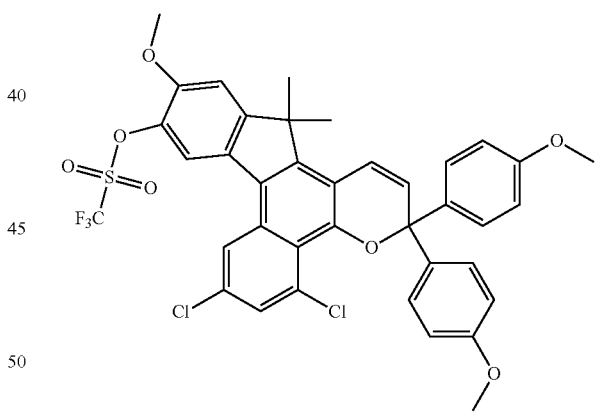

To a stirred mixture of 3,3-bis(4-methoxyphenyl)-5,7-dichloro-10-hydroxy-11-methoxy-13,13-dimethyl-3,13-dihydro-indeno[2',3':3,4]naphtho[1,2-b]pyran from Example 27A (0.3 g), methylene chloride (50 ml) and triethylamine (2 ml), methylene chloride (10 ml) solution of trifluoromethanesulfonic anhydride (1 g) was dropped in slowly in 5 minutes. After the addition, the mixture was stirred at room temperature for 5 minutes and then water was added (50 ml). The organic layer was collected, washed with HCl/water (1 mol/L, 50 ml) washed with saturated sodium bicarbonate water solution (50 ml), dried over magnesium sulfate and concentrated. The crude product was plug-columned over silica gel using toluene as solvent. After evaporation of solvent, product was purified by recrystallization from methylene chloride/ methanol. Yellow crystals (0.2 g) were obtained as the product. NMR indicated the minor product had a structure consistent with 3,3-bis(4-methoxyphenyl)-5,7-dichloro-10-trifluoromethanesulfonyl-11-methoxy-13,13-dimethyl-3, 13-dihydro-indeno[2',3':3,4]naphtho[1,2-b]pyran.

Part 2

Photochromic Property Testing

Part 2A—Test Square Preparation

Testing was done with the compounds described in Examples 2A-5A, 9A, 10A, 13A, 18A-22A, 27A and 28A in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly (ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on the optical bench, the photochromic test squares from Part 2A were conditioned by exposure to 365 nm ultraviolet light for about 30 minutes at a distance of about 14 cm from the source to cause the photochromic material to transform from the ground state-form to an activated-state form, and then placed in a 75° C. oven for about 20 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench.

The optical bench was fitted with an Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 73.4° F.±2° (23° C.±1.1°) for photochromic response testing. A Newport Model 689456 Digital Exposure Timer was used to control the intensity of the xenon arc lamp during activation of the sample.

A custom broadband tungsten lamp based light source for monitoring response measurements was positioned in a perpendicular manner to a surface of the cell assembly. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer.

Adjusting the output of the filtered xenon arc lamp was accomplished by increasing or decreasing the current to the lamp through the controller and/or by adding or removing neutral density filters in the light path. The test samples were exposed to the activation light at 31° normal to its surface while being perpendicular to the monitoring light.

Samples were activated in the 73.4° F. (23° C.) controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half life is the time interval in seconds for the ΔOD of the activated form of the photochromic compound in the test squares to reach one half the ΔOD measured after thirty minutes, or after saturation or near-saturation was achieved, at room temperature after removal of the source of activating light, e.g., by closing the shutter. Results are listed in Table I.

TABLE 1

Photochromic Performance Test Results

| Example # | $\lambda_{max\text{-}vis}$ (nm) | Sensitivity (ΔOD/Min) | ΔOD at saturation | T½ (sec) |
|---|---|---|---|---|
| 2A | 572 | 0.44 | 0.27 | 35 |
| 3A | 564 | 0.46 | 0.34 | 44 |
| 4A | 551 | 0.65 | 0.44 | 35 |
| 5A | 565 | 0.23 | 0.09 | 14 |
| 9A | 603 | 0.33 | 0.18 | 28 |
| 10A | 562 | 0.28 | 0.10 | 14 |
| 13A | 572 | 0.26 | 0.26 | 93 |
| 18A | 550 | 0.49 | 0.36 | 39 |
| 19A | 555 | 0.17 | 0.20 | 176 |
| 20A | 563 | 0.22 | 0.36 | 224 |
| 21A | 556 | 0.40 | 0.29 | 35 |
| 22A | 557 | 0.43 | 0.30 | 35 |
| 27A | 588 | 1.07 | 0.88 | 79 |
| 28A | 572 | 0.91 | 0.53 | 34 |

The present invention has been described with reference to specific details of particular embodiments thereof. It is not intended that such details be regarded as limitations upon the scope of the invention except insofar as to the extent that they are included in the accompanying claims.

We claim:
1. An indeno-fused ring compound represented by the following Formula I,

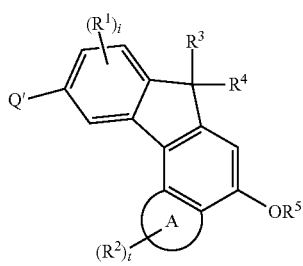

I wherein,
(A) Ring-A is selected from unsubstituted aryl, substituted aryl, unsubstituted fused ring aryl, or substituted fused ring aryl,
(B) Q' is selected from halogen, —OH, —N₃, —NRᵃRᵃ, —N(Rᵃ)C(O)Q″, —CN, —C(O)ORᵃ, —C(O)Rᵃ, —C≡C—Rᵃ, —C(Rᵃ)=C(Rᵃ)(Rᵃ), —OC(O)Rᵃ, —OC(O)ORᵃ, —SRᵃ, —OS(O₂)Rᵇ, —C(O)NRᵃRᵃ and a lengthening agent L, wherein each Rᵃ is independently selected from hydrogen, hydrocarbyl and substituted hydrocarbyl each optionally and independently interrupted with at least one of —O—, —S—, —C(O)—, —C(O)O—, —S(O)—, —S(O₂)—, —N=N—, —N(R₁₁')— where R₁₁' is selected from hydrogen, hydrocarbyl or substituted hydrocarbyl, —Si(OR₁₄)ᵤ(R₁₄)ᵥ—, where u and v are each independently selected from 0 to 2, provided that the sum of u and v is 2, and each R₁₄ is independently selected from hydrogen, hydrocarbyl and substituted hydrocarbyl, and combinations of two or more thereof, or two Rᵃ groups come together with —N and optionally an additional hetero atom selected from N and O to form a heterocycloalkyl, and Rᵇ is selected from perhalohydrocarbyl, and Q″ is selected from halo, —ORᵃ, —NRᵃRᵃ, —C(O)ORᵃ, —SRᵃ, and hydrocarbyl or substituted hydrocarbyl, wherein said substituents are selected from —OH, —NRᵃRᵃ, —C(O)ORᵃ, —SRᵃ, wherein said lengthening agent L is represented by the following formula,

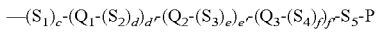

wherein,
(i) each Q₁, Q₂, and Q₃ is independently chosen for each occurrence from, a divalent group chosen from, an unsubstituted or a substituted aromatic group, an unsubstituted or a substituted alicyclic group, an unsubstituted or a substituted heterocyclic group, and mixtures thereof, wherein substituents are chosen from, a group represented by P, liquid crystal mesogens, halogen, poly(C₁-C₁₈ alkoxy), C₁-C₁₈ alkoxycarbonyl, C₁-C₁₈ alkylcarbonyl, C₁-C₁₈ alkoxycarbonyloxy, aryloxycarbonyloxy, perfluoro(C₁-C₁₈)alkoxy, perfluoro(C₁-C₁₈)alkoxycarbonyl, perfluoro(C₁-C₁₈)alkylcarbonyl, perfluoro(C₁-C₁₈)alkylamino, di-(perfluoro(C₁-C₁₈)alkyl)amino, perfluoro(C₁-C₁₈)alkylthio, C₁-C₁₈ alkylthio, C₁-C₁₈ acetyl, C₃-C₁₀ cycloalkyl, C₃-C₁₀ cycloalkoxy, a straight-chain or branched C₁-C₁₈ alkyl group that is mono-substituted with cyano, halo, or C₁-C₁₈ alkoxy, or poly-substituted with halo, and a group comprising one of the following formulae: -M(T)₍ₜ₋₁₎ and -M(OT)₍ₜ₋₁₎, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M,
(ii) c, d, e, and f are each independently chosen from an integer ranging from 0 to 20, inclusive; and each S₁, S₂, S₃, S₄, and S₅ is independently chosen for each occurrence from a spacer unit chosen from:
(1) optionally substituted alkylene, optionally substituted haloalkylene, —Si(Z')₂(CH₂)ɡ—, and

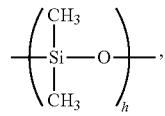

wherein each Z' is independently selected from hydrogen, C₁-C₁₈ alkyl, C₃-C₁₀ cycloalkyl, and aryl; g for each occurrence is independently chosen from an integer from 1 to 20; h for each occurrence is independently chosen from an integer from 1 to 16; and said substituents for the alkylene and haloalkylene are independently selected from C₁-C₁₈ alkyl, C₃-C₁₀ cycloalkyl and aryl;
(2) —N(Z)—, —C(Z)=C(Z)—, —C(Z)=N—, —C(Z')₂—C(Z')₂—, or a single bond, wherein Z is independently chosen for each occurrence from hydrogen, C₁-C₈ alkyl, C₃-C₁₀ cycloalkyl and aryl, and Z' is independently chosen for each occurrence from C₁-C₁₈ alkyl, C₃-C₁₀ cycloalkyl and aryl; and
(3) —O—, —C(O)—, —C≡C—, —N=N—, —S—, —S(O)—, —S(O)(O)—, —(O)S(O)—, —(O)S(O)O—, —O(O)S(O)O—, or straight-chain or branched C₁-C₂₄ alkylene residue, said C₁-C₂₄ alkylene residue being unsubstituted, mono-substituted by cyano or halo, or poly-substituted by halo,
provided that when two spacer units comprising heteroatoms are linked together the spacer units are linked so that heteroatoms are not directly linked to each other, and provided that when $S_1$ and $S_5$ are linked to Formula I and P, respectively, they are linked so that two heteroatoms are not directly linked to each other,
  (iii) P is chosen from: hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy) ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylenyl, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato ($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor; and
  (iv) d', e' and f' are each independently chosen from 0, 1, 2, 3, and 4, provided that a sum of d'+e'+f' is at least 1;
(C) i is selected from 0 to 3, t is selected from 0 to a total number of positions to which $R^2$ can be bonded, and $R^1$ for each i, and $R^2$ for each t, are each independently selected from, hydrocarbyl and substituted hydrocarbyl each optionally and independently interrupted with at least one of —O—, —S—, —C(O)—, —C(O)O—, —S(O)—, —S(O$_2$)—, —N=N—, —N($R_{11}$')— where $R_{11}$' is selected from hydrogen, hydrocarbyl or substituted hydrocarbyl, —Si(OR$_{14}$)$_u$(R$_{14}$)$_v$—, where u and v are each independently selected from 0 to 2, provided that the sum of u and v is 2, and each $R_{14}$ is independently selected from hydrogen, hydrocarbyl and substituted hydrocarbyl, and combinations of two or more thereof; halogen; cyano; and —N($R_{11}$')$R_{12}$', wherein $R_{11}$' and $R_{12}$' are each independently selected from hydrogen, hydrocarbyl or substituted hydrocarbyl, or $R_{11}$' and $R_{12}$' together form a ring structure optionally including at least one heteroatom,
(D) $R^3$ and $R^4$ are each independently selected from, hydrogen; hydrocarbyl and substituted hydrocarbyl each optionally and independently interrupted with at least one of —O—, —S—, —C(O)—, —C(O)O—, —S(O)—, —S(O$_2$)—, —N=N—, —N($R_{11}$')— where $R_{11}$' is selected from hydrogen, hydrocarbyl or substituted hydrocarbyl, —Si(OR$_4$)$_u$(R$_{14}$)$_v$—, where u and v are each independently selected from 0 to 2, provided that the sum of u and v is 2, and each $R_{14}$ is independently selected from hydrogen, hydrocarbyl and substituted hydrocarbyl, and combinations of two or more thereof; or $R^3$ and $R^4$ together form a ring structure optionally including at least one heteroatom, and
(E) $R^5$ is selected from hydrogen, —C(O)—$R^{13}$ or —S(O$_2$) $R^{13}$ wherein $R^{13}$ is hydrocarbyl, or halohydrocarbyl.

2. The indeno-fused ring compound of claim 1, wherein,
(A) Ring-A is unsubstituted aryl or substituted aryl;
(B) Q' is selected from bromo, fluoro, chloro, —N$_3$, —NR$^a$R$^a$, —N(R$^a$)C(O)Q", —C(O)OR$^a$, —C(O)R$^a$, —C≡C—R$^a$, —C(R$^a$)=C(R$^a$)(R$^a$), —OC(O)R$^a$, —OC(O)OR$^a$, —SR$^a$, —OS(O$_2$)R$^b$, —C(O)NR$^a$R$^a$, and said lengthening agent L, wherein each R' is independently selected from hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl, or two R$^a$ groups come together with —N and an additional hetero atom selected from N and O to form a heterocycloalkyl and R$^b$ is selected from a perfluorinated alkyl group having from 1 to 18 carbon atoms, and Q" is selected from —OR$^a$, —NR$^a$R$^a$, —C(O)OR$^a$, —SR$^a$, and hydrocarbyl or substituted hydrocarbyl, wherein said substituents are selected from —OH, —NR$^a$R$^a$, —C(O)OR$^a$, —SR$^a$, and for lengthening agent L, d', e' and f' are each independently chosen from 0, 1, 2, 3, and 4, provided that a sum of d'+e'+f' is at least 2;
(C) $R^1$ for each i, and $R^2$ for each t, are each independently selected from,
  (a) —C(O)X$_{24}$, wherein X$_{24}$ is chosen from said lengthening agent L, hydroxy, $C_1$-$C_{18}$ alkyl, $C_1$-$C_{18}$ alkoxy, phenyl that is unsubstituted or mono-substituted with $C_1$-$C_{18}$ alkyl or $C_1$-$C_{18}$ alkoxy, amino that is unsubstituted, mono- or di-substituted with at least one of $C_1$-$C_{18}$ alkyl, phenyl, benzyl, and naphthyl,
  (b) —OX$_7$ and —N(X$_7$)$_2$; wherein X$_7$ is chosen from:
    (i) hydrogen, a lengthening agent L, $C_1$-$C_{18}$ alkyl, $C_1$-$C_{18}$ acyl, phenyl($C_1$-$C_{18}$)alkyl, mono($C_1$-$C_{18}$) alkyl substituted phenyl($C_1$-$C_{18}$)alkyl, mono($C_1$-$C_{18}$)alkoxy substituted phenyl($C_1$-$C_{18}$)alkyl; $C_1$-$C_{18}$ alkoxy($C_1$-$C_{18}$)alkyl; $C_3$-$C_{10}$ cycloalkyl; mono($C_1$-$C_{18}$)alkyl substituted $C_3$-$C_{10}$ cycloalkyl, $C_1$-$C_{18}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{18}$ alkyl, and $C_1$-$C_{18}$ alkoxy,
    (ii) —CH(X$_8$)X$_9$, wherein X$_8$ is chosen from hydrogen, a lengthening agent L, or $C_1$-$C_{18}$ alkyl, and X$_9$ is chosen from a lengthening agent L, —CN, —CF$_3$, or —COOX$_{10}$, wherein X$_{10}$ is chosen from hydrogen, a lengthening agent L, or $C_1$-$C_{18}$ alkyl,
    (iii) —C(O)X$_6$, wherein X$_6$ is chosen from at least one of, hydrogen, a lengthening agent L, $C_1$-$C_{18}$ alkoxy, phenoxy that is unsubstituted, mono- or di-substituted with $C_1$-$C_{18}$ alkyl or $C_1$-$C_{18}$ alkoxy, an aryl group that is unsubstituted, mono- or di-substituted with $C_1$-$C_{18}$ alkyl or $C_1$-$C_{18}$ alkoxy, an amino group that is unsubstituted, mono- or di-substituted with $C_1$-$C_{18}$ alkyl, and a phenylamino group that is unsubstituted, mono- or di-substituted with $C_1$-$C_{18}$ alkyl or $C_1$-$C_{18}$ alkoxy, or (iv) tri($C_1$-$C_{18}$)alkylsilyl, tri($C_1$-$C_{18}$)alkylsilyloxy, tri($C_1$-$C_{18}$)alkoxysilyl, tri($C_1$-$C_{18}$)alkoxysilyloxy, di($C_1$-$C_{18}$)alkyl($C_1$-$C_{18}$ alkoxy)silyl, di($C_1$-$C_{18}$) alkyl($C_1$-$C_{18}$ alkoxy)silyloxy, di($C_1$-$C_{18}$)alkoxy ($C_1$-$C_{18}$ alkyl)silyl or di($C_1$-$C_{18}$)alkoxy($C_1$-$C_{18}$ alkyl)silyloxy;

(c) —$SX_{11}$, wherein $X_{11}$ is chosen from hydrogen, a lengthening agent L, $C_1$-$C_{18}$ alkyl, $C_1$-$C_{18}$ haloalkyl, an aryl group that is unsubstituted, or mono- or di-substituted with $C_1$-$C_{18}$ alkyl, $C_1$-$C_{18}$ alkoxy, or halogen;

(d) a nitrogen containing ring represented by Formula i:

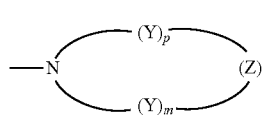

i wherein, each —Y— is independently chosen for each occurrence from —$CH_2$—, —$CH(R_{13}')$—, —$C(R_{13}')_2$—, —CH(aryl)-, —$C(aryl)_2$-, and —$C(R_{13}')$(aryl)-, and Z is —Y—, —O—, —S—, —S(O)—, —$SO_2$—, —NH—, —$N(R_{13}')$—, or —N(aryl)-, wherein each $R_{13}'$ is independently a lengthening group L, or $C_1$-$C_{20}$ alkyl, each aryl is independently phenyl or naphthyl, m is an integer 1, 2 or 3, and p is an integer 0, 1, 2, or 3, provided that when p is 0, Z is —Y—;

(e) a group represented by Formula ii or iii,

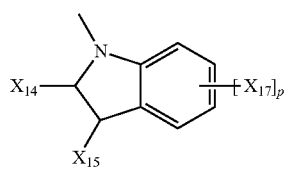

ii

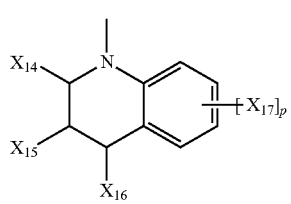

iii wherein $X_{14}$, $X_{15}$, and $X_{16}$ are independently chosen for each occurrence from hydrogen, a lengthening agent L, $C_1$-$C_{18}$ alkyl, phenyl or naphthyl, or $X_{14}$ and $X_{15}$ together form a ring of 5 to 8 carbon atoms, p is an integer chosen from 0, 1, or 2, and $X_{17}$ is independently chosen for each occurrence from a lengthening agent L, $C_1$-$C_{18}$ alkyl, $C_1$-$C_{18}$ alkoxy, or halogen;

(f) immediately adjacent $R^1$ groups, and immediately adjacent $R^2$ groups, in each case independently together form a group represented by Formula vii, viii, or ix,

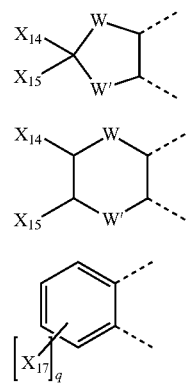

wherein,
(i) W and W' are independently chosen for each occurrence from —O—, —$N(X_7)$—, —$C(X_{14})$—, and —$C(Xr_{17})$—,
(ii) wherein $X_{14}$ and $X_{15}$ are independently chosen for each occurrence from hydrogen, a lengthening agent L, $C_1$-$C_{18}$ alkyl, phenyl or naphthyl, or $X_{14}$ and $X_{15}$ together form a ring of 5 to 8 carbon atoms; and $X_{17}$ is independently chosen for each occurrence from a lengthening agent L, $C_1$-$C_{18}$ alkyl, $C_1$-$C_{18}$ alkoxy, or halogen, and
(iii) q is an integer chosen from 0, 1, 2, 3, and 4;

(g) lengthening agent L;
(h) a group B selected from,
(i) hydrogen, $C_1$-$C_{18}$ alkyl, $C_2$-$C_{18}$ alkylidene, $C_2$-$C_{18}$ alkylidyne, vinyl, $C_3$-$C_{10}$ cycloalkyl, $C_1$-$C_{18}$ haloalkyl, allyl, halogen, and benzyl that is unsubstituted or mono-substituted with at least one of $C_1$-$C_{18}$ alkyl and $C_1$-$C_{18}$ alkoxy;
(ii) phenyl that is mono-substituted at the para position with at least one substituent chosen from: $C_1$-$C_{18}$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_{18}$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material,
(iii) —$CH(CN)_2$ and —$CH(COOX_1)_2$, wherein $X_1$ is chosen from at least one of hydrogen, a lengthening agent L, $C_1$-$C_{18}$ alkyl that is unsubstituted or mono-substituted with phenyl, phenyl($C_1$-$C_{18}$)alkyl that is mono-substituted with $C_1$-$C_{18}$ alkyl, $C_1$-$C_{18}$ haloalkyl or $C_1$-$C_{18}$ alkoxy, and an aryl group that is unsubstituted, mono- or di-substituted, wherein each aryl substituent is independently chosen from $C_1$-$C_{18}$ alkyl and $C_1$-$C_{18}$ alkoxy, and lengthening agent L,
(iv) —$CH(X_2)(X_3)$, wherein,
(1) $X_2$ is chosen from at least one of hydrogen, a lengthening agent L, $C_1$-$C_{18}$ alkyl, and an aryl group that is unsubstituted, mono- or di-substituted, wherein each aryl substituent is independently chosen from $C_1$-$C_{18}$ alkyl and $C_1$-$C_{18}$ alkoxy; and (2) $X_3$ is chosen from at least one of —COOX$_1$, —COX$_1$, —COX$_4$, and —CH$_2$OX$_5$, wherein, $X_4$ is chosen from at least one of morpholino, piperidino, amino that is unsubstituted, mono- or di-substituted with $C_1$-$C_{18}$ alkyl, and an unsubstituted, mono- or di-substituted group chosen from phenylamino and diphenylamino, wherein each substituent is independently chosen from $C_1$-$C_{18}$ alkyl or $C_1$-$C_{18}$ alkoxy; and $X_5$ is chosen from hydrogen, a lengthening agent L, —C(O)X$_2$, $C_1$-$C_{18}$ alkyl that is unsubstituted or mono-substituted with ($C_1$-$C_{18}$) alkoxy or phenyl, phenyl($C_1$-$C_{18}$)alkyl that is mono-substituted with ($C_1$-$C_{18}$)alkoxy, and an aryl group that is unsubstituted, mono- or di-substituted, wherein each aryl substituent is independently chosen from $C_1$-$C_{18}$ alkyl and $C_1$-$C_{18}$ alkoxy;

(v) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl; wherein each aryl and heteroaromatic group substituent is independently chosen for each occurrence from:

(1) lengthening agent L, (2) —COOX$_1$ or —C(O)X$_6$;

(3) aryl, halogen, haloaryl, $C_3$-$C_{10}$ cycloalkylaryl, and an aryl group that is mono- or di-substituted with $C_1$-$C_{18}$ alkyl or $C_1$-$C_{18}$ alkoxy;

(4) $C_1$-$C_{18}$ alkyl, $C_3$-$C_{10}$ cycloalkyl, $C_3$-$C_{10}$ cycloalkyloxy($C_1$-$C_{18}$)alkyl, aryl($C_1$-$C_{18}$)alkyl, aryloxy($C_1$-$C_{18}$)alkyl, mono- or di-($C_1$-$C_{18}$)alkylaryl($C_1$-$C_{18}$)alkyl, mono- or di-($C_1$-$C_{18}$)alkoxyaryl($C_1$-$C_{18}$)alkyl, $C_1$-$C_{18}$ haloalkyl, and mono($C_1$-$C_{18}$)alkoxy($C_1$-$C_{18}$)alkyl;

(5) $C_1$-$C_{18}$ alkoxy, $C_3$-$C_{10}$ cycloalkoxy, cycloalkyloxy($C_1$-$C_{18}$)alkoxy, aryl($C_1$-$C_{18}$)alkoxy, aryloxy($C_1$-$C_{18}$)alkoxy, mono- or di-($C_1$-$C_{18}$)alkylaryl($C_1$-$C_{18}$)alkoxy, and mono- or di-($C_1$-$C_{18}$) alkoxyaryl($C_1$-$C_{18}$)alkoxy;

(6) aminocarbonyl, aminocarbonyl($C_1$-$C_{18}$)alkylene, amino, mono- or di-alkylamino, diarylamino, piperazino, N—($C_1$-$C_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(7) —OX$_7$ or —N(X$_7$)$_2$;

(8) —SX$_{11}$;

(9) a nitrogen containing ring represented by Formula i;

(10) a group represented by Formula ii or iii;

(11) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, $C_1$-$C_{18}$ alkyl, $C_1$-$C_{18}$ alkoxy, phenyl, hydroxy, amino or halogen;

(12) a group represented by Formula iv or v:

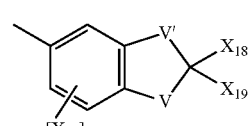

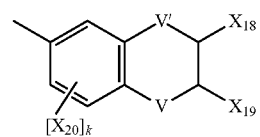

wherein,
(I) V' is independently chosen in each formula from —O—, —CH—, $C_1$-$C_6$ alkylene, and $C_3$-$C_{10}$ cycloalkylene,
(II) V is independently chosen in each formula from —O— or —N(X$_{21}$)—, wherein X$_{21}$ is hydrogen, a lengthening agent L, $C_1$-$C_{18}$ alkyl, and $C_2$-$C_{18}$ acyl, provided that if V is —N(X$_{21}$)—, V' is —CH$_2$—,
(III) X$_{18}$ and X$_{19}$ are each independently chosen from hydrogen, a lengthening agent L, and $C_1$-$C_{18}$ alkyl, and
(IV) k is chosen from 0, 1, and 2, and each X$_{20}$ is independently chosen for each occurrence from a lengthening agent L, $C_1$-$C_{18}$ alkyl, $C_1$-$C_{18}$ alkoxy, hydroxy and halogen, and

(13) a group represented by Formula vi:

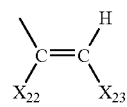

wherein
(I) X$_{22}$ is chosen from hydrogen, a lengthening agent L, and $C_1$-$C_{18}$ alkyl, and
(II) X$_{23}$ is chosen from a lengthening agent L and an unsubstituted, mono-, or di-substituted group chosen from naphthyl, phenyl, furanyl and thienyl, wherein each substituent is independently chosen for each occurrence from $C_1$-$C_{18}$ alkyl, $C_1$-$C_{18}$ alkoxy, and halogen;

(D) $R^3$ and $R^4$ are each independently selected from,
(i) hydrogen, $C_1$-$C_{20}$ alkyl, $C_1$-$C_{20}$ haloalkyl, $C_3$-$C_{10}$ cycloalkyl, allyl, benzyl, or mono-substituted benzyl, said benzyl substituents being chosen from halogen, $C_1$-$C_{20}$ alkyl or $C_1$-$C_{20}$ alkoxy;
(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, $C_1$-$C_{20}$ alkyl or $C_1$-$C_{20}$ alkoxy;
(iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material;
(iv) the group —CH(R$^{10}$)G, wherein R$^{10}$ is hydrogen, $C_1$-$C_{20}$ alkyl or the unsubstituted, mono- or di-substituted aryl groups phenyl or naphthyl, and G is —CH$_2$OR$^{11}$, wherein R$^{11}$ is hydrogen, —C(O)R$^{10}$, C$_1$-C$_{20}$ alkyl, C$_1$-C$_{20}$ alkoxy(C$_1$-C$_{20}$)alkyl, phenyl (C$_1$-C$_{20}$)alkyl, mono(C$_1$-C$_{20}$)alkoxy substituted phenyl(C$_1$-C$_{20}$)alkyl, or the unsubstituted, mono- or di-substituted aryl groups phenyl or naphthyl, each of said phenyl and naphthyl group substituents being C$_1$-C$_{20}$ alkyl or C$_1$-C$_{20}$ alkoxy; or (v) R$^3$ and R$^4$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or C$_1$-C$_{20}$ alkyl; and (E) R$^5$ is selected from hydrogen and —C(O)—R$^{13}$.

3. The indeno-fused ring compound of claim 1, wherein, (A) Ring-A is unsubstituted aryl or substituted aryl;

(B) Q' is selected from bromo, chloro, —NR$^a$R$^a$, —C(O)R$^a$, —C(O)OR$^a$, and lengthening agent L, wherein each R$^a$ is independently selected from hydrogen and an alkyl group having from 1 to 6 carbon atoms, or two R$^a$ groups come together with —N and an additional N atom to form a heterocycloalkyl and R$^b$ is selected from a perfluorinated alkyl group having from 1 to 6 carbon atoms, and for lengthening agent L, d', e' and f' are each independently chosen from 0, 1, 2, 3, and 4, provided that a sum of d'+e'+f' is at least 3;

(C) R$^1$ for each i, and R$^2$ for each t, are each independently selected from, (a) —C(O)X$_{24}$, wherein X$_{24}$ is chosen from lengthening agent L, hydroxy, C$_1$-C$_{12}$ alkyl, C$_1$-C$_{12}$ alkoxy, phenyl that is unsubstituted or mono-substituted with C$_1$-C$_6$ alkyl or C$_1$-C$_6$ alkoxy, amino that is unsubstituted, mono- or di-substituted with at least one of C$_1$-C$_6$ alkyl, phenyl, benzyl, and naphthyl;

(b) —OX$_7$ and —N(X$_7$)$_2$; wherein X$_7$ is chosen from, (i) hydrogen, a lengthening agent L, C$_1$-C$_{12}$ alkyl, C$_1$-C$_{12}$ acyl, phenyl(C$_1$-C$_{12}$)alkyl, mono(C$_1$-C$_{12}$) alkyl substituted phenyl(C$_1$-C$_{12}$)alkyl, mono(C$_1$-C$_{12}$)alkoxy substituted phenyl(C$_1$-C$_{12}$)alkyl; C$_1$-C$_{12}$ alkoxy(C$_1$-C$_{12}$)alkyl; C$_3$-C$_7$ cycloalkyl; mono(C$_1$-C$_{12}$)alkyl substituted C$_3$-C$_7$ cycloalkyl, C$_1$-C$_{12}$ haloalkyl, allyl, benzoyl, mono-substituted benzoyl, naphthoyl or mono-substituted naphthoyl, wherein each of said benzoyl and naphthoyl substituents are independently chosen from C$_1$-C$_6$ alkyl, and C$_1$-C$_6$ alkoxy;

(ii) —CH(X$_8$)X$_9$, wherein X$_8$ is chosen from hydrogen, a lengthening agent L, or C$_1$-C$_{12}$ alkyl; and X$_9$ is chosen from a lengthening agent L, —CN, —CF$_3$, or —COOX$_{10}$, wherein X$_{10}$ is chosen from hydrogen, a lengthening agent L, or C$_1$-C$_{12}$ alkyl;

(iii) —C(O)X$_6$, wherein X$_6$ is chosen from at least one of, hydrogen, a lengthening agent L, C$_1$-C$_{12}$ alkoxy, phenoxy that is unsubstituted, mono- or di-substituted with C$_1$-C$_{12}$ alkyl or C$_1$-C$_{12}$ alkoxy, an aryl group that is unsubstituted, mono- or di-substituted with C$_1$-C$_6$ alkyl or C$_1$-C$_6$ alkoxy, an amino group that is unsubstituted, mono- or di-substituted with C$_1$-C$_6$ alkyl, and a phenylamino group that is unsubstituted, mono- or di-substituted with C$_1$-C$_6$ alkyl or C$_1$-C$_6$ alkoxy;

(c) a nitrogen containing ring represented by Formula i;

i wherein, each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —S(O)—, —SO$_2$≤, —NH—, —N(R$_{13}$')—, or —N(aryl)-, wherein each R$_{13}$' is independently a lengthening group L, or C$_1$-C$_{20}$ alkyl, each aryl is independently phenyl or naphthyl, m is an integer 1, 2 or 3, and p is an integer 0, 1, 2, or 3, provided that when p is 0, Z is —Y—;

(d) the group represented by Formula II or iii;

ii iii wherein X$_{14}$, X$_{15}$, and X$_{16}$ are independently chosen for each occurrence from hydrogen, a lengthening agent L, C$_1$-C$_{12}$ alkyl, phenyl or naphthyl, or X$_{14}$ and X$_{15}$ together form a ring of 5 to 7 carbon atoms; p is an integer chosen from 0, 1, or 2, and X$_{17}$ is independently chosen for each occurrence from a lengthening agent L, C$_1$-C$_{12}$ alkyl, C$_1$-C$_{12}$ alkoxy, or halogen;

(e) immediately adjacent R$^1$ groups, and immediately adjacent R$^2$ groups, in each case independently together form a group represented by Formula vii, viii, or ix, vii viii ix wherein,
(i) W and W' are independently chosen for each occurrence from —O—, —N($X_7$)—, —C($X_{14}$)—, and —C($X_{17}$)—,
(ii) wherein $X_{14}$ and $X_{15}$ are independently chosen for each occurrence from hydrogen, a lengthening agent L, $C_1$-$C_{12}$ alkyl, phenyl or naphthyl, or $X_{14}$ and $X_{15}$ together form a ring of 5 to 7 carbon atoms; and $X_{17}$ is independently chosen for each occurrence from a lengthening agent L, $C_1$-$C_{12}$ alkyl, $C_1$-$C_{12}$ alkoxy, or halogen, and
(iii) q is an integer chosen from 0 to 3;
(f) lengthening agent L,
(g) a group B selected from,
(i) $C_1$-$C_{12}$ alkyl, $C_3$-$C_7$ cycloalkyl, $C_1$-$C_{12}$ haloalkyl and benzyl that is unsubstituted or mono-substituted with at least one of $C_1$-$C_8$ alkyl and $C_1$-$C_6$ alkoxy;
(ii) —CH(CN)$_2$ and —CH(COO$X_1$)$_2$, wherein $X_1$ is chosen from at least one of hydrogen, lengthening agent L, $C_1$-$C_{12}$ alkyl that is unsubstituted or mono-substituted with phenyl, phenyl($C_1$-$C_6$)alkyl that is mono-substituted with $C_1$-$C_6$ alkyl or $C_1$-$C_6$ alkoxy, and an aryl group that is unsubstituted, mono- or di-substituted, wherein each aryl substituent is independently chosen from $C_1$-$C_6$ alkyl and $C_1$-$C_6$ alkoxy; and lengthening agent L;
(iii) —CH($X_2$)($X_3$), wherein,
(1) $X_2$ is chosen from at least one of lengthening agent L, $C_1$-$C_{12}$ alkyl, and an aryl group that is unsubstituted, mono- or di-substituted, wherein each aryl substituent is independently chosen from $C_1$-$C_6$ alkyl and $C_1$-$C_6$ alkoxy; and
(2) $X_3$ is chosen from at least one of —COO$X_1$, —CO$X_1$, —COO$X_4$, and —CH$_2$O$X_5$, wherein: $X_4$ is chosen from at least one of morpholino, piperidino, amino that is unsubstituted, mono- or di-substituted with $C_1$-$C_6$ alkyl, and an unsubstituted, mono or di-substituted group chosen from phenylamino and diphenylamino, wherein each substituent is independently chosen from $C_1$-$C_6$ alkyl or $C_1$-$C_6$ alkoxy; and $X_5$ is chosen from hydrogen, lengthening agent L, —C(O)$X_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$)alkoxy, and an aryl group that is unsubstituted, mono- or di-substituted, wherein each aryl substituent is independently chosen from $C_1$-$C_6$ alkyl and $C_1$-$C_6$ alkoxy;
(iv) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl; wherein each aryl and heteroaromatic group substituent is independently chosen for each occurrence from:
(1) lengthening agent L;
(2) —COO$X_1$ or —C(O)$X_6$;
(3) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
(4) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$) alkyl, haloalkyl, and mono($C_1$-$C_{12}$)alkoxy($C_1$-$C_{12}$)alkyl;
(5) $C_1$-$C_{12}$ alkoxy, $C_3$-$C_7$ cycloalkoxy, cycloalkyloxy ($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$)alkoxy, and mono- or di-($C_1$-$C_{12}$)alkoxyaryl ($C_1$-$C_{12}$)alkoxy;
(6) amido, amino, mono- or di-alkylamino, diarylamino, piperazino, N—($C_1$-$C_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(7) —O$X_7$ or —N($X_7$)$_2$;
(8) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from lengthening agent L, $C_1$-$C_8$ alkyl, $C_1$-$C_8$ alkoxy, phenyl, hydroxy, amino or halogen;
(D) $R^3$ and $R^4$ are each independently selected from hydrogen, $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spiro-carbocyclic ring containing 3 to 6 carbon atoms; and
(E) $R^5$ is selected from hydrogen and —C(O)—$R^{13}$.

4. The indeno-fused ring compound of claim 1, wherein,
(A) Ring-A is unsubstituted aryl or substituted aryl;
(B) for Q', each $R^a$ is independently selected from hydrogen and an alkyl group having from 1 to 6 carbon atoms, and $R^b$ is selected from a perfluorinated alkyl group having from 1 to 6 carbon atoms;
(C) $R^1$ for each i, and $R^2$ for each t, are each independently selected from,
(a) —C(O)$X_{24}$, wherein $X_{24}$ is chosen from hydroxy, $C_1$-$C_6$ alkyl, $C_1$-$C_6$ alkoxy, phenyl that is unsubstituted or mono-substituted with $C_1$-$C_6$ alkyl or $C_1$-$C_6$ alkoxy, amino that is unsubstituted, mono- or di-substituted with at least one of $C_1$-$C_6$ alkyl, phenyl, benzyl, and naphthyl;
(b) —O$X_7$ and —N($X_7$)$_2$; wherein $X_7$ is chosen from,
(i) hydrogen, $C_1$-$C_6$ alkyl, $C_1$-$C_6$ acyl, phenyl($C_1$-$C_6$) alkyl, mono($C_1$-$C_6$)alkyl substituted phenyl($C_1$-$C_6$)alkyl, mono($C_1$-$C_6$)alkoxy substituted phenyl ($C_1$-$C_6$)alkyl; $C_1$-$C_6$ alkoxy($C_1$-$C_6$)alkyl; $C_3$-$C_5$ cycloalkyl; mono($C_1$-$C_6$)alkyl substituted $C_3$-$C_5$ cycloalkyl, $C_1$-$C_6$ haloalkyl, allyl, benzoyl, mono-substituted benzoyl, naphthoyl or mono-substituted naphthoyl, wherein each of said benzoyl and naphthoyl substituents are independently chosen from $C_1$-$C_3$ alkyl, and $C_1$-$C_3$ alkoxy,
(ii) —CH($X_8$)$X_9$, wherein $X_8$ is chosen from hydrogen or $C_1$-$C_6$ alkyl; and $X_9$ is chosen from —CN, —CF$_3$, or —COO$X_{10}$, wherein $X_{10}$ is chosen from hydrogen or $C_1$-$C_6$ alkyl, and
(iii) —C(O)$X_6$, wherein $X_6$ is chosen from hydrogen, $C_1$-$C_{12}$ alkoxy, phenoxy that is unsubstituted, mono- or di-substituted with $C_1$-$C_6$ alkyl or $C_1$-$C_6$ alkoxy, an aryl group that is unsubstituted, mono- or di-substituted with $C_1$-$C_3$ alkyl or $C_1$-$C_3$ alkoxy, an amino group that is unsubstituted, mono- or di-substituted with $C_1$-$C_3$ alkyl, and a phenylamino group that is unsubstituted, mono- or di-substituted with $C_1$-$C_3$ alkyl or $C_1$-$C_3$ alkoxy;

(c) nitrogen containing ring represented by Formula i,

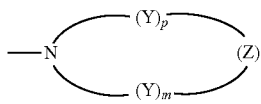

i wherein, each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —S(O)—, —SO$_2$—, —NH—, —N(R$_{13}$')—, or —N(aryl)-, wherein each R$_{13}$' is independently lengthening group L, or C$_1$-C$_{20}$ alkyl, each aryl is independently phenyl or naphthyl, m is an integer 1, 2 or 3, and p is an integer 0, 1, 2, or 3, provided that when p is 0, Z is —Y—;

(d) a group represented by Formula ii or iii,

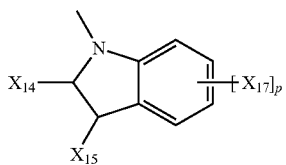

ii

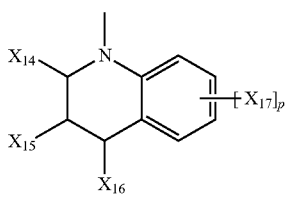

iii wherein X$_{14}$, X$_{15}$, and X$_{16}$ are independently chosen for each occurrence from hydrogen, C$_1$-C$_6$ alkyl, or phenyl or X$_{14}$ and X$_{15}$ together form a ring of 5 to 7 carbon atoms; p is an integer chosen from 0, 1, or 2, and X$_{17}$ is independently chosen for each occurrence from C$_1$-C$_6$ alkyl, C$_1$-C$_6$ alkoxy, or halogen;

(e) immediately adjacent R$^1$ groups, and immediately adjacent R$^2$ groups, in each case independently together form a group represented by Formula vii, viii, or ix,

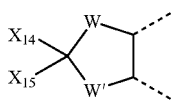

vii

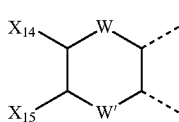

viii

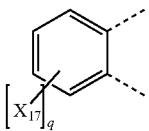

ix wherein,
(i) W and W' are independently chosen for each occurrence from —O—, —N(X$_7$)—, —C(X$_{14}$)—, and —C(X$_{17}$)—,
(ii) wherein X$_{14}$ and X$_{15}$ are independently chosen for each occurrence from hydrogen, C$_1$-C$_6$ alkyl, phenyl or naphthyl, or X$_{14}$ and X$_{15}$ together form a ring of 5 to 7 carbon atoms; and X$_{17}$ is independently chosen for each occurrence from C$_1$-C$_6$ alkyl, C$_1$-C$_6$ alkoxy, or halogen, and
(iii) q is an integer chosen from 0 to 3;
(f) lengthening agent L,
(g) a group B selected from,
(i) C$_1$-C$_6$ alkyl, C$_3$-C$_5$ cycloalkyl, C$_1$-C$_6$ haloalkyl and benzyl that is unsubstituted or mono-substituted with at least one of C$_1$-C$_3$ alkyl and C$_1$-C$_3$ alkoxy;
(ii) —CH(CN)$_2$ and —CH(COOX$_1$)$_2$, wherein X$_1$ is chosen from hydrogen, C$_1$-C$_6$ alkyl that is unsubstituted or mono-substituted with phenyl, phenyl (C$_1$-C$_3$)alkyl that is mono-substituted with C$_1$-C$_3$ alkyl or C$_1$-C$_3$ alkoxy, and an aryl group that is unsubstituted, mono- or di-substituted, wherein each aryl substituent is independently chosen from C$_1$-C$_3$ alkyl and C$_1$-C$_3$ alkoxy; and lengthening agent L;
(iv) —CH(X$_2$)(X$_3$), wherein,
(1) X$_2$ is chosen from at least one of lengthening agent L, C$_1$-C$_6$ alkyl, and an aryl group that is unsubstituted, mono- or di-substituted, wherein each aryl substituent is independently chosen from C$_1$-C$_3$ alkyl and C$_1$-C$_3$ alkoxy; and
(2) X$_3$ is chosen from at least one of —COOX$_1$, —COX$_1$, —COX$_4$, and —CH$_2$OX$_5$, wherein: X$_4$ is chosen from at least one of morpholino, piperidino, amino that is unsubstituted, mono- or di-substituted with C$_1$-C$_3$ alkyl, and an unsubstituted, mono or di-substituted group chosen from phenylamino and diphenylamino, wherein each substituent is independently chosen from C$_1$-C$_3$ alkyl or C$_1$-C$_3$ alkoxy; and X$_5$ is chosen from hydrogen, lengthening agent L, —C(O)X$_2$, C$_1$-C$_6$ alkyl that is unsubstituted or mono-substituted with (C$_1$-C$_6$)alkoxy or phenyl, phenyl(C$_1$-C$_{12}$)alkyl that is mono-substituted with (C$_1$-C$_6$)alkoxy, and an aryl group that is unsubstituted, mono- or di-substituted, wherein each aryl substituent is independently chosen from C$_1$-C$_3$ alkyl and C$_1$-C$_3$ alkoxy;
(v) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl; wherein each substituent is independently chosen for each occurrence from,
(1) lengthening agent L;
(2) —C(O)X$_6$;

(3) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
(4) $C_1$-$C_6$ alkyl, $C_3$-$C_6$ cycloalkyl, $C_3$-$C_5$ cycloalkyloxy($C_1$-$C_6$)alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$)alkoxyaryl($C_1$-$C_6$)alkyl, haloalkyl, and mono($C_1$-$C_6$)alkoxy($C_1$-$C_6$)alkyl;
(5) $C_1$-$C_6$ alkoxy, $C_3$-$C_5$ cycloalkoxy, cycloalkyloxy($C_1$-$C_6$)alkoxy, aryl($C_1$-$C_6$)alkoxy, aryloxy($C_1$-$C_6$)alkoxy, mono- or di-($C_1$-$C_6$)alkylaryl($C_1$-$C_6$)alkoxy, and mono- or di-($C_1$-$C_6$)alkoxyaryl($C_1$-$C_6$)alkoxy;
(6) aminocarbonyl, aminocarbonyl($C_1$-$C_{18}$)alkylene, amino, mono- or di-alkylamino, diarylamino, piperazino, N—($C_1$-$C_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(7) —$OX_7$ or —$N(X_7)_2$, and
(8) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from lengthening agent L, $C_1$-$C_3$ alkyl, $C_1$-$C_3$ alkoxy, phenyl, hydroxy, amino or halogen;
(D) $R^3$ and $R^4$ are each independently selected from hydrogen, $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spiro-carbocyclic ring containing 3 to 6 carbon atoms; and
(E) $R^5$ is selected from hydrogen and —C(O)—$R^{13}$.

5. The indeno-fused ring compound of claim 4, wherein said indeno-fused ring compound is represented by the following Formula Ia,

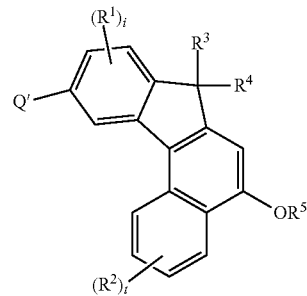

Ia wherein t is selected from 0 to 4.

6. The indeno-fused ring compound of claim 5, wherein Q' is selected from —CN, —C(O)$OR^a$, —C(O)$R^a$, —C≡C—$R^a$, —C($R^a$)=C($R^a$)($R^a$), —OC(O)$R^a$, —OC(O)$OR^a$, —$SR^a$, —OS($O_2$)$R^b$ and —C(O)$NR^aR^a$.

* * * * *